(12) United States Patent
Freeman et al.

(10) Patent No.: US 11,819,369 B2
(45) Date of Patent: Nov. 21, 2023

(54) AUGMENTED REALITY DEVICE FOR PROVIDING FEEDBACK TO AN ACUTE CARE PROVIDER

(71) Applicant: ZOLL Medical Corporation, Chelmsford, MA (US)

(72) Inventors: Gary A. Freeman, Waltham, MA (US); Guy R. Johnson, Wilton, NH (US); Justin R. Carroll, Brighton, CO (US); Brett B. Bonner, Littleton, MA (US)

(73) Assignee: ZOLL Medical Corporation, Chelmsford, MA (US)

(\*) Notice: Subject to any disclaimer, the term of this patent is extended or adjusted under 35 U.S.C. 154(b) by 1287 days.

(21) Appl. No.: 16/353,482

(22) Filed: Mar. 14, 2019

(65) Prior Publication Data
US 2019/0282324 A1 Sep. 19, 2019

Related U.S. Application Data

(60) Provisional application No. 62/643,327, filed on Mar. 15, 2018.

(51) Int. Cl.
*A61H 31/00* (2006.01)
*A61B 90/00* (2016.01)
(Continued)

(52) U.S. Cl.
CPC ............. *A61B 90/36* (2016.02); *A61B 1/05* (2013.01); *A61B 1/267* (2013.01); *A61B 34/25* (2016.02);
(Continued)

(58) Field of Classification Search
CPC .................................................. A61H 31/005
See application file for complete search history.

(56) References Cited

U.S. PATENT DOCUMENTS 7,650,181 B2   1/2010   Freeman et al.
8,880,166 B2   11/2014  Tan et al.
(Continued)

OTHER PUBLICATIONS

Nurmi et al., "Adherence to guidelines when positioning the defibrillation electrodes", Resuscitation, 2004, pp. 143-147, vol. 61.
(Continued)

*Primary Examiner* — LaToya M Louis
(74) *Attorney, Agent, or Firm* — THE WEBB LAW FIRM

(57) ABSTRACT

A spatially sensitive augmented reality system for providing resuscitative feedback in a mixed reality environment to an acute care provider during occurrence of a cardiac event in a patient includes a wearable augmented reality device having at least one three-dimensional sensor, a visual display for viewing by the acute care provider, and at least one processor. The at least one processor is configured to receive and process three-dimensional information of a scene of the cardiac event; produce a three-dimensional representation of a field of view of the acute care provider based on the processed three-dimensional information; identify one or more physical objects associated with the cardiac event in the three-dimensional representation; generate at least one virtual three-dimensional object within the three-dimensional representation; and generate an image of the virtual three-dimensional object within the three-dimensional representation on the visual display.

59 Claims, 33 Drawing Sheets

(51) Int. Cl.
| | |
|---|---|
| *A61M 16/00* | (2006.01) |
| *A61B 1/267* | (2006.01) |
| *A61M 16/04* | (2006.01) |
| *A61B 1/05* | (2006.01) |
| *G09B 5/02* | (2006.01) |
| *G09B 23/28* | (2006.01) |
| *A61B 34/00* | (2016.01) |
| *A61N 1/39* | (2006.01) |
| *A61B 34/20* | (2016.01) |
| *A61B 90/96* | (2016.01) |

(52) U.S. Cl.
CPC ....... *A61H 31/005* (2013.01); *A61M 16/0084* (2014.02); *A61M 16/0488* (2013.01); *A61N 1/39044* (2017.08); *A61N 1/3993* (2013.01); *G09B 5/02* (2013.01); *G09B 23/288* (2013.01); *A61B 90/96* (2016.02); *A61B 2034/2048* (2016.02); *A61B 2034/254* (2016.02); *A61B 2034/256* (2016.02); *A61B 2090/365* (2016.02); *A61B 2090/371* (2016.02); *A61B 2090/372* (2016.02); *A61B 2090/373* (2016.02); *A61H 2201/10* (2013.01); *A61H 2201/5012* (2013.01); *A61H 2201/5043* (2013.01); *A61M 2205/507* (2013.01); *A61M 2205/6072* (2013.01)

(56) References Cited

U.S. PATENT DOCUMENTS

| | | | |
|---|---|---|---|
| 9,429,912 | B2 | 8/2016 | Fleck et al. |
| 10,667,988 | B2 * | 6/2020 | Freeman ............... G06T 15/205 |
| 2013/0296719 | A1 | 11/2013 | Packer et al. |
| 2014/0096091 | A1 | 4/2014 | Reid et al. |
| 2014/0139405 | A1 | 5/2014 | Ribble et al. |
| 2014/0180138 | A1 | 6/2014 | Freeman et al. |
| 2014/0222462 | A1 | 8/2014 | Shakil et al. |
| 2014/0342331 | A1 | 11/2014 | Freeman |
| 2017/0273864 | A1 * | 9/2017 | Kaufman ............. G09B 23/288 |
| 2019/0066538 | A1 * | 2/2019 | Chao .................... A61H 31/005 |

OTHER PUBLICATIONS

Karlon et al., "Effects of Paddle Placement and Size on Defibrillation Current Distribution: A Three-Dimensional Finite Element Model", IEEE Transactions on Biomedical Engineering, 1993, pp. 246-255, vol. 40:3.

Krizhevsky et al., "ImageNet Classification with Deep Convolutional Neural Networks", pp. 1-9.

U.S. Appl. No. 62/643,327, filed Mar. 15, 2018, "Augmented Reality Device for Providing Feedback to an Acute Care Provider".

\* cited by examiner

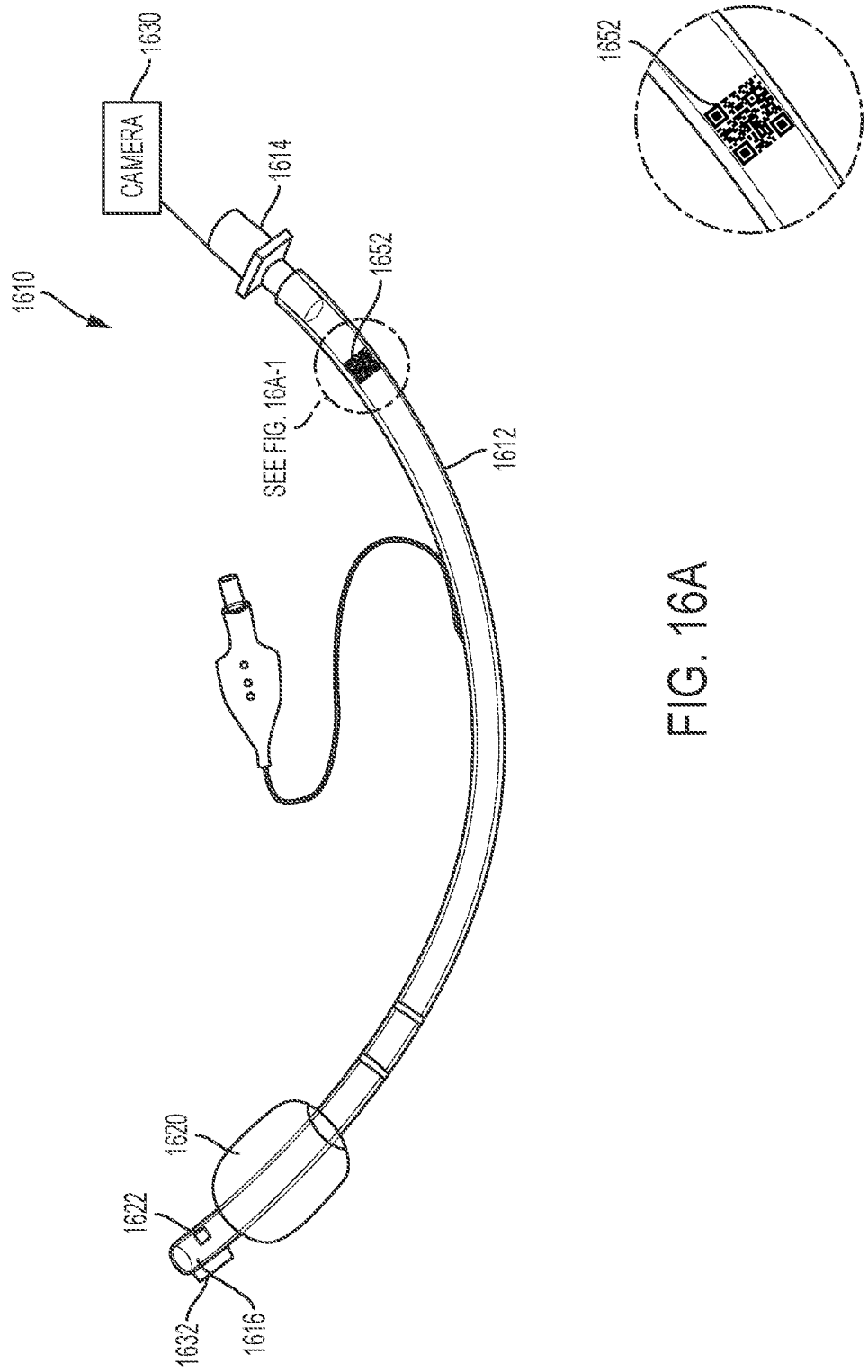

AUGMENTED REALITY DEVICE FOR PROVIDING FEEDBACK TO AN ACUTE CARE PROVIDER

CROSS REFERENCE TO RELATED APPLICATION

The present application claims priority to U.S. Provisional Patent Application No. 62/643,327, filed Mar. 15, 2018, which is hereby incorporated by reference in its entirety.

BACKGROUND

Technological Field

The present disclosure relates to electronic devices that assist acute caregivers by providing guidance and feedback for performing resuscitation activities, and, in some examples, to systems which provide such guidance and feedback through an augmented reality device worn by one or more acute care providers.

Background

Cardio-Pulmonary Resuscitation (CPR) is a process by which one or more acute care providers may attempt to resuscitate a patient who may have suffered an adverse cardiac event by taking one or more actions, for example, providing chest compressions and ventilation to the patient. During the first five to eight minutes after CPR efforts begin, chest compressions are an important element of CPR because chest compressions help maintain blood circulation through the body and in the heart. Ventilation is also a key part of CPR because ventilations help to provide much needed gas exchange (e.g., oxygen supply and carbon dioxide deposit) for the circulating blood.

CPR may be performed by a team of one or more acute care providers, for example, an emergency medical services (EMS) team made up of emergency medical technicians (EMTs), a hospital team including medical caregivers (e.g., doctors, nurses, etc.), and/or bystanders responding to an emergency event. In some instances, one acute care provider can provide chest compressions to the patient while another acute care provider can provide ventilations to the patient, where the chest compressions and ventilations may be time and/or coordinated according to an appropriate CPR protocol. When professionals such as EMTs provide care, ventilation may be provided via a ventilation bag that the acute care provider squeezes, for example, rather than by mouth-to-mouth. CPR can be performed in conjunction with electrical shocks to the patient provided by an external defibrillator, such as an automatic external defibrillator (AED). Such AEDs often provide guidance and instructions (e.g., in the form of audible feedback) to acute care providers, such as "Push Harder," (when the acute care provider is not performing chest compressions according to the desired depth)) "Stop CPR," "Stand Back" (because a shock is about to be delivered), and so on. In order to determine the quality of chest compressions being performed, certain defibrillators may obtain information from one or more accelerometers (such as accelerometers that are provided with the CPR D PADZ®, CPR STAT PADZ®, and ONE STEP™ pads made by ZOLL MEDICAL of Chelmsford, Mass.), which can be used to provide data to determine information, such as depth of chest compressions (e.g., to determine that the compressions are too shallow or too deep and to thus cause an appropriate cue to be provided by the defibrillator).

However, improved systems for collecting information about a rescue effort and for providing guidance, information, and feedback to acute care providers about performance of resuscitation activities would be useful for improving patient care and outcomes. The devices, systems, and techniques discussed herein are intended to provide such benefits.

SUMMARY

According to an aspect of the disclosure, a spatially sensitive augmented reality system for providing resuscitative feedback in a mixed reality environment to an acute care provider during occurrence of a cardiac event in a patient includes a wearable augmented reality device having at least one three-dimensional sensor, a visual display for viewing by the acute care provider, and at least one processor. The at least one processor is configured to: receive and process three-dimensional information of a scene of the cardiac event; produce a three-dimensional representation of a field of view of the acute care provider based on the processed three-dimensional information; identify one or more physical objects associated with the cardiac event in the three-dimensional representation; generate at least one virtual three-dimensional object within the three-dimensional representation; generate an image of the virtual three-dimensional object within the three-dimensional representation on the visual display according to one or more spatially sensitive rules that provides emergency resuscitative guidance to the acute care provider for treating the patient; and manipulate the image of the virtual three-dimensional object within the three-dimensional representation on the visual display as an interaction with the one or more identified physical objects according to the one or more spatially sensitive rules that provides further emergency resuscitative guidance to the acute care provider for treating the patient.

According to another aspect of the disclosure, a spatially sensitive augmented reality system for providing resuscitative information in a mixed reality environment to an acute care provider during occurrence of a cardiac event in a patient includes a wearable augmented reality device having at least one three-dimensional sensor, a visual display for viewing by the acute care provider, and at least one processor. The processor is configured to: receive and process three-dimensional information of a rescue scene of an acute care event to generate a three-dimensional representation of a field of view of the acute care provider; analyze the three-dimensional representation to identify boundaries of one or more physical objects in the three-dimensional representation; apply one or more spatially sensitive rules according to the identified boundaries of the one or more physical objects; and cause the augmented reality device worn by the acute care provider to generate at least one virtual three-dimensional object within the three-dimensional representation of the rescue scene and display at least one image of the virtual three-dimensional object on the visual display within the acute care provider's field of view and outside of the identified boundaries to provide emergency resuscitative guidance for the acute care provider, such that the at least one image of the virtual three-dimensional object abides by the one or more spatially sensitive rules and is prevented from traversing the one or more identified boundaries.

According to another aspect of the disclosure, a spatially sensitive augmented reality system for sharing information in a mixed reality environment between augmented reality devices worn by two or more acute care providers at a rescue scene includes at least one processor. The at least one processor is configured to receive and process three-dimensional information for the rescue scene obtained from at least one first three-dimensional sensor of a first augmented reality device worn by a first acute care provider. The first augmented reality device may include the at least one first three-dimensional sensor and a first visual display. The processor is further configured to apply one or more spatially sensitive rules to the three-dimensional information from the first augmented reality device to determine whether the three-dimensional information is to be shared with other acute care providers and, in accordance with the spatially sensitive rules, cause a second augmented reality device worn by a second acute care provider having at least one second three-dimensional sensor and a second visual display, to generate at least one virtual three-dimensional object within a three-dimensional representation of the rescue scene and display at least one image of the generated virtual three-dimensional object on the second visual display. The at least one virtual three-dimensional object generated by the second augmented reality device can be based on at least a portion of the received and processed information from the first augmented reality device. The virtual three-dimensional object can provide emergency resuscitative guidance for the second acute care provider and can be positioned in the three-dimensional representation of the rescue scene according to the one or more spatially sensitive rules.

According to another aspect of the disclosure, a system for directing activities of acute care providers in a mixed reality environment during an acute care event includes augmented reality devices worn by two or more acute care providers during the acute care event. Each of the augmented reality devices can include at least one three-dimensional sensor, a visual display, and at least one processor. The augmented reality devices can be configured to provide information for assisting the acute care provider in performing at least one acute care activity for a patient according to a role of the respective acute care provider. The system can also include an acute care controller for managing aspects of the acute care event in wireless communication with the augmented reality devices. The acute care controller can be configured to: assign the respective role for each of the acute care providers and apply one or more spatially sensitive rules according to the assigned respective roles and cause each of the augmented reality devices to provide information to the respective acute care provider. Providing information can include displaying an image of at least one virtual three-dimensional object on the visual display within the acute care provider's field of view to provide emergency resuscitative guidance for the acute care provider, such that the at least one virtual three-dimensional object is positioned according to the one or more spatially sensitive rules for performing aspects of the assigned respective role.

According to another aspect of the disclosure, a spatially sensitive augmented reality system for inputting a marker in a mixed reality environment for providing a time-stamped record of an acute care activity includes at least one wearable augmented reality device having at least one three-dimensional sensor, a visual display for viewing by the acute care provider and at least one processor. The processor is configured to: receive and process three-dimensional information of a scene of an acute care event from the at least one augmented reality device worn by the acute care provider to generate a three-dimensional representation of a field of view of the acute care provider; analyze the received and processed three-dimensional representation to identify movement of the acute care provider corresponding to a marker for the acute care activity; and record a time of the identified marker based on time information associated with one or more of the received and processed three-dimensional representation.

According to another aspect of the disclosure, a system for providing information about a location of one or more portable medical devices to a user of a spatially sensitive augmented reality device in a mixed reality environment includes: a wearable augmented reality device having at least one three-dimensional sensor, a visual display for viewing by the acute care provider; and at least one processor. The at least one processor is configured to: receive and process location information from each of the one or more portable medical devices; select a most accessible medical device of the one or more portable medical devices based, at least in part, on the processed location information; apply one or more spatially sensitive rules according to the processed location information; and cause the augmented reality device to generate at least one virtual three-dimensional object and to display an image of the virtual object on the visual display within the acute care provider's field of view, such that the at least image is positioned according to one or more spatially sensitive rules for directing the user to the selected medical device.

According to another aspect of the disclosure, a spatially sensitive augmented reality system for providing resuscitative feedback in a mixed reality environment to an acute care provider during occurrence of an event requiring resuscitation of the patient includes a wearable augmented reality device having at least one three-dimensional sensor, a visual display for viewing by the acute care provider, and at least one processor. The at least one processor is configured to: receive and process three-dimensional information of a scene of the event; produce a three-dimensional representation of a field of view of the acute care provider based on the processed three-dimensional information; identify one or more physical objects associated with the event in the three-dimensional representation; generate at least one virtual three-dimensional object within the three-dimensional representation; generate an image of the virtual three-dimensional object within the three-dimensional representation on the visual display according to one or more spatially sensitive rules that provides emergency resuscitative guidance to the acute care provider for treating the patient; and manipulate the image of the virtual three-dimensional object within the three-dimensional representation on the visual display as an interaction with the one or more identified physical objects according to the one or more spatially sensitive rules that provides further emergency resuscitative guidance to the acute care provider for treating the patient.

According to another aspect of the disclosure, a spatially sensitive augmented reality system for providing resuscitative feedback in a mixed reality environment to an acute care provider during occurrence of a ventilation event in a patient includes a wearable augmented reality device having at least one three-dimensional sensor, a visual display for viewing by the acute care provider, and at least one processor. The at least one processor is configured to: receive and process three-dimensional information of a scene of the ventilation event; produce a three-dimensional representation of a field of view of the acute care provider based on the processed three-dimensional information; identify one or more physical objects associated with the ventilation event in the three-dimensional representation; generate at least one virtual three-dimensional object within the three-dimensional representation; generate an image of the virtual three-dimensional object within the three-dimensional representation on the visual display according to one or more spatially sensitive rules that provides emergency resuscitative guidance to the acute care provider for treating the patient; and manipulate the image of the virtual three-dimensional object within the three-dimensional representation on the visual display as an interaction with the one or more identified physical objects according to the one or more spatially sensitive rules that provides further emergency resuscitative guidance to the acute care provider for treating the patient.

Examples of the present invention will now be described in the following numbered clauses:

Clause 1: A spatially sensitive augmented reality system for providing resuscitative feedback in a mixed reality environment to an acute care provider during occurrence of a cardiac event in a patient, the system comprising: a wearable augmented reality device having at least one three-dimensional sensor, a visual display for viewing by the acute care provider, and at least one processor configured to: receive and process three-dimensional information of a scene of the cardiac event; produce a three-dimensional representation of a field of view of the acute care provider based on the processed three-dimensional information; identify one or more physical objects associated with the cardiac event in the three-dimensional representation; generate at least one virtual three-dimensional object within the three-dimensional representation; generate an image of the virtual three-dimensional object within the three-dimensional representation on the visual display according to one or more spatially sensitive rules that provides emergency resuscitative guidance to the acute care provider for treating the patient; and manipulate the image of the virtual three-dimensional object within the three-dimensional representation on the visual display as an interaction with the one or more identified physical objects according to the one or more spatially sensitive rules that provides further emergency resuscitative guidance to the acute care provider for treating the patient.

Clause 2: The spatially sensitive augmented reality system of clause 1, wherein the one or more spatially sensitive rules for generation of the image of the virtual three-dimensional object on the visual display include a position and orientation relationship between the wearable augmented reality device and a three-dimensional reference frame of the three-dimensional representation of the field of view of the acute care provider.

Clause 3: The spatially sensitive augmented reality system of clause 2, wherein the one or more spatially sensitive rules for manipulation of the image of the virtual three-dimensional object on the visual display include at least one of: a position or orientation relationship between the wearable augmented reality device and the three-dimensional reference frame, and a positional or orientation relationship between the virtual three-dimensional object and the identified one or more physical objects within the three-dimensional representation.

Clause 4: The spatially sensitive augmented reality system of any of clauses 1-3, further comprising an image sensor, wherein the at least one processor is configured to: receive and process image information obtained by the image sensor, and recognize an image object within the processed image information.

Clause 5: The spatially sensitive augmented reality system of clause 4, wherein the at least one processor is configured to correlate the recognized image object with the identified one or more physical objects associated with the cardiac event within the three-dimensional representation.

Clause 6: The spatially sensitive augmented reality system of clause 5, wherein the at least one processor is configured to refine the identified one or more physical objects associated with the cardiac event.

Clause 7: The spatially sensitive augmented reality system of clause 6, wherein the at least one processor is configured to refine the accuracy or specificity of the identified one or more physical objects associated with the cardiac event.

Clause 8: The spatially sensitive augmented reality system of any of clauses 1 to 7, wherein the at least one processor is configured to determine the occurrence of one or more acute care activities of the acute care provider based on the one or more identified physical objects of the three-dimensional representation.

Clause 9: The spatially sensitive augmented reality system of any of clauses 1 to 8, wherein the at least one processor is configured to recognize one of the identified physical objects in the three-dimensional representation as at least one of the patient and another acute care provider associated with an assigned resuscitative role.

Clause 10: The spatially sensitive augmented reality system of any of clauses 1 to 6, wherein the at least one processor is configured to recognize one of the identified physical objects in the three-dimensional representation as at least one of a defibrillator, an electrode assembly, a chest compression sensor, and a ventilation bag.

Clause 11: The spatially sensitive augmented reality system of any of clauses 1 to 6, wherein the at least one processor is configured to recognize one of the identified physical objects in the three-dimensional representation as at least one anatomical feature of a patient.

Clause 12: The spatially sensitive augmented reality system of clause 11, wherein the at least one anatomical feature of the patient comprises at least one of a sternum, a sternal notch, an axilla, ribs, an anterior portion of the patient, a posterior portion of the patient, a desired electrode placement position, and a desired chest compression sensor placement position.

Clause 13: The spatially sensitive augmented reality system of clause 11, wherein the at least one anatomical feature of the patient comprises a desired electrode placement position, and wherein the virtual three-dimensional object comprises a virtual electrode assembly located at the desired electrode placement position.

Clause 14: The spatially sensitive augmented reality system of clause 13, wherein one of the identified physical objects in the three-dimensional representation includes an electrode assembly, and wherein the at least one processor is configured to provide feedback of whether the electrode assembly is placed on the patient's body according to the desired electrode placement position.

Clause 15: The spatially sensitive augmented reality system of clause 14, wherein the feedback of whether the electrode assembly is placed on the patient's body according to the desired electrode placement position comprises at least one of visual feedback, audio feedback, and haptic feedback.

Clause 16: The spatially sensitive augmented reality system of clause 15, wherein the visual feedback of whether the electrode assembly is placed on the patient's body according to the desired electrode placement position comprises a visual indication on the visual display of at least one of whether the electrode assembly is properly placed and interactive guidance of where the electrode assembly should be placed.

Clause 17: The spatially sensitive augmented reality system of clause 16, wherein the visual feedback of whether the electrode assembly is placed on the patient's body according to the desired electrode placement position comprises at least one of a color change in the virtual electrode assembly, a textual message in the field of view, and a graphical indication of whether the electrode assembly is properly placed.

Clause 18: The spatially sensitive augmented reality system of clause 12, wherein the at least one anatomical feature of the patient comprises the desired chest compression sensor placement position, and wherein the virtual three-dimensional object comprises a virtual chest compression sensor located at the desired chest compression sensor placement position.

Clause 19: The spatially sensitive augmented reality system of clause 18, wherein one of the identified physical objects in the three-dimensional representation comprises a chest compression sensor, and the at least one processor is configured to provide feedback of whether the chest compression sensor is placed on the patient's body according to the desired chest compression sensor placement position.

Clause 20: The spatially sensitive augmented reality system of clause 19, wherein the feedback of whether the chest compression sensor is placed on the patient's body according to the desired chest compression sensor placement position comprises at least one of visual feedback, audio feedback, and haptic feedback.

Clause 21: The spatially sensitive augmented reality system of clause 19, wherein another one of the identified physical objects in the three-dimensional representation includes an electrode assembly, and the at least one processor is configured to provide feedback of whether the electrode assembly and the chest compression sensor are placed on the patient's body according to the respective desired electrode placement position and the desired chest compression sensor placement positions.

Clause 22: The spatially sensitive augmented reality system of any of clauses 1-6, wherein the at least one virtual three-dimensional object comprises a virtual CPR indicator overlaid on or within the patient's body within the field of view of the acute care provider, wherein the virtual CPR indicator provides feedback representative of a quality with which the acute care provider is administering CPR to the patient.

Clause 23: The spatially sensitive augmented reality system of clause 22, wherein the virtual CPR indicator comprises a chest compression indicator that provides feedback representative of a quality with which the acute care provider is administering chest compressions to the patient according to whether one or more chest compression parameters are within a desired range.

Clause 24: The spatially sensitive augmented reality system of clause 23, wherein the one or more chest compression parameters comprises at least one of chest compression depth, chest compression rate, acute care provider body alignment, and acute care provider fatigue.

Clause 25: The spatially sensitive augmented reality system of any of clauses 22-24, wherein the virtual CPR indicator comprises a ventilation indicator that provides feedback representative of a quality with which the acute care provider is administering ventilations to the patient according to whether one or more ventilation parameters are within a desired range.

Clause 26: The spatially sensitive augmented reality system of clause 25, wherein the one or more ventilation parameters comprises at least one of tidal volume, minute volume, ventilation rate, flow rate in the patient's airway, inspiratory flow rate, expiratory flow rate, acute care provider body alignment, and acute care provider fatigue.

Clause 27: The spatially sensitive augmented reality system of clause 9, wherein the at least one virtual three-dimensional object comprises an indication instructing acute care providers to switch CPR roles.

Clause 28: The spatially sensitive augmented reality system of any of clauses 1-27, wherein the at least one processor is configured to calibrate the processed three-dimensional information according to the one or more acute care activities based on a user-initiated action by the acute care provider.

Clause 29: The spatially sensitive augmented reality system of clause 28, wherein the user-initiated action comprises connection of an electrode assembly to at least one processor and recognition of the type of electrode assembly to be adult or pediatric.

Clause 30: The spatially sensitive augmented reality system of clause 28, wherein the user-initiated action comprises a manual input from the acute care provider of at least one of patient dimensions, patient size, and patient age.

Clause 31: The spatially sensitive augmented reality system of clause 28, wherein the user-initiated action comprises performance of a calibration protocol by the acute care provider for augmented reality device to determine patient dimensions.

Clause 32: The spatially sensitive augmented reality system of any of clauses 1-6, wherein the one or more spatially sensitive rules comprise rules for positioning the at least one virtual three-dimensional object relative to one or more identified physical objects.

Clause 33: The spatially sensitive augmented reality system of any of clauses 1-6, wherein the at least one processor is configured to determine an occurrence of one or more acute care activities based on analysis of the three-dimensional representation and determine one or more activity parameters for the one or more acute care activities of the acute care provider, wherein the one or more parameters comprise one or more of chest compression rate, chest compression depth, ventilation tidal volume, ventilation minute volume, and ventilation rate.

Clause 34: The spatially sensitive augmented reality system of any of clauses 1-6, wherein the emergency resuscitative guidance is based on a comparison between parameters for one or more resuscitation activities performed by the acute care provider identified based on analysis of the three-dimensional representation and target parameters for the one or more resuscitation activities performed by the acute care provider.

Clause 35: The spatially sensitive augmented reality system of clause 34, wherein the at least one processor is further configured to modify or update the target parameters based on one or more of a condition of the patient, a condition of the acute care provider, a duration of performance of the resuscitation activity, a quality of resuscitation activities being performed, a characteristic of the rescue scene, and a characteristic of other rescuers at the rescue scene.

Clause 36: The spatially sensitive augmented reality system of any of clauses 1-6, wherein the emergency resuscitative guidance comprises virtual three-dimensional objects representative of one or more resuscitation activity parameters representative of a quality of resuscitation activities performed by the acute care provider.

Clause 37: The spatially sensitive augmented reality system of clause 36, wherein the parameters representative of a quality of resuscitation activities performed by the acute care provider comprise one or more of chest compression depth, chest compression rate, acute care provider body alignment, and acute care provider fatigue.

Clause 38: The spatially sensitive augmented reality system of any of clauses 1-6, wherein the virtual three-dimensional object comprises an indicator representative of performance of a resuscitation activity performed by the acute care provider over a predetermined time interval or over a predetermined number of preceding instances of performance of the resuscitation activity.

Clause 39: The spatially sensitive augmented reality system of any of clauses 1-38, further comprising a flow sensor in fluid communication with a ventilation device for providing ventilations to the patient, and wherein the flow sensor is configured to measure one or more of tidal volume, minute volume, ventilation rate, flow rate in the patient's airway, inspiratory flow rate, and expiratory flow rate.

Clause 40: The spatially sensitive augmented reality system of clause 39, wherein the at least one processor is further configured to receive information from the flow sensor, and wherein the emergency resuscitative guidance is based, at least in part, on the received information.

Clause 41: The system of any of clauses 1-40, wherein the identification of the one or more physical objects by the at least one processor comprises identification of at least one medical imaging probe in the three-dimensional representation, the imaging probe being configured to capture image data representative of at least one internal body structure of the patient.

Clause 42: The system of clause 41, wherein the at least one internal body structure comprises at least one of organ(s), bone(s), muscle(s), soft tissue(s) or blood vessel(s) of the patient.

Clause 43: The system of clause 41, wherein the medical imaging probe comprises an ultrasound transducer, and the at least one internal body structure is the patient's heart.

Clause 44: The system of any of clauses 41-43, wherein the at least one processor of the augmented reality device is configured to: determine a location of the at least one imaging probe within the three-dimensional representation of the scene, receive the image data from the at least one imaging probe, and associate the received image data with the location of the imaging probe within the three-dimensional representation when the image data was captured.

Clause 45: The system of clause 44, wherein the at least one processor of the augmented reality device is further configured to analyze the received image data from the imaging probe to identify the internal body structure in the captured image data, and wherein the generated at least one virtual object comprises a virtual representation of the identified internal body structure.

Clause 46: The system of clause 45, further comprising the medical imaging probe configured to capture image data representative of at least one interior body structure of the patient, the medical imaging probe being in wireless electronic communication with the processor of the augmented reality device.

Clause 47: The system of any of clauses 44-46, wherein the image of the at least one virtual object of the internal body structure is based, at least in part, on the image data from the imaging probe.

Clause 48: The system of clause 47, wherein at least one of a size, outward appearance, movement, or positioning of the image of the at least one virtual object is based, at least in part, on the image data from the imaging probe.

Clause 49: The system of any of clauses 44-48, wherein the manipulation of the image of the virtual three-dimensional object within the three-dimensional representation on the visual display is based, at least in part, on the image data from the imaging probe.

Clause 50: The system of any of clauses 44-49, wherein the manipulation of the image of the virtual three-dimensional object comprises causing the image to be displayed within the field of view of the user at a position relative to the patient determined based, at least in part, on the image data from the imaging probe.

Clause 51: The system of any of clauses 1-50, wherein the identification of the one or more physical objects in the three-dimensional representation by the at least one processor comprises identification of at least one insertable medical instrument configured to be inserted through a mouth of the patient.

Clause 52: The system of clause 51, wherein the at least one insertable medical instrument comprises at least one of a tracheal tube or laryngoscope.

Clause 53: The system of clause 51 or clause 52, wherein the identification of the insertable medical instrument in the three-dimensional representation further comprises identification of a tag or code associated with the insertable medical instrument, and wherein the at least one processor of the augmented reality device is configured to determine information about the insertable medical instrument based on the tag or code.

Clause 54: The system of clause 53, wherein the determined information comprises information about a length, inner cross section area, outer cross section area, flexibility, manufacturer, model number, or outward appearance of the insertable medical instrument.

Clause 55: The system of clause 53 or clause 54, wherein the generation of the at least one virtual three-dimensional object within the three-dimensional representation comprises generation of a virtual representation of the insertable medical instrument, and wherein the generation of the image of the virtual representation of the insertable medical instrument on the visual display is based, at least in part, on information determined from the tag or code associated with the insertable medical instrument.

Clause 56: The system of any of clauses 1-55, wherein the at least one processor of the augmented reality device is further configured to receive image data captured from a medical instrument inserted into the patient through the mouth.

Clause 57: The system of clause 56, wherein the generation of the at least one virtual three-dimensional object within the three-dimensional representation comprises generation of a virtual representation of an interior body structure of the patient determined based, at least in part, on the received image data from the inserted medical instrument, and wherein the generation of the image of the virtual representation on the visual display is based, at least in part, on the received image data.

Clause 58: The system of clause 57, wherein the image of the virtual representation of the interior body structure comprises an image of the interior body structure and at least one annotation identifying the interior body structure.

Clause 59: The system of any of clauses 56-58, wherein the at least one processor of the augmented reality device is configured to display the received image data on the visual display in real time, wherein the received image data comprises image data captured from a camera associated with at least one of a tracheal tube or a laryngoscope inserted through the patient's mouth.

Clause 60: The system of clause 59, wherein the at least one processor of the augmented reality device is further configured to automatically analyze the received image data captured from the inserted medical instrument to determine at least one notification related to insertion of the inserted medical instrument and/or treatment of the patient, and to display the at least one notification on the visual display along with the displayed received image data, thereby providing guidance for insertion of the medical instrument through the mouth of the patient and/or treatment of the patient.

Clause 61: A spatially sensitive augmented reality system for providing resuscitative information in a mixed reality environment to an acute care provider during occurrence of a cardiac event in a patient, the system comprising: a wearable augmented reality device having at least one three-dimensional sensor, a visual display for viewing by the acute care provider, and at least one processor configured to: receive and process three-dimensional information of a rescue scene of an acute care event to generate a three-dimensional representation of a field of view of the acute care provider; analyze the three-dimensional representation to identify boundaries of one or more physical objects in the three-dimensional representation; apply one or more spatially sensitive rules according to the identified boundaries of the one or more physical objects; and cause the augmented reality device worn by the acute care provider to generate at least one virtual three-dimensional object within the three-dimensional representation of the rescue scene and display at least one image of the virtual three-dimensional object on the visual display within the acute care provider's field of view and outside of the identified boundaries to provide emergency resuscitative guidance for the acute care provider, such that the at least one image of the virtual three-dimensional object abides by the one or more spatially sensitive rules and is prevented from traversing the one or more identified boundaries.

Clause 62: The spatially sensitive augmented reality system of clause 61, wherein the one or more physical objects comprise one or more of a patient, another acute care provider, a therapeutic medical device, and a monitoring medical device.

Clause 63: The spatially sensitive augmented reality system of clause 61 or clause 62, wherein the at least one virtual three-dimensional object comprises a dashboard display comprising at least one of physiological information for the patient, status information for the acute care provider, and information about the rescue scene.

Clause 64: The spatially sensitive augmented reality system of clause 63, wherein information of the dashboard display is based at least in part on analysis of two dimensional images captured by at least one camera of the augmented reality device.

Clause 65: The spatially sensitive augmented reality system of any of clauses 61-64, wherein the at least one processor is configured to receive an instruction to reposition the virtual three-dimensional object and, based on the received instruction, reposition the virtual object within the three-dimensional representation of the rescue scene so that the image of the virtual object is displayed, within the acute care provider's field of view, at a new location.

Clause 66: The spatially sensitive augmented reality system of clause 65, wherein receiving the instruction comprises analyzing the three-dimensional information to identify a gesture performed by the acute care provider and generate the instruction to reposition the virtual object based on the instruction.

Clause 67: The spatially sensitive augmented reality system of clause 66, wherein the gesture comprises one or more of pointing to a physical or virtual object within the field of view, mimicking grasping a physical or virtual object within the field of view, or mimicking dragging a physical object or virtual object within the field of view.

Clause 68: The spatially sensitive augmented reality system of any of clauses 61-67, wherein the at least one processor analyzes the three-dimensional representation to identify the boundaries of one or more physical objects by one or more of color matching to identify portions of the three-dimensional representation having a similar color and shape matching to identify portions of the three dimensional representation having a shape corresponding to a physical object commonly found at a rescue scene.

Clause 69: The spatially sensitive augmented reality system of clause 68, wherein the physical object commonly found at a rescue scene comprises one or more of: a patient, an acute care provider, a medical device, a disposable medical instrument, a vehicle or patient transportation device, and an environmental hazard.

Clause 70: The spatially sensitive augmented reality system of any of clauses 61-69, further comprising an image sensor configured to acquire two-dimensional images of the rescue scene, and wherein the at least one processor is configured to identify boundaries of physical objects in the three-dimensional representation of the rescue scene based on analysis of the acquired two-dimensional images.

Clause 71: The spatially sensitive augmented reality system of clause 70, wherein the at least one processor is configured to refine boundaries of the identified physical objects within the three-dimensional representation of the rescue scene based on analysis of the acquired two-dimensional images.

Clause 72: The spatially sensitive augmented reality system of clause 71, wherein refining boundaries of the identified physical objects comprises, based on analysis of the two-dimensional images, identifying the physical object in the two-dimensional image and extracting an outline of the physical object by a color matching technique.

Clause 73: A spatially sensitive augmented reality system for sharing information in a mixed reality environment between augmented reality devices worn by two or more acute care providers at a rescue scene, the system comprising at least one processor configured to: receive and process three-dimensional information for the rescue scene obtained from at least one first three-dimensional sensor of a first augmented reality device worn by a first acute care provider, the first augmented reality device comprising the at least one first three-dimensional sensor, and a first visual display; apply one or more spatially sensitive rules to the three-dimensional information from the first augmented reality device to determine whether the three-dimensional information is to be shared with other acute care providers; and in accordance with the spatially sensitive rules, cause a second augmented reality device worn by a second acute care provider having at least one second three-dimensional sensor and a second visual display, to generate at least one virtual three-dimensional object within a three-dimensional representation of the rescue scene and display at least one image of the generated virtual three-dimensional object on the second visual display, wherein the at least one virtual three-dimensional object generated by the second augmented reality device is based on at least a portion of the received and processed information from the first augmented reality device, provides emergency resuscitative guidance for the second acute care provider, and is positioned in the three-dimensional representation of the rescue scene according to the one or more spatially sensitive rules.

Clause 74: The spatially sensitive augmented reality system of clause 73, wherein the at least one processor comprises a processor separate from the augmented reality devices worn by the two or more rescuers.

Clause 75: The spatially sensitive augmented reality system of clause 73 or clause 74, wherein the at least one processor is a processor of at least one of the first augmented reality device and the second augmented reality device.

Clause 76: The spatially sensitive augmented reality system of any of clauses 73-75, wherein determining whether the three-dimensional information is to be shared with other acute care providers based on the spatially sensitive rules comprises: analyzing the three-dimensional information to identify a relative importance of the information to the first acute care provider and to the second acute care provider; and causing the second augmented reality device to generate and display the virtual object when the three-dimensional information is more important to the second acute care provider than to the first acute care provider.

Clause 77: The spatially sensitive augmented reality system of any of clauses 73-76, further comprising the first augmented reality device, wherein the first augmented reality device is configured to provide the three-dimensional information to the at least one processor in response to an user-initiated action of the first acute care provider.

Clause 78: The spatially sensitive augmented reality system of any of clauses 73-77, further comprising the first augmented reality device, and wherein the first augmented reality device is configured to automatically provide the information to the at least one processor at predetermined intervals.

Clause 79: The spatially sensitive augmented reality system of clause 78, wherein the user-initiated action comprises one or more of beginning a resuscitation activity, ceasing a resuscitation activity, setting up a medical device at the rescue scene, administering a treatment to the patient, and completing administering the treatment to the patient.

Clause 80: The spatially sensitive augmented reality system of any of clauses 73-79, wherein the second augmented reality device is configured to manipulate the image of the virtual three-dimensional object within the three-dimensional representation on the second visual display according to the one or more spatially sensitive rules based on additional three-dimensional information from the first augmented reality device to provide further emergency resuscitative guidance to the second acute care provider for treating the patient.

Clause 81: The spatially sensitive augmented reality system of any of clauses 73-80, wherein the one or more spatially sensitive rules for generation of the image of the virtual three-dimensional object on the second visual display includes a position and orientation relationship between the second augmented reality device and a three-dimensional reference frame of the three-dimensional representation of the field of view of the second acute care provider.

Clause 82: A system for directing activities of acute care providers in a mixed reality environment during an acute care event, the system comprising: augmented reality devices worn by two or more acute care providers during the acute care event, each augmented reality device having at least one three-dimensional sensor, a visual display, and at least one processor, and being configured to provide information for assisting the acute care provider in performing at least one acute care activity for a patient according to a role of the respective acute care provider; and an acute care controller for managing aspects of the acute care event in wireless communication with the augmented reality devices, the acute care controller being configured to: assign the respective role for each of the acute care providers; apply one or more spatially sensitive rules according to the assigned respective roles; and cause each of the augmented reality devices to provide information to the respective acute care provider, wherein providing information comprises displaying an image of at least one virtual three-dimensional object on the visual display within the acute care provider's field of view to provide emergency resuscitative guidance for the acute care provider, such that the at least one virtual three-dimensional object is positioned according to the one or more spatially sensitive rules for performing aspects of the assigned respective role.

Clause 83: The system of clause 82, wherein assigning the respective role for each of the augmented reality devices comprises: determining a treatment protocol for the patient, the treatment protocol comprising one or more acute care activities to be provided for the patient; and assigning the respective role for each of the augmented reality devices, such that each of the one or more acute care activities of the treatment protocol is performed by at least one of the acute care providers.

Clause 84: The system of clause 82 or clause 83, wherein the at least one processor is further configured to cause each of the at least one augmented reality devices to provide a notification to the respective acute care provider to change roles after a predetermined time interval.

Clause 85: The system of any of clauses 82-84, wherein assignment of a respective role to each of the acute care providers is based, at least in part, on at least one of physical strength of the acute care provider, an acute care provider's experience with particular types of acute care activity, acute care provider size, acute care provider height, and acute care provider weight.

Clause 86: The system of any of clauses 82-85, wherein a role comprises at least one of: providing chest compressions to a patient; providing ventilation to the patient; setting up a medical device to treat the patient; positioning electrodes on the patient, and administering a therapeutic agent to the patient.

Clause 87: The system of clause 86, wherein the role assigned to one of the acute care providers is providing chest compressions to the patient, and wherein the virtual three-dimensional object for the acute care provider performing the chest compressions comprises a performance indicator.

Clause 88: The system of clause 86, wherein the role assigned to one of the acute care providers is positioning electrodes on the patient, and wherein the virtual three-dimensional object for the acute care provider positioning electrodes on the patient comprises two-dimensional indicators for a desired electrode location on the patient.

Clause 89: The rescue management system of any of clauses 82-88, wherein the at least one acute care activity performed by one acute care provider is different from the at least one acute care activity performed by another acute care provider.

Clause 90: A spatially sensitive augmented reality system for inputting a marker in a mixed reality environment for providing a time-stamped record of an acute care activity, the system comprising: at least one wearable augmented reality device having at least one three-dimensional sensor, a visual display for viewing by the acute care provider and at least one processor configured to: receive and process three-dimensional information of a scene of an acute care event from the at least one augmented reality device worn by the acute care provider to generate a three-dimensional representation of a field of view of the acute care provider;

analyze the received and processed three-dimensional representation to identify movement of the acute care provider corresponding to a marker for the acute care activity; and record a time of the identified marker based on time information associated with one or more of the received and processed three-dimensional representation.

Clause 91: The system of clause 90, wherein the movement comprises one or more of a predetermined hand gesture, a predetermined facial expression, and a predetermined arm movement.

Clause 92: The system of clause 90 or clause 91, wherein the acute care activity comprises at least one of performing chest compressions, manual ventilations, setting up mechanical medical devices, administering medications to the patient, monitoring patient vital signs, coordinating transportation of the patient from the emergency scene to a medical facility, and coordinating exchange of responsibility for treatment of the patient upon arrival at the medical facility.

Clause 93: The system of clause 92, wherein a patient condition treated by the acute care provider comprises at least one of stroke, dyspnea, traumatic arrest, myocardial infarction and cardiac arrest.

Clause 94. The system of any of clauses 90-93, wherein the at least one processor is further configured to determine a treatment protocol for a patient based on the input marker, and to provide emergency resuscitation guidance for the acute care provider according to the determined treatment protocol.

Clause 95: The system of any of clauses 90-94, wherein the at least one processor is further configured to: associate each of the at least one augmented reality devices with a respective acute care provider; and output a summary having information indicative of a quality of care of each acute care provider based, at least in part, on the identified markers for each respective acute care provider.

Clause 96: The system of clause 95, wherein the output summary having information indicative of a quality of care provided by each acute care provider is based, at least in part, on a comparison between information representative of movement of the acute care provider during performance of the acute care activity and target parameters for the acute care activity.

Clause 97: A system for providing information about a location of one or more portable medical devices to a user of a spatially sensitive augmented reality device in a mixed reality environment, the system comprising: a wearable augmented reality device having at least one three-dimensional sensor, a visual display for viewing by the acute care provider, and at least one processor configured to: receive and process location information from each of the one or more portable medical devices; select a most accessible medical device of the one or more portable medical devices based, at least in part, on the processed location information; apply one or more spatially sensitive rules according to the processed location information; and cause the augmented reality device to generate at least one virtual three-dimensional object and to display an image of the virtual object on the visual display within the acute care provider's field of view such that the at least image is positioned according to one or more spatially sensitive rules for directing the user to the selected medical device.

Clause 98: The system of clause 97, wherein the at least one processor is further configured to receive status information for each of the one or more medical devices and wherein selecting the most accessible medical device is based, at least in part, on the received status information.

Clause 99: The system of clause 98, wherein the at least one processor is further configured to cause the augmented reality device to provide within the rescuer's field of view visual indicators of medical device status for the selected medical device.

Clause 100: The system of any of clauses 97-99, wherein the at least one processor is further configured to cause the augmented reality device to provide instructions for deploying the medical device to the user.

Clause 101: The system of any of clauses 97-100, wherein the at least one virtual object comprises at least one of a line, a series of arrows, and an image of a path directing the user to the selected medical device.

Clause 102: The system of any of clauses 97-101, wherein the at least one processor is further configured to generate one or more virtual three-dimensional objects for directing the user in setting up and using the device.

Clause 103: The system of clause 102, wherein the one or more virtual three-dimensional objects for directing the user in setting up and using the device are automatically displayed to the user when the user is within a predetermined distance from the selected medical device.

104: The system of any of clauses 97-103, wherein the at least one processor is configured to cause the augmented reality device to display status information for the selected medical device on the visual display along with the images of the generated virtual three-dimensional object.

Clause 105: The system of clause 97, wherein the portable medical device comprises an automated external defibrillator.

Clause 106: A spatially sensitive augmented reality system for providing resuscitative feedback in a mixed reality environment to an acute care provider during occurrence of an event requiring resuscitation of the patient, the system comprising: a wearable augmented reality device having at least one three-dimensional sensor, a visual display for viewing by the acute care provider, and at least one processor configured to: receive and process three-dimensional information of a scene of the event; produce a three-dimensional representation of a field of view of the acute care provider based on the processed three-dimensional information; identify one or more physical objects associated with the event in the three-dimensional representation; generate at least one virtual three-dimensional object within the three-dimensional representation; generate an image of the virtual three-dimensional object within the three-dimensional representation on the visual display according to one or more spatially sensitive rules that provides emergency resuscitative guidance to the acute care provider for treating the patient; and manipulate the image of the virtual three-dimensional object within the three-dimensional representation on the visual display as an interaction with the one or more identified physical objects according to the one or more spatially sensitive rules that provides further emergency resuscitative guidance to the acute care provider for treating the patient.

Clause 107: The spatially sensitive augmented reality system of clause 106, wherein the event requiring resuscitation of the patient comprises one or more of a cardiac arrest, a respiratory arrest, and a traumatic arrest.

Clause 108: The spatially sensitive augmented reality system of clause 106 or clause 87, further comprising an image sensor, wherein the at least one processor is configured to: receive and process image information obtained by the image sensor, recognize an image object within the processed image information, and correlate the recognized image object with the identified one or more physical objects associated with the event within the three-dimensional representation.

Clause 109: The spatially sensitive augmented reality system of clause 108, wherein the at least one processor is configured to refine the identified one or more physical objects associated with the event.

Clause 110: The spatially sensitive augmented reality system of clause 109, wherein the at least one processor is configured to refine the accuracy or specificity of the identified one or more physical objects associated with the event.

Clause 111: A spatially sensitive augmented reality system for providing resuscitative feedback in a mixed reality environment to an acute care provider during occurrence of a ventilation event in a patient, the system comprising: a wearable augmented reality device having at least one three-dimensional sensor, a visual display for viewing by the acute care provider, and at least one processor configured to: receive and process three-dimensional information of a scene of the ventilation event; produce a three-dimensional representation of a field of view of the acute care provider based on the processed three-dimensional information; identify one or more physical objects associated with the ventilation event in the three-dimensional representation; generate at least one virtual three-dimensional object within the three-dimensional representation; generate an image of the virtual three-dimensional object within the three-dimensional representation on the visual display according to one or more spatially sensitive rules that provides emergency resuscitative guidance to the acute care provider for treating the patient; and manipulate the image of the virtual three-dimensional object within the three-dimensional representation on the visual display as an interaction with the one or more identified physical objects according to the one or more spatially sensitive rules that provides further emergency resuscitative guidance to the acute care provider for treating the patient.

Clause 112: The spatially sensitive augmented reality system of clause 111, wherein the at least one processor is configured to recognize one of the identified physical objects in the three-dimensional representation as a ventilation bag.

Clause 113: The spatially sensitive augmented reality system of clause 112, wherein the virtual three-dimensional object comprises a ventilation indicator that provides feedback representative of a quality with which the acute care provider is administering ventilations to the patient according to whether one or more ventilation parameters are within a desired range.

Clause 114: The spatially sensitive augmented reality system of clause 113, wherein the one or more ventilation parameters comprises at least one of tidal volume, minute volume, ventilation rate, flow rate in the patient's airway, inspiratory flow rate, expiratory flow rate, acute care provider body alignment, and acute care provider fatigue.

Clause 115: The spatially sensitive augmented reality system of any of clauses 111-114, wherein the ventilation event comprises respiratory arrest.

Clause 116: The spatially sensitive augmented reality system of any of clauses 111-115, further comprising an image sensor, wherein the at least one processor is configured to: receive and process image information obtained by the image sensor, recognize an image object within the processed image information, and correlate the recognized image object with the identified one or more physical objects associated with the ventilation event within the three-dimensional representation.

Clause 117: The spatially sensitive augmented reality system of clause 116, wherein the at least one processor is configured to refine the identified one or more physical objects associated with the ventilation event.

Clause 118: The spatially sensitive augmented reality system of clause 117, wherein the at least one processor is configured to refine the accuracy or specificity of the identified one or more physical objects associated with the cardiac event.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only, and are not intended as a definition of the limit of the disclosure.

BRIEF DESCRIPTION OF THE DRAWINGS

FIG. 16A is a perspective view of a tracheal tube for insertion in the patient's mouth which can be used with an augmented reality system according to an aspect of the disclosure;

FIG. 16C is an enlarged view of a portion of the tracheal tube of FIG. 16A;

DETAILED DESCRIPTION

Figure 1:
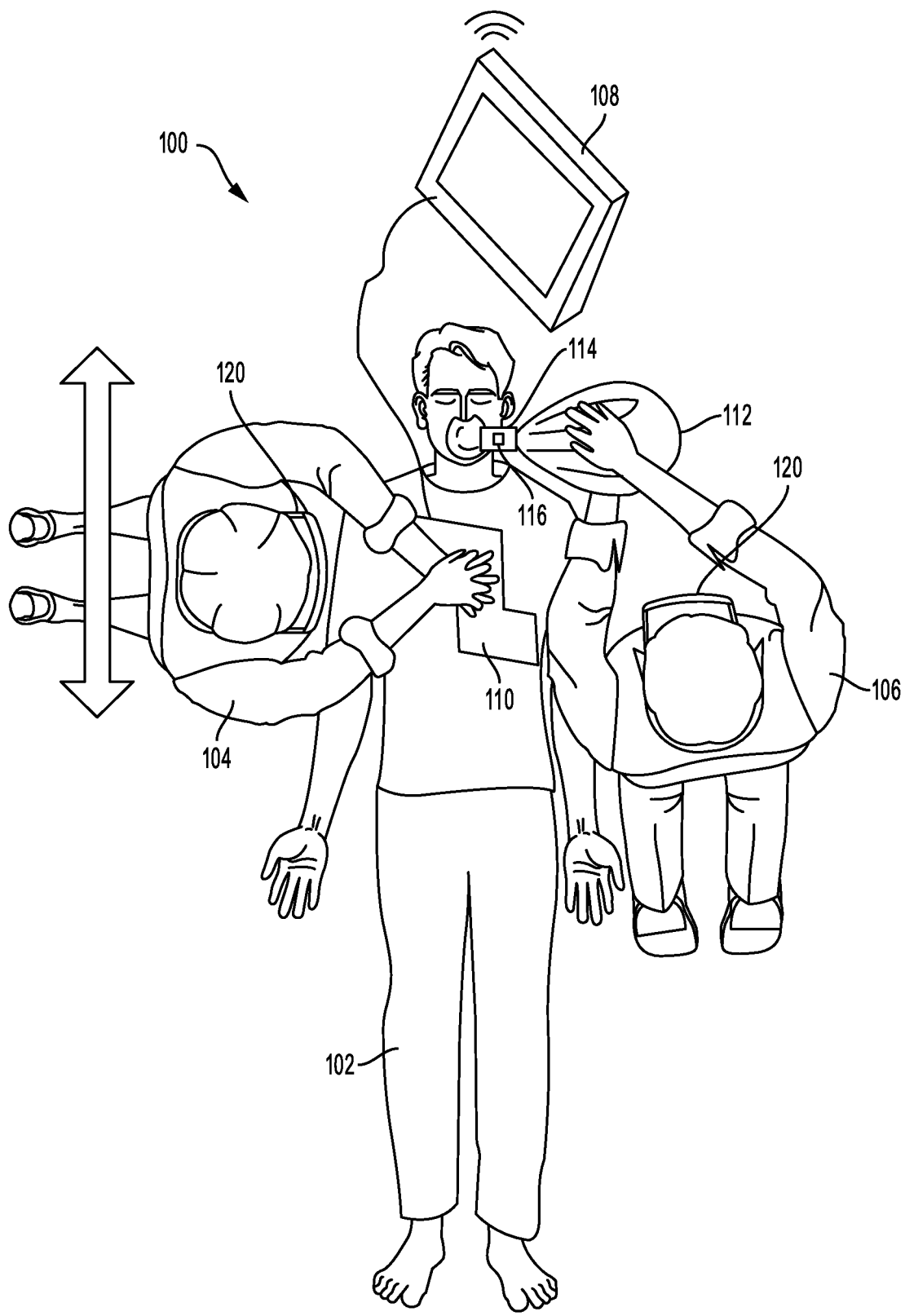
FIG. 1 shows an overhead view of acute care providers wearing augmented reality devices and performing CPR on a patient in accordance with various examples.

As used herein, the singular form of "a", "an", and "the" include plural referents unless the context clearly dictates otherwise.

As used herein, the terms "right", "left", "top", and derivatives thereof shall relate to aspects of the present disclosure as it is oriented in the drawing figures. However, it is to be understood that embodiments of the present disclosure can assume various alternative orientations and, accordingly, such terms are not to be considered as limiting. Also, it is to be understood that embodiments of the present disclosure can assume various alternative variations and stage sequences, except where expressly specified to the contrary. It is also to be understood that the specific devices and processes illustrated in the attached drawings, and described in the following specification, are provided as examples. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

The present disclosure is generally directed to augmented reality devices and systems for providing guidance to medical professionals for use in an emergency medical context. The medical professional can be one or more of acute care providers. "Acute care" can refer to situations in which a patient receives active, but short-term, treatment for an injury, episode of illness, an urgent or emergency medical condition, or during recovery from surgery. An "acute care provider" can refer to any individual, including emergency medical technicians (EMTs), doctors, nurses, and caregivers, who provide short-term care for the patient during such episodes, conditions, or events.

The devices and systems described herein can be used in a variety of environments including, for example, rescue or emergency scenes, ambulances, hospitals, emergency rooms, and out-patient treatment facilities. In some instances, the augmented reality devices and systems can be integrated with existing or newly created electronic systems and databases to, for example, receive information from and automatically update electronic medical records databases, billing systems, inventory systems, and others.

The individual being treated by the medical professional(s) could be an emergency victim at a rescue scene, such as an individual suffering from a physical event or arrest, such as cardiac arrest, respiratory arrest, and/or traumatic arrest. In other examples, the individual could be a hospital patient, such as a patient receiving treatment at an emergency room. In other examples, the individual could be a hospital resident (e.g., an in-patient) who receives treatment on a more regular basis. In other examples, the individual could be an athlete receiving medical advice to improve training or athletic performance, but who is not presently in need of medical treatment. For convenience, any medical professional is described herein as an "acute care provider" and the individual being treated is described herein as a "patient," though it is understood that the "patient" could be an emergency victim, an individual who has suffered trauma but not yet been treated by medical personnel, or any other individual in need of medical treatment or evaluation by medical personnel. The "acute care provider" can refer to individuals that provide treatment for any patient seeking emergency medical assistance, some examples of which are provided herein.

In some examples, the devices and systems described herein can be used by an acute care provider while providing resuscitation activities for a patient at an emergency or rescue scene. In that case, the augmented reality system can comprise a wearable augmented reality device configured to be worn by the acute care provider to assist the acute care provider in performing resuscitation activities. Resuscitation activities can comprise, for example, providing chest compressions, manual or automatic ventilation, monitoring and/or directing the progress of resuscitation performed by others, setting up monitoring and/or therapeutic medical devices (e.g., defibrillator, patient monitor, automated chest compressor, automated/manual ventilator, etc.), administering medications to the patient, monitoring patient vital signs, coordinating transportation of the patient from the rescue scene to a medical facility, coordinating exchange of responsibility for treatment of the patient upon arrival at the medical facility, amongst others.

The devices and systems described herein can also be used by the acute care provider(s) in other tasks, such as record keeping, scheduling, training, and/or reviewing previously provided patient care (e.g., post-event review of recorded patient physiological data or recorded medical events, diagnoses or treatments delivered to the patient, such as found in software programs designed for analysis of entire resuscitation events, for example, Code Review provided by ZOLL Medical, which captures clinical defibrillator information, vital sign information, CPR parameters, and other information, for quality review and analysis).

The augmented reality devices and systems disclosed herein provide guidance and feedback to the acute care provider in a mixed reality environment. For example, the guidance or feedback can comprise emergency resuscitative guidance relevant to a rescue scene and rescue event. For example, as described herein, emergency resuscitative guidance can include information about a physiological condition of a patient, treatment being provided to the patient, and/or resuscitation activities (e.g., chest compressions, ventilations, amongst others) being performed by acute care providers at the rescue scene. A mixed reality environment may refer to an environment including both three-dimensional physical objects and three-dimensional virtual objects (e.g., artificially produced visual indicators, images, and/or holograms) generated by and positioned within the environment by the augmented reality device. For example, the augmented reality device can be configured to generate a three-dimensional representation of the mixed reality environment based on three-dimensional information about the environment gathered from a three-dimensional sensor. The augmented reality device can generate and position, in memory or within space provided by its processor(s), one or more virtual three-dimensional objects within the three dimensional representation based on a position of physical objects in the environment.

Information about the virtual object(s) including a size, shape, structure, and external appearance thereof can be stored in memory associated with the augmented reality device and used to track a position of and manner in which the virtual three-dimensional object interacts with real physical objects within the mixed reality environment. For example, a position and/or orientation of the virtual three-dimensional object(s) can be manipulated in accordance with certain spatially sensitive rules governing the appearance and movement of the virtual object(s). So that the wearer is able to perceive the virtual three-dimensional object(s), the augmented reality device can also be configured to generate and display images of the virtual three-dimensional objects within the acute care provider's field of view on the visual display of the augmented reality device, so that the acute care provider is able to perceive the mixed reality environment comprising images of the virtual three-dimensional object(s) along with the real physical objects including the patient, other rescuers, medical devices, and other objects located at the rescue scene. Desirably, the displayed images of virtual three-dimensional object(s) do not entirely obscure the acute care provider's view of the rescue scene. Instead, when looking through a lens of the augmented reality device, the acute care provider perceives both the images of virtual three-dimensional object(s) projected by the augmented reality device, as well as other, typically all, elements of the rescue scene.

Augmented reality is distinguishable from virtual reality in which a virtual display is projected or provided over a wearer's entire field of view in an immersive manner, such that the viewer does not see any actual or real-life physical objects and only perceives virtual images displayed on the virtual reality device. While virtual reality systems may be useful for certain training and simulation activities, augmented reality systems, which permit a wearer to view actual, real elements of the rescue scene, may be preferable for real-life rescue situations.

The augmented reality devices and systems of the present disclosure may be spatially sensitive devices and systems. For example, the augmented reality devices and systems may be capable of determining locations of physical objects within the three-dimensional representation of the environment by processing three-dimensional information about the rescue scene captured or obtained by three-dimensional sensors of the augmented reality device to track positioning of physical objects at the rescue scene. Based on the positioning of the physical objects, the images of virtual three-dimensional object(s) can be displayed to the acute care provider on the display screen of the augmented reality device according to spatially sensitive rules governing positioning and orientation of the images of the virtual objects relative to physical objects within the acute care provider's field of view. The devices and systems may further be configured to appropriately manipulate displayed images of the virtual objects seen through the augmented reality device according to the spatially sensitive rules depending on how the frame of the reference and/or perspective of the acute care provider has changed (e.g., acute care provider and/or patient has moved). This manipulation of the image displayed on the augmented reality device for the acute care provider to perceive the virtual three-dimensional object may provide additional guidance to the acute care provider for treating the patient. For example, the image(s) displayed on the screen (e.g., displayed on the screen as one or more two-dimensional images, yet appearing to the wearer as the virtual three-dimensional object) may move in relation to the physical objects and the three-dimensional representation. Such manipulation may be effective, for example, to draw the acute care provider's attention to a specific area of the rescue scene, guide a movement of the acute care provider, and/or inform the acute care provider about a status of the patient or medical device at the rescue scene.

Exemplary Rescue Scene

An exemplary use of an augmented reality system during treatment of a patient 102 at a rescue scene 100 is shown in FIG. 1. FIG. 1 illustrates an overhead view of acute care providers 104, 106 performing resuscitation activities (e.g., CPR) on the patient 102. Resuscitation activities performed at the rescue scene 100 can comprise chest compressions and ventilations. The acute care providers 104, 106 are using an electronic system that instructs them in and/or provides feedback about performance of resuscitation activities. The system can comprise augmented reality device(s) 120 worn by one or more of the acute care providers 104, 106. Each of the augmented reality devices 120 can be configured to communicatively interact with each other and/or other medical and computerized devices to manage or provide guidance for treatment for the patient 102 and/or to transmit patient data to another electronic device.

As shown in FIG. 1, the acute care providers 104, 106 are in position and providing care to the patient 102. Acute care provider 104 is providing chest compressions to the torso of the patient 102. Acute care provider 106 is providing ventilation to the patient using ventilation bag 112. The augmented reality devices 120 can provide feedback to the acute care providers 104, 106 related to, for example, one or more of compression depth, compression rate, hand/arm position, ventilation rate, ventilation volume, and other parameters. For example, feedback can be provided by the augmented reality devices 120, such as, in the form of images of a virtual object (e.g., visual indicators) displayed overlaid upon or in relation to physical objects within each acute care provider's field of view. Although two acute care providers 104, 106 are shown here for purposes of explanation, there may only be one acute care provider at a rescue scene or a rescue team could include three or more acute care providers to help care for the patient 102. Additional acute care providers can perform tasks, such as setting up medical devices or monitoring the physiological condition of the patient (e.g., checking patient vital signs). For example, one of the acute care providers can be responsible for setting up a patient monitor or defibrillator 108, while the one or more other acute care providers perform other tasks such as applying chest compressions or bag ventilation. The acute care provider setting up the monitor and/or defibrillator 108 can attach electrodes, which can be contained in an electrode package 110, to the patient 102. Visual feedback provided by the augmented reality device 120 can assist the acute care provider(s) 104, 106 in proper positioning of electrodes and/or electrode package 110. The defibrillator 108 may take a generally common form, and may be a professional style defibrillator, such as the X SERIES, R SERIES, M SERIES, or E SERIES provided by ZOLL Medical Corporation of Chelmsford, Mass., or an automated external defibrillator (AED), including the AED PLUS, or AED PRO from ZOLL Medical Corporation.

In FIG. 1, the electrode package 110 is shown on the patient 102 in a normal position. The electrode package 110, in this example, is an assembly that combines an electrode positioned high on the right side of the patient's torso, a separate electrode positioned low on the left side of the patient's torso, and a sensor package located over the patient's sternum. The electrode package 110, which, in this example, is obscured in the figure by the hands of acute care provider 104 may include a motion sensor, such as an accelerometer, laser interferometer, magnetic induction velocity sensor, or proximity sensor, such as a light or capacitance sensor, which can be configured to transmit data to a portable computer device, rescue management device, or the defibrillator 108 to monitor performance of the chest compressions. In other examples, movement information related to performance of chest compressions can be collected by a separate device resting on the patient's sternum. The device, which may be generally referred to as a CPR puck, often comprises a plastic housing including electronic circuitry and, in particular, the motion and/or proximity sensors.

In some examples, once electrodes (e.g., the electrode package 110) are connected to the patient, the defibrillator 108 can monitor the status of the patient to identify patient physiological events and to determine whether a shockable rhythm is present. A non-exhaustive list of cardiac patient events that can be detected by an external medical device, such as the defibrillator 108, (e.g., via ECG electrodes and an appropriate analysis algorithm) includes, for example: bradycardia, ventricular tachycardia (VT) or ventricular fibrillation (VF), atrial arrhythmias, such as premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventricle arrhythmias, such as premature ventricular contractions (PVCs) and accelerated idioventricular rhythm.

The patient monitor or defibrillator 108 can communicate via wires or wirelessly with the augmented reality device(s) 120 either directly or through another controller or intermediate device, to present information or feedback to the acute care providers 104, 106. For example, the augmented reality device 120 can provide the acute care provider(s) 104, 106 with information about patient condition including, for example, an indication that a shockable rhythm is present. In other examples, actual measurements, such as a real-time ECG trace, can be projected to the acute care provider's field of view.

In some examples, control and coordination of resuscitation activities for the patient can be performed by another type of electronic computerized device, such as a tablet PC, iPad, iPhone, Apple Watch, or other portable computing and display device located at the rescue scene. For instance, the computer device may download and process ECG data from the defibrillator 108, analyze the ECG signals, perform relevant determinations based on the analysis, and control other therapeutic devices. In other examples, the defibrillator 108 can perform all the processing of the ECG, including analyzing the ECG signals, and may transmit only the final determination of the appropriate therapy to a separate device, whereupon the separate device can perform the control actions on the other linked devices.

In some examples, ventilation to the patient is provided by the ventilation bag 112 connected to the patient through an airflow pathway 114 or by a mechanical ventilator. The pathway can include a flow sensor 116 for measuring airflow to the patient and/or exhalation information. In some examples, information obtained by the augmented reality device(s) 120 can be used to assess ventilations provided to the patient in a manner similar to the evaluation of chest compressions discussed herein. For example, the acute care provider can open his or her hand(s) to grasp the bag 112 and can move or rotate his or her hand(s) to force air from the bag 112. The hands and/or wrists return to an initial position when the bag 112 is released, thereby allowing the bag 112 to re-inflate. Ventilation parameters can be measured based on images collected by the augmented reality device 120. Ventilation parameters monitored can comprise tidal volume, minute volume, ventilation rate, flow rate in the patient's airway, inspiratory flow rate, and/or expiratory flow rate. The information about ventilation activities performed by the acute care provider can be used by the device 120 to provide feedback to the acute care provider and, in some cases, to confirm that ventilation activities are appropriately synchronized with other resuscitation activities being formed by other acute care providers.

In some examples, the manual ventilation bag can be replaced by an electromechanical ventilator for providing ventilation to the patient 102. In other examples, ventilations can be performed or initiated by mechanical ventilation devices, such as belts wrapped around the patient's abdomen or a cuirass. The augmented reality device 120 may provide instructions, lists, diagrams, or hand position information to assist the acute care provider in setting up the monitor, defibrillator, and/or the mechanical ventilator.

Augmented Reality Devices

Examples of augmented reality devices 120 that may be used with the systems and methods of the present disclosure include various hands free displays, virtual reality systems, and augmented reality systems including, for example, Google Glass and Microsoft Hololens. The Microsoft Hololens augmented reality device is an example of a device that uses virtual holograms to convey information to a wearer, and which may be incorporated in embodiments of the present disclosure. In some instances, virtual reality systems, such as the Oculus Rift, HTC Vive, and Samsung Gear, can also be used to perform certain aspects of the present invention; however, such virtual reality systems are generally not equipped to allow a viewer to perceive a mixed reality environment that involves manipulation of an image of a virtual three-dimensional object (e.g., holograms) provided within a three-dimensional representation of a visual display as an interaction with identified physical objects (e.g., to view a mixed reality environment) according to spatially sensitive rules.

Figure 2A:
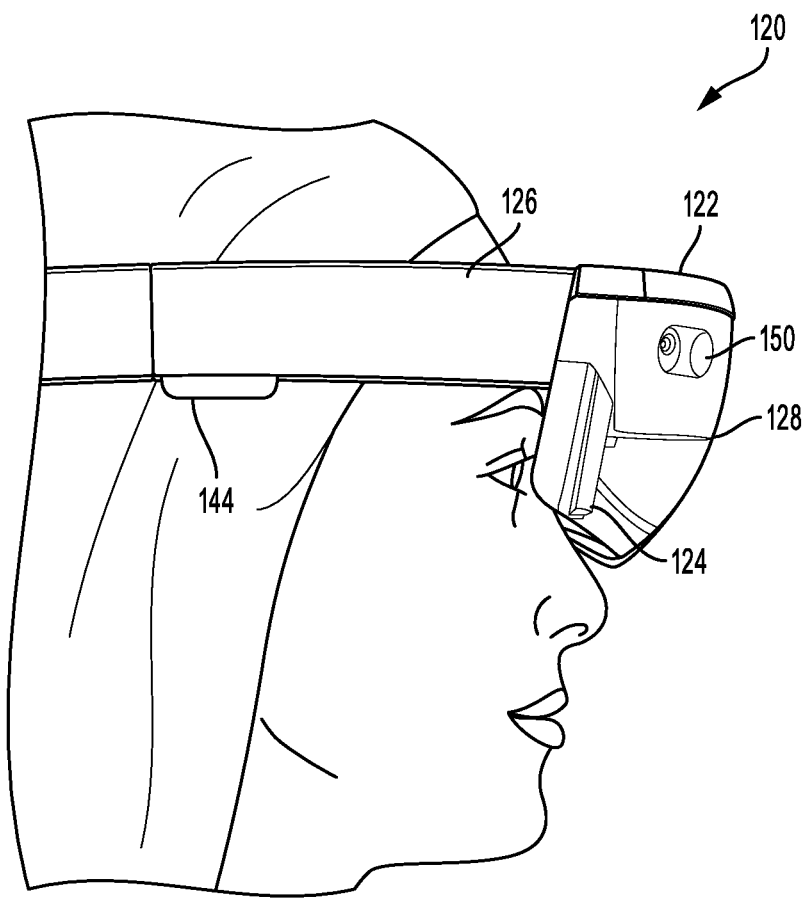
FIG. 2A is a perspective view of an acute care provider wearing an augmented reality device in accordance with various examples.
Figure 2B:
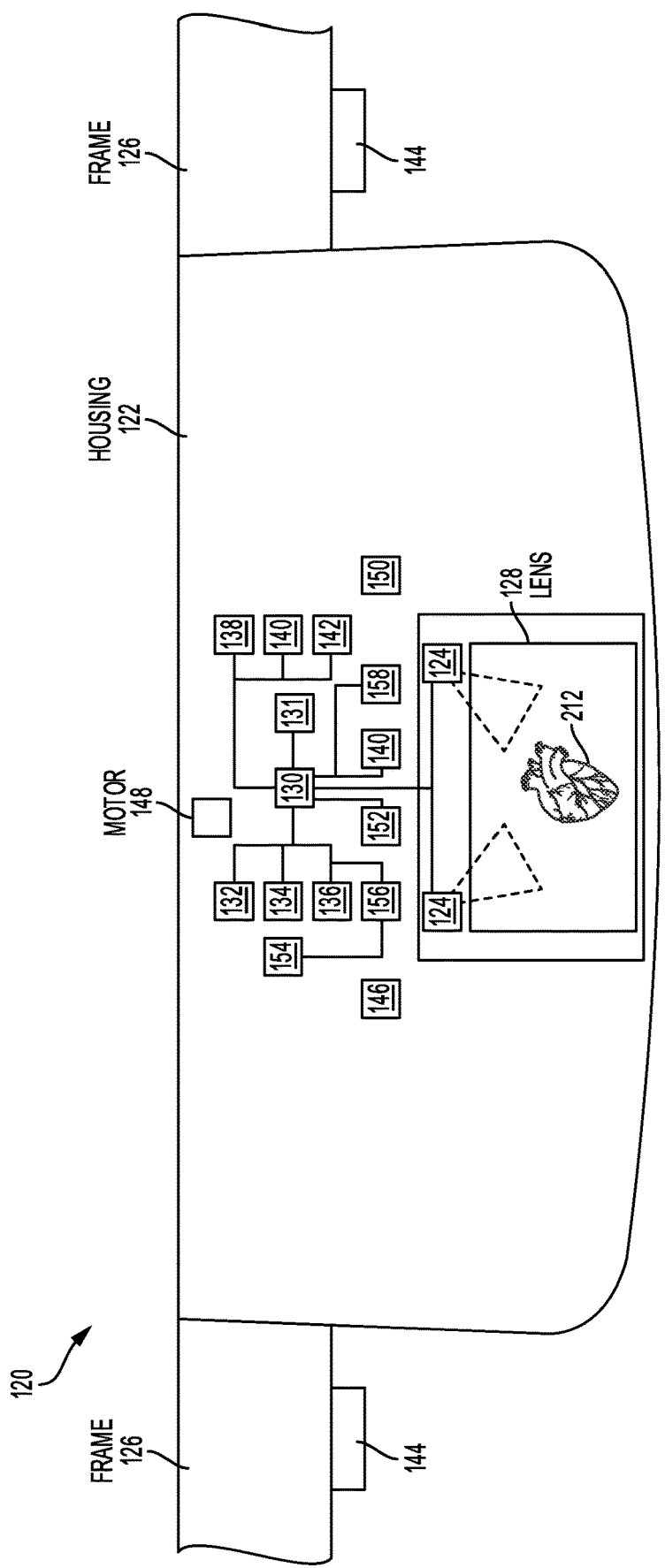
FIG. 2B is a schematic drawing of electronic components of the augmented reality device of FIG. 2A.

With reference to FIGS. 2A and 2B, an augmented reality device (such as device 120) generally comprises a wearable computerized module including processing circuitry for receiving information about a rescue or other medically related scenes and an optical projection element (such as projection device 124 shown in FIG. 2B) positioned to project or display images of virtual objects (e.g., artificially produced visual indicators, images, holograms), within a wearer's field of view to provide information about the rescue effort, resuscitative guidance, and/or other types of resuscitation-related activities by the acute care provider.

In certain embodiments, augmented reality can be particularly effective in providing the acute care provider with information related to the resuscitation effort without detracting or distracting others from the task at hand. For instance, an augmented reality device 120 can provide information about numerous devices and individuals at a rescue scene without obscuring the acute care provider's view of objects in the rescue scene and without requiring the acute care provider to look away from tasks being performed, as would be the case if the acute care provider needed to obtain information from a screen or control panel of a medical device associated with the patient. Further, the information can be displayed in coordination with actual objects in the acute care provider's field of view so that the acute care provider perceives relationships between the identified objects and displayed information. Further, the augmented reality device 120 can allow the acute care provider to manipulate and/or interact with virtual three-dimensional object being displayed by the augmented reality device as an image on the visual display of the augmented reality device. Accordingly, the augmented reality device 120 monitors for and responds to actions performed by the wearer. In contrast, other types of wearable visual feedback devices may merely display information, often in the form of a dashboard or heads up display, but do not identify or respond to changes in the wearer's field of view and/or actions by the wearer. In some examples, part or all of the display viewed by the wearer can be transmitted to other wearers of augmented reality devices at a remote location.

In some examples, the augmented reality device 120 may be configured to provide the wearer with an alert notification for one or more resuscitation activities being performed for the patient or other medical activities needed. For example, the alert notification can comprise an image of a virtual object provided on the screen of the visual display related to a resuscitation activity that is not being performed in an appropriate manner. In some examples, the augmented reality device 120 can be configured to depict images of virtual objects over, or adjacent to, a medical device or portion of the patient's body which is relevant to the notification. For example, if electrodes have fallen off or are not providing a suitable ECG signal, the images of virtual objects can include a flashing indicator positioned overtop of the preferable electrode location or overtop of the actual electrodes, to signal to the acute care provider that the electrodes should be moved to a different (e.g., a preferred) electrode location.

Components of an exemplary augmented reality device 120 are shown in FIGS. 2A and 2B. Specifically, the augmented reality device 120 comprises a housing 122 at least partially enclosing electronic circuitry for receiving and processing information from sensors associated with the device 120 and a visual display, such as the projection device 124, for providing virtual images within a wearer's field of view. The housing 122 can comprise one or more wearable mounting structures 126 comprising, for example, a helmet, visor, hat, frame, pair of glasses, goggles, or a headband. The mounting structure 126 can be adjustable so that the device 120 can be adapted for use by different sized individuals. The housing 122 can be formed from a suitable protective material, such as a hard plastic or metal (e.g., brushed aluminum). The housing 122 may further comprise or be connected to one or more optical lens 128 positioned to cover a wearer's eyes. For example, the device 120 can include a single lens shaped like a lens for a pair of goggles. In other examples, the device 120 can include two separate lens as is the case for a pair of glasses. The housing 122 can be sized and shaped to enclose various electronic elements and devices as discussed herein.

With specific reference to FIG. 2B, the augmented reality device 120 comprises a controller 130, such as one or more computer processors, such as a general purpose processor 132 configured with the functionality described herein, in electronic communication with computer readable memory 131. The memory 131 can include instructions that, when executed by the controller 130, cause the controller 130 to perform functions related to acquisition of data, such as processing of three dimensional information about the rescue scene, producing a three-dimensional representation of the field of view provided by the augmented reality device, generation of one or more virtual three-dimensional objects within a generated three-dimensional representation of the rescue scene, and generate and project images of the virtual three-dimensional object within the acute care provider's field of view. While the virtual three-dimensional object is generated and stored in memory by the augmented reality device, the actual image displayed on the visual display of the augmented reality device may be two-dimensional in nature, yet able to be manipulated in a way such that the image appears as the virtual three-dimensional object within the user's field of view alongside and in interaction with physical objects according to spatially sensitive rules (e.g., as the wearer moves away from the identified physical object, the image of the virtual three-dimensional object presented on the display may get smaller; as the wearer moves toward the identified physical object, the image of the virtual three-dimensional object presented on the display may increase in size; or as the wearer moves his/her head or moves to one side of the identified physical object, the image of the virtual three-dimensional object presented on the display may be modified appropriately). The controller 130 can comprise one or more of the following components: the general-purpose processor 132; a three-dimensional information and/or image processing module 134; a three-dimensional representation generation module 136; a gesture recognition module 138; a communications interface 140, such as a wireless transceiver; and a user interface module 142 in communication with the projection device 124. The controller 130 can also be configured to transmit received data to remote electronic and/or computerized devices and receive instructions from the remote devices. The controller 130 is further configured to execute the instructions to provide information to the acute care provider.

The controller 130 can be configured to receive and process three dimensional information about the rescue scene, for example, to help identify one or more resuscitation activities being performed by the acute care provider. As described herein, the controller 130 may also receive and process two-dimensional images of the rescue scene obtained by digital cameras or image sensors to refine an accuracy or specificity of physical objects identified based on the three dimensional information. For instance, a three-dimensional sensor may provide information about the positioning and size of objects relative to one another, though, images recorded by a digital camera may provide more definitive information for identifying particular objects, such as a defibrillator, patient monitor, electrode pads, rescuer, patient, etc. The controller 130 can also be configured to cause the augmented reality device 120 to provide visual feedback to the acute care providers based on the received and processed images. In some instances, the controller 130 can also be configured to receive information from external sources, such as patient monitoring devices, therapeutic medical devices, and patient physiological sensors located near the patient, as well as from external computing devices, remote computer networks, and computer databases. In some examples, the controller 130 can also be configured to generate code markers, during performance of resuscitation activities, that provide a time-stamped record of a rescue event (e.g., drug infusion/administered, ventilations given, amongst others) for post-rescue event review based on the received and processed images. The controller 130 may further be configured to establish communication with an external device (e.g., defibrillator, monitor, tablet, external computer, etc.) for uploading the code marker thereto and for producing an appropriate summary record of the rescue event.

Projection Device

In some examples, the projection device 124 is configured to emit light beams in a coordinated manner to an inwardly directed surface of the lens 128. The emitted light beams are reflected from the lens 128 to the wearer's eyes, causing the wearer to perceive the images of the virtual three-dimensional objects as if the virtual object is present within the field of view. The projection device 124 can be positioned to project the images on or through the lens 128 to be viewed by the wearer, such that the wearer perceives the images as virtual three-dimensional objects in interactive combination with physical objects in the mixed reality environment. In some examples, the optical lens 128 positioned over the wearer's eyes are configured so that when the projection device 124 is not emitting virtual images, the wearer perceives a substantially unobstructed view of surrounding objects.

In some examples, the viewing frame or field of view provided through the lens 128 of the augmented reality device 120 is limited to a field of view smaller than a wearer's normal field of vision to conserve computing resources. Accordingly, while the wearer may be able to perceive objects located directly in front of him or her, objects which may otherwise be viewable by the wearer's peripheral vision, may be more limited in perception. In some cases, users can be cautioned about the lack of peripheral vision and instructed to turn their heads more often than may be needed when not wearing the augmented reality device. In some cases, the system and device can be made to follow rules regarding how much of the field of view is perceived by the viewer at a given time. For example, the system may be configured to ensure that certain physical objects in the mixed reality environment (e.g., the patient and medical devices which are in use) are viewable at all times. Less important physical objects, such as bystanders, other acute care providers, non-medical items, or medical devices which are not in use may not always be readily viewable through the augmented reality device. Or, in various embodiments, physical objects may be always readily viewable through the augmented reality device.

The augmented reality device 120 can be configured to display images of the virtual three-dimensional objects projected or otherwise provided by the projection device 124 in accordance with and/or to abide by one or more spatially sensitive rules provided to or generated by the device 120. For example, the spatially sensitive rules may comprise instructions linking a position or orientation of physical objects or environmental conditions with types of information to be displayed to the wearer through virtual images. In a similar manner, the instructions may tailor the information displayed by the device 120 to particular activities or actions (e.g., resuscitation activities) performed by the acute care provider wearing the augmented reality device 120. Spatially sensitive rules may further comprise instructions for positioning images of the three-dimensional virtual objects in relation to the physical objects within the acute care provider's field of view. For example, the spatially sensitive rules may require that images of visual objects be projected over (e.g., appear to be on top of) certain physical objects within the wearer's field of view. As discussed herein, the images of the visual objects may further be modified as the physical object(s) or frame of reference of the wearer are manipulated.

Optionally, the projection device 124 is associated with, and controlled by, a user interface module 142. The user interface module 142 can be responsible for applying the spatially sensitive rules for determining what images of virtual objects are provided to the wearer and where such images of the virtual objects are displayed within the wearer's field of view. In other examples, the user interface module 142 can receive instructions about feedback to provide to the acute care provider from other modules of the controller 130 and/or from remote devices and can cause the projection device 124 to display such items to the wearer in accordance with the received instructions.

As described in detail in connection with examples disclosed herein, visual guidance and feedback, including the images of the virtual three-dimensional objects, provided by the projection device 124 and controlled by the user interface module 142 can take many forms including two-dimensional animations, three-dimensional annotations, text, charts, graphs, camera views, and others. In a simple example, the projection device 124 can cause a text instruction, such as displaying the word "Compress," to flash within the acute care provider's field of view to signal to the acute care provider to begin a chest compression. Similarly, displaying "Ventilate" or "Breath" can signal to the acute care provider to perform a manual ventilation. In some examples, visual feedback can be provided to the acute care provider to indicate whether measured values, such as compression rate and depth, are being performed within a predetermined target range. In some examples, feedback can comprise an alpha-numeric character representative of resuscitation activity quality displayed by the projection device 124 within the acute care provider's field of view. Also, audible feedback can be provided by the augmented reality device.

Additional Feedback Components

In some examples, the augmented reality device 120 further comprises additional feedback components to supplement and/or enhance visual feedback projected or displayed within the acute care provider's field of view. For example, the augmented reality device 120 can include speakers 144 for providing audible indicators to the acute care provider and audio input components, such as a microphone 146, for recording speech and/or environment noise. The audio output is intended to supplement or augment sounds normally heard by the acute care provider. Accordingly, the speakers 144 are not "noise cancelling" and may be positioned a distance away from the acute care provider's ears so as not to entirely disrupt the acute care provider's ability to hear sounds (e.g., speech of other acute care providers, audible alerts generated by other devices, environmental sounds, such as sounds indicative of dangerous situations) at the rescue scene. In some instances, the speakers 144 can emit sound in a coordinated manner to create the impression that the sound originated from behind the acute care provider. Volume output by the speakers 144 can be adjusted using the user interface projected within the acute care provider's field of view.

In some examples, the device 120 can be configured to emit a sound through the speaker 144 in the form of a metronome to guide an acute care provider in proper performance of resuscitation activities, such as a rate of applying chest compressions and/or a rate for manual ventilations to a patient. For example, in the case of providing chest compressions to a patient, audio feedback, such as a beep or tick, can be emitted from the speaker 144 when the acute care provider should initiate a chest compression to help the acute care provider to maintain rhythm to provide chest compressions at a desired rate. Sounds emitted from the speakers 144 can also notify the acute care provider of alerts or notifications related to device status, patient status, or information about the rescue effort. For example, an audio alert could issue at a predetermined time to instruct the acute care provider to switch places with another acute care provider or to perform another type of resuscitation activity. Also, verbal commands can be issued to the acute care provider, such as "Check Pulse," "Breath," or for CPR, "Faster" and/or "Slower." In some examples, audio feedback can be provided from medical professional(s) at remote locations for, for example, providing diagnosis or directing treatment.

In some examples, the device 120 can be configured to record the acute care provider's speech with the microphone 146. For example, the acute care provider can be instructed to speak certain phrases that can be recognized by the device 120 related to device function or the rescue effort. The device 120 can be configured to record and process the acute care provider's speech to identify and perform the instructed activity. For example, the acute care provider may speak the phrase "Dashboard display." The recorded voice data may be processed using speech recognition systems known to those of skill in the art, e.g., small vocabulary, speaker independent speech recognition or online speech recognition, such as provided by Amazon Transcribe, Automatic Speech Recognition, or Google Cloud Speech API. In response, based on the text generated by the speech recognition system, the user interface module 142 can parse the text, e.g., "Show Dashboard. Show ECG. Show CPR. Smaller. Smaller. Move upper right.", and cause a dashboard display to be projected within the acute care provider's field of view including information about the patient and rescue effort, according to the commands uttered or otherwise provided via an alternative input. In the particular example above, first, a dashboard is displayed in the acute care provider's field of view. Then, based on the additionally parsed commands, ECG is added to the dashboard. Next, CPR performance data is added to the dashboard display. Then an overall size of the dashboard is reduced two times. Then the dashboard is moved to the upper right of the field of view. It can be appreciated that other combinations of commands may be input to the device and performed.

With continued reference to FIG. 2B, in some examples, the augmented reality device 120 can also provide vibration feedback to the acute care provider. For example, a vibration motor 148 may be embedded within the housing 122 and configured to emit various patterns and intensities of vibration to convey information to the acute care provider. The vibration motor 148 can be a compact linear actuator that vibrates at varying patterns and intensities as directed by the controller 130. Such an actuator may include a spring and magnet for manipulating a mass coupled thereto.

In one example, vibration may be provided to direct the acute care provider to move in a certain way. For example, a vibration felt on one side of the acute care provider's head may signal to the acute care provider to turn his/her head in that direction. Other vibration patterns or intensities may signal to the acute care provider to focus or gaze at a specific virtual image or physical object within his/her field of view. In some instances, providing vibration feedback, rather than audio alerts or visual indicators, may be less likely to distract other acute care providers from resuscitation activities they are performing. Accordingly, vibration feedback can be well-suited for providing certain less important information to the acute care provider during performance of resuscitation activities.

In some examples, vibration feedback can be used to guide performance of resuscitation activities by the user and/or to provide information to the acute care provider about the quality and/or accuracy of resuscitation activities being performed on the patient. For example, vibration feedback can be provided for performance of chest compressions or manual ventilation to the patient. The feedback can be periodic or aperiodic and provided to instruct the acute care provider in the manner in which compressions or ventilations are given. Similarly, vibration feedback can be provided both when the acute care provider should begin a compression or ventilation and when the acute care provider should release the compression or ventilation. Accordingly, vibration feedback can be a supplement to, or replacement for, the audible metronome emitted from the speakers 144.

In some examples, vibration feedback can also be provided by separate components or devices in communication with the augmented reality device 120. For example, the acute care provider may wear a wristband, watch, bracelet, or similar device (not shown) comprising a linear actuator motor configured to vibrate at variable patterns and intensities to convey information to the wearer. The augmented reality device 120 can be configured to cause the separate vibration feedback device to vibrate in a coordinated manner with images of a virtual object projected by the augmented reality device 120. For example, the separate vibration device may vibrate to indicate to the acute care provider when to begin and release a chest compression, ventilation bag compression, or similar action.

Communications Components

The augmented reality device 120 can further comprise a communications interface 140, which can include short range or long range data communications features, such as a wireless data transceiver, for wireless communication between the augmented reality device 120 and other electronic devices located at, or remote from, the rescue scene. For example, the augmented reality device 120 can be in communication with one or more of a mobile computing device, e.g. iPad, iPhone, Apple Watch, smartphone, computer, or tabletPC by a wireless data transmitter or transceiver, such as a transceiver using the Bluetooth®, Zigbee, or 802.11 data transmission protocol. In some embodiments, the augmented reality device 120 can also be in communication with a computing or medical device associated with a patient. The patient associated devices can be configured to provide information such as, for example, personal identification information of the patient, estimated location of the patient, recent patient movement (or lack of movement) information, estimated time period in which the patient has been incapacitated and/or immobile, medical history information of the patient, physiological event information of the patient, etc. In other embodiments, the augmented reality device 120 may be configured to receive information from a defibrillator device at the rescue scene including sensing electrodes for monitoring, for example, patient ECG. The augmented reality device 120 may also receive information about a status of the defibrillator, such as whether the defibrillator is ready to provide a shock to the patient. In some examples, data collected by the augmented reality device 120, including images captured by the cameras 150, can be transmitted from the augmented reality device 120 to other electronic devices at the rescue scene, such as the smartphone or computer. Data received by the computing devices can be processed and transmitted to other devices remote from the rescue scene by, for example, a long-range transceiver (e.g., a cellular or Wi-Fi transceiver) integrated with the smartphone.

The communications interface 140 can be configured to communicate with other devices, such as the defibrillator 108 (shown in FIG. 1). The communications interface 140 can also be configured to transmit information about the patient, acute care provider, or rescue scene obtained from sensors and other electronic components of the device 120 to remote devices, locations, or individuals. The communications interface 140 can also be configured to receive information, such as instructions to provide feedback to the acute care provider, from other computerized and/or medical devices at the rescue scene. In some examples, the augmented reality device 120 can be in communication with other devices (e.g., medical device, defibrillator, patient monitor, sensors, communications device, smartwatch, wearable device, etc.) connected to, or associated with, the acute care provider to form a personal area network (PAN). Information and instructions can be shared between the different devices so that feedback can be provided to the acute care provider in the most effective manner. In some examples, the augmented reality device 120 can serve as a front end (e.g., a remote display) for a separate medical device, system, or network. For example, the augmented reality device 120 can be configured to display information generated by a medical device, such as a patient monitor or defibrillator 108, to inform the acute care provider about the status of the device or defibrillator 108.

In some examples, the communications interface 140 can be configured to transmit data to an intermediate device having long-range data transmission capabilities. The intermediate device (e.g., a smartphone, tablet, laptop computer, or PDA) can receive and, in some cases, perform additional processing on the received data. The data can then be transmitted to an external electronic device, computer network, or database using the long-range data transmission capabilities of the intermediate device.

In some further examples, the communications interface 140 can comprise circuitry for long-range data transmission directly from the device 120 itself. Long-range data transmission can be performed by a long-range data transmitter or transceiver, for example a WiFi transmitter or a cellular transmitter (e.g., 3G or 4G enabled systems). Data collected by the device 120 can be sent to external sources by the long-range data transmitter or transceiver.

Three-Dimensional Sensors and Cameras

In some examples, the augmented reality device 120 further comprises one or more optical sensors 150, such as three-dimensional sensors for obtaining three-dimensional information about the rescue scene and/or cameras for capturing still or moving two-dimensional images of the rescue scene. Three-dimensional information can include distance or depth information about how far away physical objects are from the sensor, as well as their size/dimensions. Three-dimensional information and/or images from the optical sensors 150 of one or more augmented reality devices 120 can be processed to produce a three-dimensional representation of the rescue scene. The three-dimensional representation can be useful for the identification of the physical objects present at the rescue scene including, for example, acute care providers, patients, bystanders, therapeutic medical devices, monitoring devices, medical supplies, as well as environmental objects, such as a street or driveway, trees, buildings, power lines, automobiles, trucks, trains, and other objects, which may impact how and where treatment is provided to a patient. As also discussed herein, other information such as captured images/video may be further used to identify physical objects present at the rescue scene.

In some examples, the optical sensors 150 comprise devices having both optical and depth (e.g., three-dimensional) sensing components, such as with the Kinect motion sensing input device by Microsoft, the Intel RealSense D415 camera, or the Apple TrueDepth 3D sensing system employing vertical-cavity surface emitting lasers (VCSELs) such as those provided by Finisar (Sunnyvale, Calif.). The Apple TrueDepth 3D sensing system may further comprise an infrared camera, flood illuminator, proximity sensor, ambient light sensor, speaker, microphone, 7-megapixel traditional camera, and/or dot or grid projector (which projects into the field of view as many as 30,000 dots or comparably dense grid during a scan in order to effectively track real 3D objects that are detected in the field of view).

Cameras for capturing images of the rescue scene can include one or more of a digital camera, RGB camera, digital video camera, red-green-blue sensor, and/or depth sensor for capturing visual information and static or video images of the rescue scene. The cameras can be positioned to substantially correspond to the acute care provider's field of view. The augmented reality device 120 can include multiple cameras, such as a camera positioned adjacent to each of the acute care provider's eyes to generate a stereo-image, which substantially corresponds to the acute care provider's field of view. The stereo-image can be processed to determine depth information for objects in the rescue scene. Other cameras may face to the side (e.g., to the right or left of the acute care provider's field of view) to, for example, capture a 180 degree or larger view of the rescue scene. Another camera may obtain images of the acute care provider's eyes to detect, for example, when the acute care provider's gaze changes direction and/or moves from one object to a different object.

Although designs differ from different vendors, as is known in the art, a camera usually comprises a charge-coupled device (CCD) or complementary metal-oxide-semiconductor (CMOS) imaging sensor, a lens, a multifunctional video control chip, and a set of discrete components (e.g., capacitor, resistors, and connectors). An image is recorded by the imaging sensor and can be processed by the video control chip. The processed image can be provided to the three-dimensional information and/or image processing module 134 of the controller 130 for further processing and to identify physical objects contained in the captured images. The processing module 134 may also prepare certain images for transmission from the device 120 to other electronic devices by the communications interface 140. In some examples, images can be transmitted to the remote electronic device in substantially real-time. In other examples, obtained images can be stored locally on the augmented reality device 120, for example in the computer readable memory 131 associated with the controller 130. The stored images can be transmitted by the communications interface 140 to the remote electronic device as a batch download at predetermined intervals.

In some examples, three-dimensional information and images captured by the optical sensors 150 can be used to identify movement of the acute care provider or patient. The three-dimensional information and/or images can also be used to identify physical objects at the rescue scene, such as other acute care providers, patients, or medical devices, within the acute care provider's field of view. Identification of objects can be used, for example, to assess potential dangers at the rescue scene and/or to assist in a determination of what types of medical devices could be required to treat the patient. Examples of uses for cameras in emergency rescue are disclosed, for example, in United States Patent Publication No. 2014/0342331, entitled "Cameras for Emergency Rescue," which is assigned to the assignee of the present application and is hereby incorporated by reference in its entirety.

With continued reference to FIG. 2B, the three-dimensional information and/or image processing module 134 of the controller 130 can be configured to perform certain processing routines on the collected three-dimensional information and images. Such processing techniques may be used for assisting with operation of the augmented reality device 120 and, in particular, to assist with positioning and/or movement of images of virtual objects as the acute care provider changes position. While the following processing routines are described as being performed by the three-dimensional information and/or image processing module 134 of the controller 130, it is understood that any or all of these processes can be performed by a remote computerized device. In that case, the device 120 can be configured to transmit obtained images to the remote electronic device through the communications interface 140. The remote electronic device can be configured to transmit information about location of objects in the rescue scene and feedback to be provided to the acute care provider back to the augmented reality device 120, so that the feedback can be provided to the acute care provider by the projection device 124.

In some examples, the controller 130 and associated circuitry can be configured to process three-dimensional information and images received from the optical sensor(s) 150 to generate the three-dimensional representation of the rescue scene. For example, the three-dimensional representation and images for different views of the rescue scene can be arranged to derive a 360 degree representation of the rescue scene. The three-dimensional information and captured images can also be compared to determine where certain physical objects are located within the rescue scene, their relative size/dimensions, and/or to determine distances between physical objects of particular interest. For example, three-dimensional information may indicate that a physical object about the size of a medical device is present at a particular position in the generated three-dimensional representation. The captured image may provide additional information about the medical device, such as a device type, manufacturer, or exact dimensions. Additionally, three-dimensional information could be used to track positioning or movement of objects to determine resuscitation activity parameters, assign various roles of a treatment protocol to different acute care providers, and to assist in performance of different aspects of the rescue effort.

In some instances, the types of physical objects identified in captured images can be used to identify resuscitation activities being performed by the acute care provider. For example, if the three-dimensional information and/or captured images show the acute care provider's hands placed against the patient's chest, it may be determined that the acute care provider is providing chest compressions. In some instances, the types and locations of physical objects identified in the captured images can be also used to determine where within the field of view of the acute care provider, particular images of a virtual object (e.g., visual indicators) should be displayed. For example, the previously described beating heart icon may be displayed over top of (e.g., appearing to overlay) related objects. In some instances, the icons may appear to be partially transparent or see-through, so that the user can perceive the actual object below the projected icon. In another example, during performance of chest compressions, an image of a virtual object of a correct or target hand position can be overlaid on the acute care provider's actual hands, so that the acute care provider can appreciate differences between his/her actual hand position and a target hand position.

In some examples, the controller 130 can also be configured to apply spatially sensitive rules for generated virtual objects in the three-dimensional representation based on a position of identified physical objects. As described herein, spatially sensitive rules provide a contextual basis for displaying images of the virtual object to the acute care provider. For example, the controller 130 may identify a position of the patient in captured images. Any images of virtual objects displayed on the visual display of the augmented reality device in the acute care provider's field of view could be positioned so as not to obscure the view of the patient. Other images of virtual objects may be projected on the visual display of the augmented reality device to appear to rest on the patient. For example, a performance indicator icon for the patient may be displayed as resting on the patient's chest. The controller 130 can be configured to apply a variety of known image processing algorithms for identifying objects in captured images including based on color (e.g., pixel color) of certain portions of captured images. In other examples, shape recognition algorithms can be applied to captured images to identify shapes of different objects. For example, the controller 130 can recognize an acute care provider's hand based on a combination of recognition of skin tones in the captured image and identification of shapes of the fingers and palm in the captured image.

In some examples, signals received by the augmented reality device 120 from other devices at the rescue scene can help to confirm and/or improve the accuracy of image processing techniques. For example, if the communications interface 140 receives patient physiological information from a defibrillator 108 (shown in FIG. 1) connected to the patient, then the controller 130 may be configured to review images including the patient to attempt to identify the actual location of the defibrillator 108. In some cases, the communication interface 140 can be configured to identify a direction and/or intensity of wirelessly received signals. Direction and intensity information can be processed to estimate a location of the device that transmitted the received signal. The controller 130 can be configured to process recorded images to confirm the estimated location of the device. Once particular objects are identified, the controller 130 can be configured to adjust the position of certain visual indicators displayed by the projection device 124 to correspond with the location of the identified objects. For example, as discussed herein, certain images presented on the visual display for representing a virtual object may be overlaid (e.g., positioned over top of) on physical objects within the acute care provider's field of view.

With continued reference to FIG. 2B, in some examples, the gesture recognition module 138 of the controller 130 can be configured to identify the acute care provider's hands within images obtained by the augmented reality device 120 and, based on the position, orientation, and movement of the hands, can identify gestures performed by the acute care provider for the purpose of controlling operation of the device 120 and/or for manipulating the user interface and/or dashboard displays provided to the acute care provider by the projection device 124. A gesture can be a predetermined coordinated movement performed by the acute care provider. For example, the acute care provider could perform a gesture to signify what type of resuscitation activity he or she is performing or will perform (e.g., turning palms downward and mimicking a pushing motion can represent a chest compression, turning wrist upward in a manner that signifies compressing a ventilation bag). Other gestures can be used to identify a particular acute care provider or the patient. For example, an acute care provider can perform a predetermined gesture to identify himself or herself, thereby allowing the device 120 or an external device in communication with the augmented reality device 120 to associate the device 120 with a particular acute care provider. In other examples, gestures can be used to interact with the user interface of the device 120. For example, certain pre-programmed gestures can be used to scroll through information displayed by the projection device 124 or to toggle through different screens of the user interface.

Movement Sensors

The augmented reality device 120 may further comprise a number of sensors (e.g., motion sensors, accelerometers, light sensors, capacitive sensors, proximity sensors, etc.) for measuring additional information about the wearer's field of view and the surrounding environment. For example, a movement and/or motion sensors 152 of the augmented reality device 120 can be used to provide additional information regarding the field of view, such as determine when the acute care provider's position and/or field of view changes (e.g., when the acute care provider moves his or her head or to identify detected physical objects in the field of view). When the acute care provider's head position changes, the position of images presented on the visual display of the augmented reality device of a virtual three-dimensional object (e.g., displayed by the projection device 124) may need to be adjusted so that the relationship between particular actual objects viewed by the acute care provider and the images of a virtual object are maintained. That is, the perception of the images of a virtual three-dimensional object may be such that they behave as if they are a part of the real world.

In some examples, the motion sensor 152 can be a single axis or multi-axis accelerometer. Single axis accelerometers can be used to identify acceleration of the augmented reality device 120. Acceleration data can be integrated to provide velocity information, and integrated again to provide displacement information. Multi-axis accelerometers, e.g., a three-axis accelerometer, can provide signals that further determine relative orientation of their respective electrode assemblies by measuring parameters indicative of motion along each axis, in addition to determining velocity and displacement. The motion sensors 152 can also include a gyroscope for determining orientation of the sensor by way of tilt or rotation.

Environmental Sensors

The augmented reality device 120 can further comprise environmental sensors. Information from other environmental sensors, such as temperature sensors, humidity sensors, barometer, air quality sensors, chemical sensors, light sensors, decibel sensors, location sensors (e.g., a GPS sensor), and the like may be used to determine additional information about the environment and/or rescue scene. The environmental sensors 154 can be coupled to and/or associated with a sensor interface 156. The sensor interface 156 can be configured to collect information received from the multiple sensors, perform initial processing for the received information, and provide the information to the controller 130. The controller 130 can cause the sensor information to be collected and transmitted to the remote electronic device by the communications interface 140.

Timer and Internal Clock

In some examples, the augmented reality device 120 further comprises electronic circuitry, such as an electronic clock or timer 158, for tracking passage of time (e.g., during a resuscitation activity) and/or for determining a current time. The timer 158 can be enclosed within the housing 122 and in communication with the controller 130. The timer 158 can be configured to communicate with an external electronic device, such as a smartphone or PDA, or external computer network to determine a current time. The current time can be displayed within the acute care provider's field of view by the projection device 124. In addition, the current time can be automatically associated with data received from the sensors of the device 120 to provide a timestamped record of events at the rescue scene. Timestamps can be used to correlate the received data obtained by the device 120 with data recorded from other devices, such as the defibrillator 108 (shown in FIG. 1). The time-stamped data can also be correlated with data obtained from other devices at the rescue scene to provide a time-stamped record of multiple resuscitation activities being performed for the patient. The timer 158 can also be used to determine a duration of certain events during the rescue. For example, the timer 158 can measure an amount of time from occurrence of a physiological event, such as an elapsed time in which treatment was provided to the patient. Also, timing information from the timer 158 can be used to guide when scheduled treatment events should be provided. For example, a treatment protocol may include administering a particular medication to the patient at specific time intervals, or different medications at specific time intervals. The timer 158 can automatically track a period of time from administration of the medication, and provide a notification when the next dose should be provided. In a similar manner, the timer 158 can track the time that has elapsed as a resuscitation activity, such as chest compressions or ventilations are being performed. Accordingly, based at least in part on the time of events, the device 120 may provide the user with an indication of which activity should be performed at any given time.

Mixed Reality Environment

Having described components of the augmented reality device 120, interactions between the augmented reality device 120 and the mixed reality environment will now be further described. As discussed above, the mixed reality environment includes both physical objects at the rescue scene, such as a patient 202, acute care providers 204, 206, or a defibrillator 208 (shown in FIG. 2E), and virtual three-dimensional objects generated by the augmented reality device 120. The acute care provider views the mixed reality environment through the augmented reality device 120, which displays images of the virtual three-dimensional object within the acute care provider's field of view 220, 230.

Figure 2C:
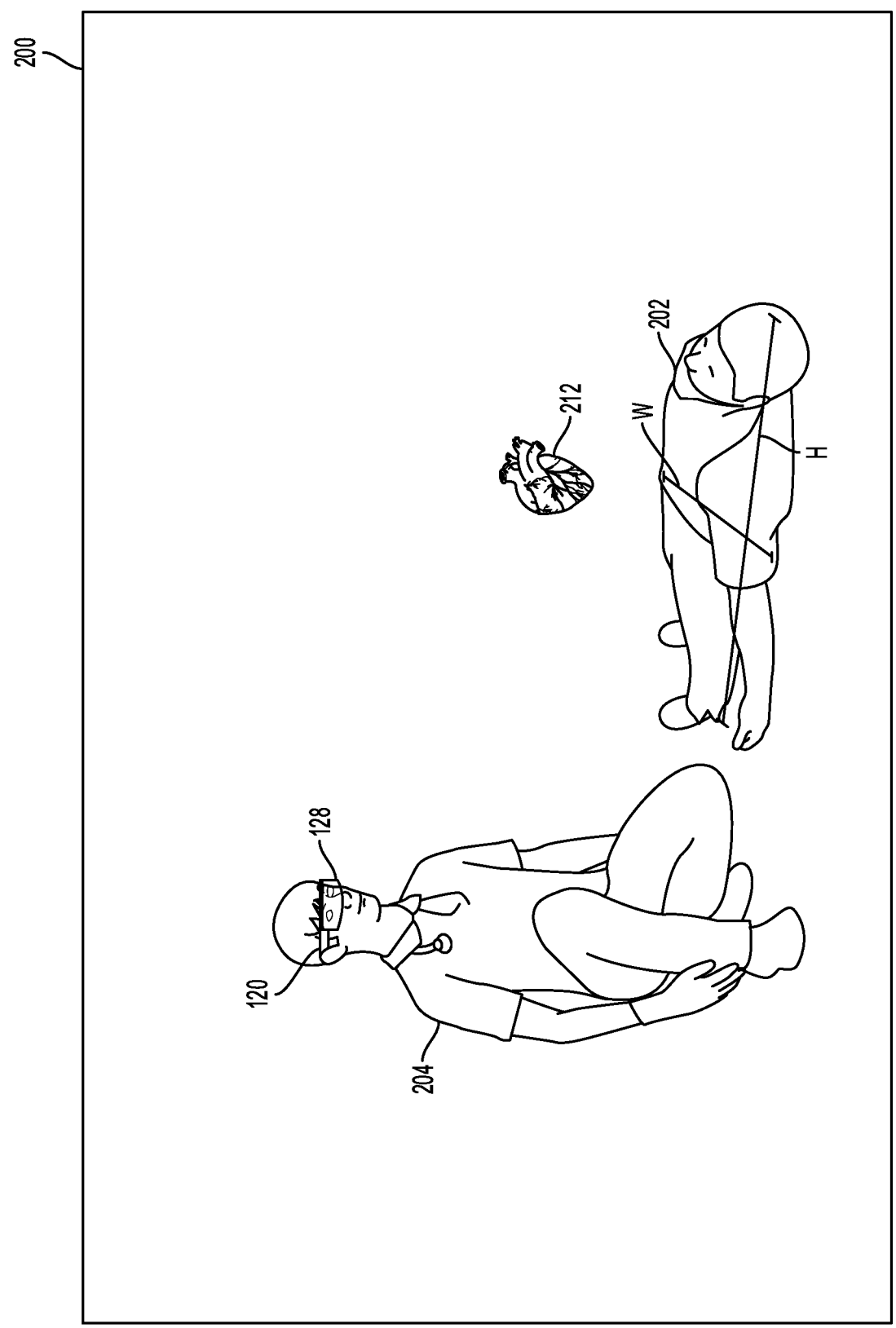
FIG. 2C is a drawing of an exemplary three-dimensional representation of a rescue scene including an acute care provider wearing the augmented reality device of FIG. 2A and a virtual three-dimensional object.

An example of a virtual three-dimensional object which can be positioned in the mixed reality environment is the image of a heart 212 shown in FIGS. 2B-2E. In FIG. 2B, a two-dimensional image of the heart 212 is displayed on the lens 128 of the augmented reality device 120. When viewing the rescue scene through the lens 128, the acute care provider perceives both physical objects at the rescue scene and the virtual three-dimensional object(s) (via the two-dimensional image presented on the visual display) of the mixed reality environment, such as the heart image 212, at the same time. While the heart image 212 displayed on the lens 128 is two-dimensional, it is positioned on the lens 128 so as to appear to interact with physical objects in the mixed reality environment. The heart image 212 can be a performance indicator which provides information about a physiological status of the patient 202, such as heart rate or estimated amount of blood perfusion. For example, the heart image 212 can be configured to expand and contract to show a patient's heart rate or in response to a chest compression to indicate that blood is being moved through the patient's vasculature by the chest compression. One feature of a mixed reality environment is that a position and orientation of the virtual three-dimensional object(s), such as the heart image 212, can change over the course of the rescue effort according to the spatially sensitive rules for the mixed reality environment. For example, in some instances, the heart image 212 may be positioned resting on a patient's chest. At other times during the rescue effort, the heart image 212 can be optionally repositioned (e.g., displayed near other portions of the patient's body) if, for example, the acute care provider needs to be able to see physical objects in the patient's cardiothoracic region to perform certain treatments and resuscitation activities, as depicted in FIG. 2C. In some embodiments, the wearer of the augmented reality device may reposition the virtual object (e.g., represented by the heart image 212) by gestural interaction (e.g., grabbing the space occupied by the virtual object in the three-dimensional representation as if the virtual object were actually there and effectively moving the virtual object to another location). Additionally, the images representing the virtual three-dimensional object(s) displayed to the acute care provider may need to be manipulated or repositioned, for example, as the acute care provider changes position during the rescue effort since, as the acute care provider changes position, different portions of the virtual three-dimensional object(s) may be visible.

In order to track a position of physical objects at the rescue scene and to determine which images of the virtual object(s) should be displayed through the augmented reality device 120, the augmented reality device 120 is configured to generate a three-dimensional representation 200 of the rescue scene, an example of which is shown schematically in FIG. 2C. In this embodiment, the three-dimensional representation 200 includes the physical objects, such as the acute care provider 204 wearing the augmented reality device 120 and the patient 202. The patient 202 is positioned on the ground in close proximity to the rescuer 204. The patient 202 can be identified by the augmented reality device 120 using a combination of three-dimensional information collected by three-dimensional sensors and images captured by cameras of the augmented reality device. For example, the three-dimensional information may identify a human-sized object (e.g., an object having a height H of from 5 ft. to 7 ft., and a width W of about 1 ft. to 2 ft.) on the ground in proximity to the acute care provider 204. Images of the rescue scene can be used to further refine a shape and appearance of the patient 202 to provide a greater level of certainty of the identification. For example, as shown in FIG. 2C, the representation of the patient 204 could be refined to include facial features, clothing, and other identifying characteristics. As shown in FIG. 2C, the virtual three-dimensional object of the heart, represented on the visual display as the heart image 212, is positioned in the three-dimensional representation 200 above a chest 214 of the patient 204.

Figure 2D:
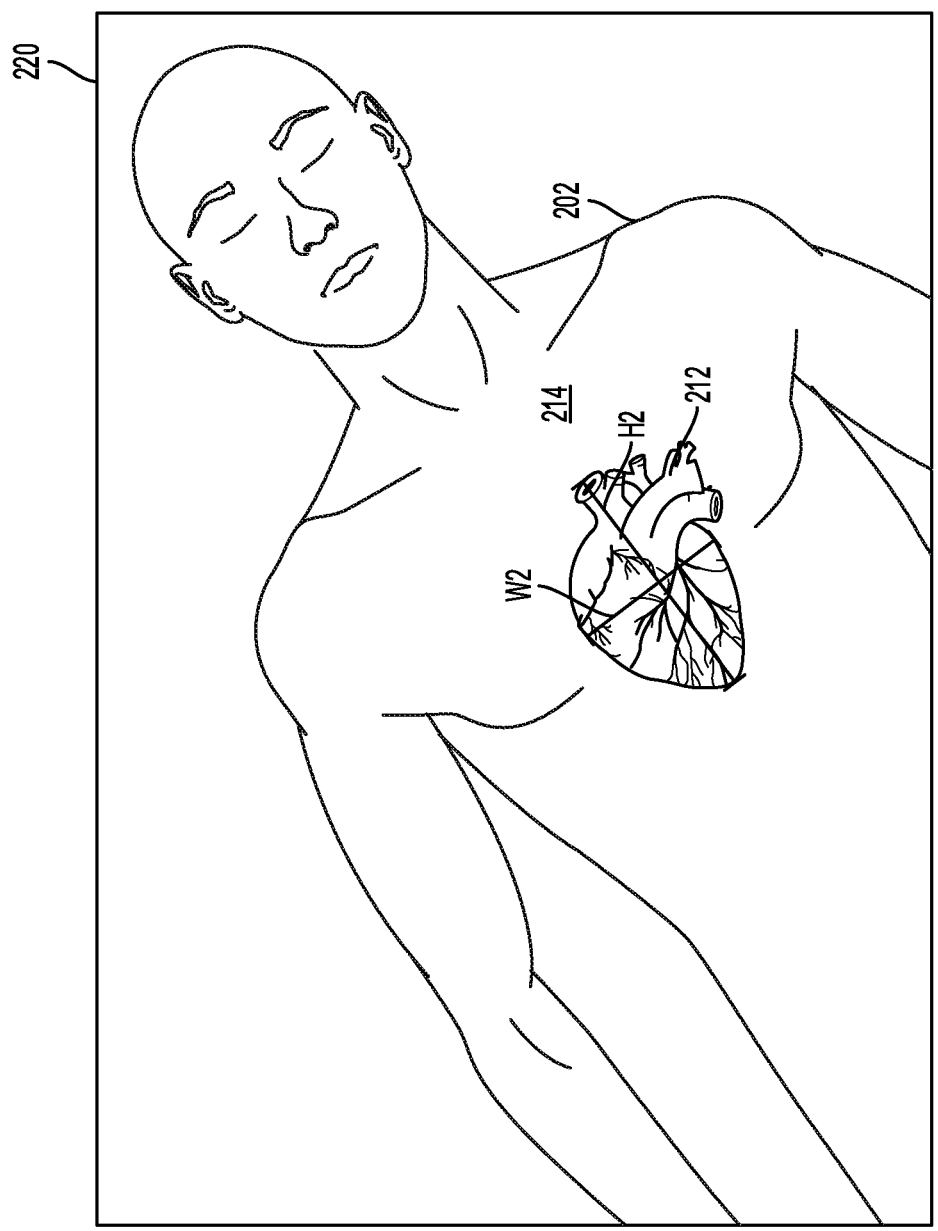
FIG. 2D shows an exemplary field of view of the acute care provider of FIG. 2C including a patient and an image provided on the display of the augmented reality device of the virtual three-dimensional object positioned at a location of the patient.

As described above, the acute care provider views the mixed reality environment through the augmented reality device 120. In particular, two-dimensional images of the virtual object(s), such as the heart image 212, are displayed to the acute care provider based on a position of the virtual three-dimensional object in the three-dimensional representation of the rescue scene. For example, a field of view 220 of the acute care provider when the acute care provider is in close proximity to the patient 204, is shown in FIG. 2D. For example, the acute care provider may be kneeling or crouching down and leaning over the patient's chest 214. As shown in FIG. 2D, the heart image 212 appears to be rather large, having a height H2 and a width W2. The heart image 212 in FIG. 2D appears to cover a substantial portion of the central area of the field of view 212. Such an image provides a representation that the virtual three-dimensional object of the heart is closer to the wearer.

Figure 2E:
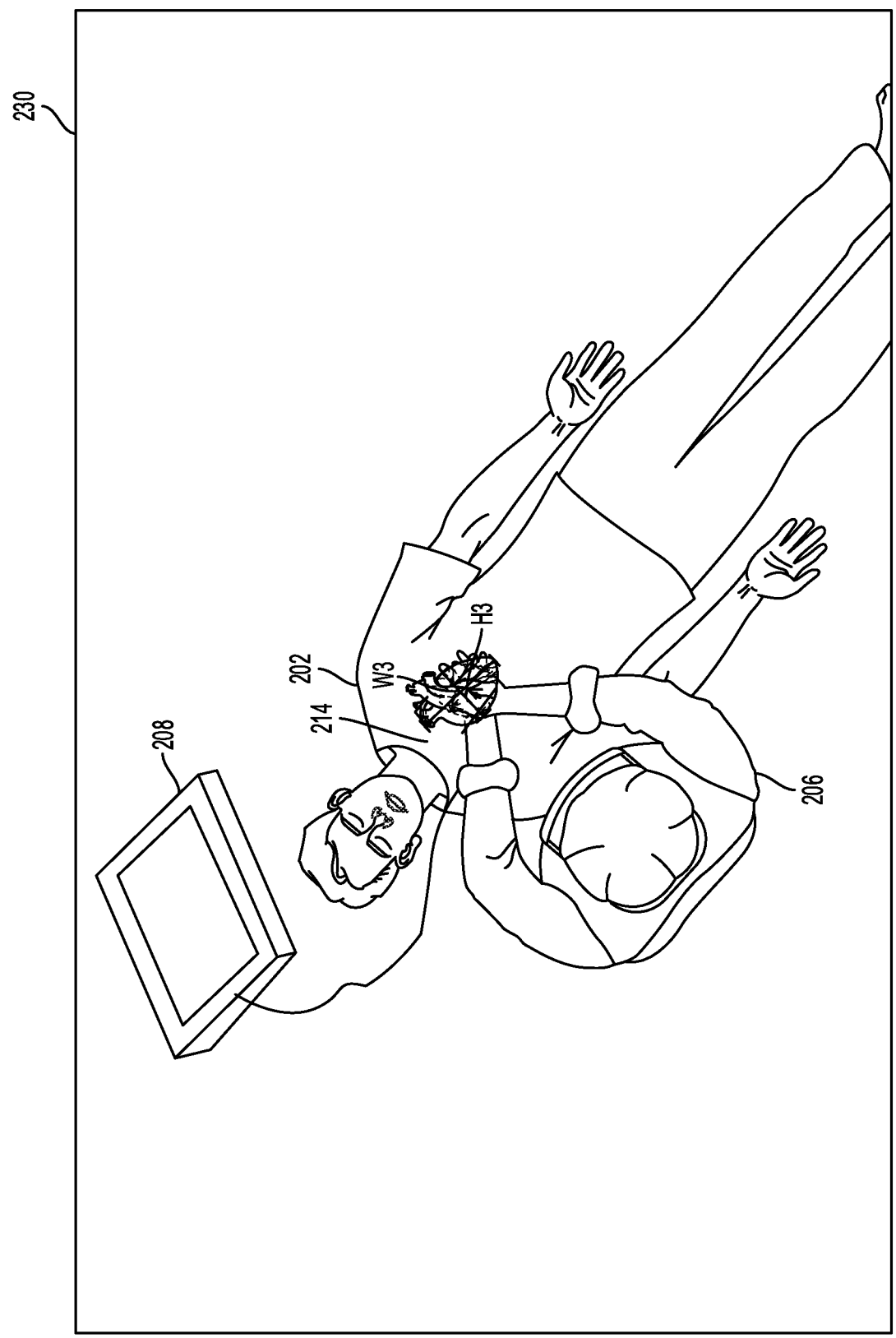
FIG. 2E shows another exemplary field of view of the acute care provider of FIG. 2C from a different perspective than in FIG. 2D.

As shown in FIG. 2E, a field of view 230 for an acute care provider who has stood up and stepped away from the patient 202 is shown. In the field of view 230, the heart image 212 appears to be smaller, having a height H3 and a width W3 about half of the height H2 and width W2 in FIG. 2D, since the acute care provider is farther away from the patient 202. In contrast to the image shown in FIG. 2D, this image provides a representation that the virtual three-dimensional object of the heart is further away from the wearer. In addition, other physical objects in the rescue scene such as another rescuer 206 and a defibrillator 208 are visible, when the field of view 230 includes a larger portion of the rescue scene. In FIG. 2E, a position of the heart image 212 is also changed from FIG. 2D. For example, the heart image 212 is shown over hands 216 of the acute care provider 206 rather than directly on the patient's chest 214. The orientation of the heart image 212 within the field of view 230 is also manipulated (e.g., rotated about 90 degrees) to maintain the spatial relationship between the heart image 212 and the patient's chest 214.

Processes for Generating and Interacting with Three-Dimensional Environment

The augmented reality devices 120 and systems described herein can be configured to implement processing routines for obtaining information about a rescue scene and providing feedback about the rescue scene and/or rescue effort to an acute care provider wearing an augmented reality device 120. The processing routines can be implemented by the controller 130 of the augmented reality device 120. In other examples, some or all of the processing steps described herein can be performed by remote devices and processing circuitry associated with medical devices and/or computer devices located at the rescue scene or remote from and in wired or wireless communication with device(s) at the rescue scene. The exemplary processing routine can include, for example, receiving information from sensors of the augmented reality device(s) worn by acute care providers at the rescue scene, processing the received information to generate the three-dimensional representation of the rescue scene, generating the at least one virtual three-dimensional object within the three-dimensional representation, applying one or more spatially sensitive rules for positioning two-dimensional images of the virtual objects in the viewer's field of view, and providing guidance, for example, in the form of real-time feedback, to a viewer (e.g., to the acute care provider) wearing the augmented reality device for performing the resuscitation activity in accordance with the spatially sensitive rules.

In some instances, the wearer can manipulate and interact with visual feedback projected within his/her field of view by the augmented reality device 120 to, for example, obtain additional information about specific devices, objects, or individuals within his/her field of view. For example, the feedback can include information about whether resuscitation activities are being performed substantially correctly. In other examples, feedback can be provided in the form of a quality assessment provided after cessation of the resuscitation activity to provide an indicator (e.g., a score or metric) related to an overall quality of the resuscitation activities performed for the patient. In still other examples, feedback can comprise one or more alert notifications to provide information to acute care providers about various aspects of resuscitation events.

Figure 3:
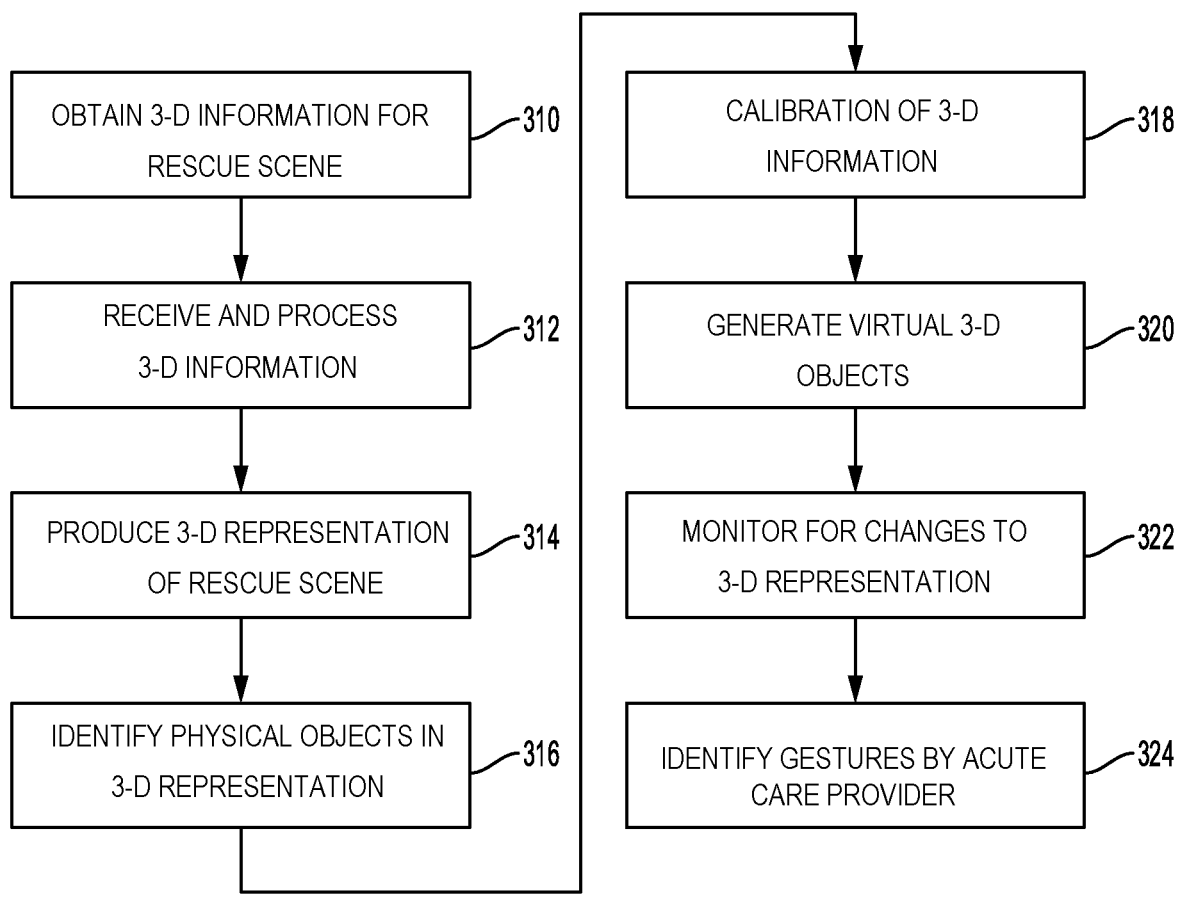
FIG. 3 is a flowchart of an exemplary process generating a manipulatable three-dimensional representation of a rescue scene with an augmented reality device according to an embodiment of the disclosure.

A flowchart illustrating an exemplary processing routine for generating a manipulatable three-dimensional representation of a rescue scene with an augmented reality device is shown in FIG. 3. As shown at box 310, three-dimensional information for a rescue scene is obtained from three-dimensional sensors of augmented reality device(s) at the rescue scene. In some instances, two-dimensional images, such as two-dimensional images which substantially correspond to the acute care provider's field of view, can also be obtained from the augmented reality devices. In some cases, numerous images may be obtained as the acute care provider moves around and/or observes different areas of the rescue scene before the three-dimensional representation of the entire rescue scene can be generated. In other examples, three-dimensional information and images can be simultaneously obtained from sensors and/or cameras associated with augmented reality devices worn by multiple acute care providers so that information representative of an entire rescue scene can be obtained more quickly and/or accurately. Or, three-dimensional information may be further obtained from sensors and/or cameras that are not physically coupled with an augmented reality device. The obtained information can be transmitted to a controller or controller device for processing. As discussed herein, in some instances, processing is performed by a controller associated with an augmented reality device worn by an acute care provider. In other examples, the controller is remote from the augmented reality device(s) or rescue scene.

As shown at box 312, the three-dimensional information and images are received and processed by the controller. The three-dimensional information and images can be received by the controller substantially in real-time. As the information is received, it can be stored on computer-readable memory associated with the controller. Once substantial amounts of information about the rescue scene are received, the controller can begin to process the information. In other instances, a batch or group of images can be transmitted from the one or more augmented reality devices to the controller at one time. In some examples, when processing the received information, the controller can be configured to calibrate the processed three-dimensional information according to the one or more acute care activities based on a user-initiated action by the acute care provider. For example, a user-initiated action can comprise connecting an electrode assembly to a processor of a defibrillator or ECG monitor. In that case, the received information can be processed to identify or recognize whether the electrode assembly is an adult or a pediatric electrode assembly, which may serve to provide information as to whether the patient is adult or pediatric.

As shown at box 314, processing received information and images can further comprise generating or producing a three-dimensional representation of the rescue scene based on the received three-dimensional information or images. For example, producing the three-dimensional representation can include correlating objects in the captured images with physical objects identified based on the three-dimensional information to refine or better characterize the physical objects. In some instances, generation of the three-dimensional representation can comprise organizing or characterizing received images based on location or point-of-view of the obtained images. For example, each received image can include information (e.g., metadata) describing the direction the acute care provider and/or that the camera was facing when the image was obtained. Obtained images can also include time information about when the images were captured, so that images can be arranged chronologically to show changes to the acute care provider's field of view and/or to the rescue scene over time. Based on the location and time information for the captured images, the controller can organize the images to provide a time-dependent representation of the rescue scene.

In some examples, generation of the three-dimensional representation of the environment (e.g., the rescue scene) comprises fractal or three-dimensional mapping techniques of the three-dimensional space as are known in the art. In some examples, the mapping techniques comprise generating a three-dimensional skeleton or reference frame around the wearer which moves or adjusts position in accordance with the wearer's movement. In that case, the virtual three-dimensional objects to be displayed to the wearer can be positioned in the three-dimensional representation based on a position and orientation relationship between the wearable augmented reality device and the three-dimensional skeleton or reference frame. Images of the virtual objects display to the acute care provider may be moved, repositioned or otherwise manipulated based on changes to a position of the skeleton or reference frame and/or changes in position to physical objects within the three-dimensional representation of the rescue scene to maintain relative positioning of the wearer and the images of a virtual object.

As shown at box 316, processing the three-dimensional information and images can also comprise identifying physical objects in the generated three-dimensional representation of the rescue scene. For example, the controller can be configured to identify items in the three-dimensional representation including, for example, medical devices (e.g., defibrillators, ventilators, ventilation bags, patient monitoring devices, etc.), disposable medical instruments (e.g., syringes, medical vials, bandages, medical tubing, electrodes and electrode packaging, IV-bags, oxygen canisters, etc.), vehicles and transportation devices (e.g., cars, trucks, ambulances, stretchers, litters, wheelchairs, etc.) and/or environmental hazards (roads, power lines, buildings, trees). In some instances, identification of physical objects can include processing two-dimensional images captured by cameras to identify regions of the image including colors and/or shapes representative of items typically found at a rescue scene (e.g., color matching techniques). In other examples, images may be processed to determine a general outline or boundary of objects in the images. The outline or boundary can be compared to shapes of objects commonly found at a rescue scene to identify objects in the images (e.g., shape matching). In other examples, physical objects may include tags or labels with text or icons describing the item. The controller can be configured to locate and extract information from (e.g., read) labels in captured images to determine information about the tagged item.

In a similar manner, the controller can be configured to identify individuals, such as patients or victims, bystanders, and other acute care providers, present at the rescue scene. Identification of individuals can be based on an individual's position or movements as shown in the produced three-dimensional representation or captured images. For example, an individual that is lying down (e.g., horizontal) in the three-dimensional representation can be identified as a patient. Individuals that are moving around and wearing uniforms of a particular color can be identified as acute care providers. In some examples, facial recognition processing techniques can be used to distinguish between different acute care providers or other individuals at the rescue scene. In some examples, generation of the three-dimensional representation can also include identifying a patient's face. The identified face can be obscured or blocked out in stored images to preserve the patient's privacy, anonymity, and/or to comply with certain health privacy requirements for medical records. Techniques for identifying and obscuring a patient's face and/or other portions of the patient's body in images captured at a rescue scene are described in the aforementioned United States Patent Pub. No. 2014/0342331, entitled "Cameras for Emergency Rescue."

As shown at box 318, in some examples, certain calibration procedures may be performed during use of the augmented reality device to supplement information determined from the analysis of the three-dimensional information and images. In particular, the controller can be configured to calibrate the processed three-dimensional information according to one or more acute care activities performed by the acute care provider and/or based on a user-initiated action by the acute care provider. For example, once the patient is identified in captured images by the augmented reality device, the augmented reality device may be configured to provide calibration instructions to one of the acute care providers to provide a more precise representation of the patient's anatomy and position. For example, the acute care provider may be instructed to touch specific areas of the patient (e.g., touch sternal notch, touch axilla, or move hands along a lower portion of the patient's ribs). As the calibration routine is being performed, images captured by the augmented reality device may be processed to track movement of the acute care provider's hands. In particular, the hand location can be used to determine exact position of anatomical structures which may not be visible in captured images. The three-dimensional representation of the rescue scene can be modified based on the precise location information.

As shown at box 320, after the three-dimensional representation of the rescue scene is generated, the controller can be configured to generate and position one or more virtual three-dimensional objects in the three-dimensional representation of the rescue scene. The virtual three-dimensional object(s) may provide instruction to the acute care provider in providing resuscitative treatment to the patient. The virtual three-dimensional object(s) can comprise, for example, a virtual CPR indicator overlaid on or within the patient's body within the field of view of the acute care provider or virtual CPR indicators that provide feedback representative of a quality with which the acute care provider is administering CPR to the patient. A virtual CPR indicator could comprise a chest compression indicator that provides feedback representative of a quality with which the acute care provider is administering chest compressions to the patient according to whether one or more chest compression parameters (e.g., chest compression depth, chest compression rate, acute care provider body alignment, and acute care provider fatigue) are within a desired range. Other examples of such virtual objects are provided further below. It should be understood that the basic premise described herein for providing a mixed reality environment to the acute care provider via the augmented reality device may be applied to embodiments of the present disclosure. That is, the virtual three-dimensional object(s) described herein may be presented on the visual display as two-dimensional image(s) and subject to spatially sensitive rules such that the wearer is able to interact with the virtual object(s). For example, the wearer may, through gestural recognition (e.g., pushing, grabbing, and/or manipulating the space occupied by the virtual three-dimensional object), be able to actively move, modify, or otherwise adjust the appearance/presentation of the virtual object so as to interact therewith.

Generated virtual objects can be positioned in accordance with spatially sensitive rules for interaction with physical objects in the acute care provider's field of view. For example, spatially sensitive rules for generation of the image of the virtual three-dimensional object on the visual display can include a position and orientation relationship between the wearable augmented reality device and the three-dimensional skeleton or reference frame of the three-dimensional representation. As discussed herein, the images of a virtual object can take a variety of forms including visual indicators, holograms, and animations.

Images of the virtual three-dimensional object(s) can be displayed in the wearer's field of view based on a position of the virtual three-dimensional object in the three-dimensional representation of the rescue scene. For example, an image of a CPR indicator could be displayed overtop of a patient's chest. In that case, the position of the two dimensional image is generally dependent on positions of identified physical objects in the acute care provider's field of view. In other examples, two-dimensional generated images may be projected in the acute care provider's field of view in an unchanging position and not relative to physical objects in the field of view. For example, various dashboards and heads up displays may be positioned on the periphery of the acute care provider's field of view so as not to obscure the acute care provider's view of physical objects at the scene. For example, a heads-up display with information about the patient may be permanently positioned in the top right-hand corner of the acute care provider's field of view, so that he or she can occasionally glance at the display to obtain information about the patient. In that case, as the acute care provider changes position or begins looking at other areas of the rescue scene, the projected dashboard or heads up display remains in its position in the top right corner of the rescuer's field of view.

In some examples, the generated images can be displayed with a three-dimensional appearance. In that case, the image may be displayed not merely to overlay or cover physical objects in the field of view, but in a manner so as to be able to interact with such physical objects according to spatially sensitive rules. In a simple example, an image of a virtual object sitting on a table or flat surface may be displayed to the acute care provider. The acute care provider can interact with and manipulate the image in the three-dimensional space by, for example, pretending to touch or grasp portions of the displayed image. Or, if the table or flat surface is turned over, then the image presented on the display of the augmented reality device may be modified such that the virtual object will appear to fall to the ground. In other examples, the virtual three-dimensional objects can be windows or projected openings which the viewer can gaze into.

As shown in box 322, after initial placement of virtual three-dimensional objects in the three-dimensional representation of the rescue scene, the augmented reality device is configured to continue to analyze the rescue scene based on received three-dimensional information and images to identify changes to the three-dimensional representation or when the acute care provider changes position and/or gaze direction. In that case, the controller may manipulate the image of the virtual three-dimensional object displayed to the acute care provider as an interaction with the one or more identified physical objects according to the one or more spatially sensitive rules that provides further feedback or guidance to the acute care provider for treating the patient.

In some examples, the augmented reality device may track movement of physical objects (e.g., the wearer's hand, medical devices, at the rescue scene, or the patient) in captured images and continuously or substantially continuously reposition the images of the virtual objects so that positioning of the virtual objects relative to the physical objects is maintained. The augmented reality device may also track the acute care provider's eye movement to identify when his/her gaze direction changes. Changes in gaze direction may also necessitate changing or adjusting position of some images of virtual objects in the acute care provider's field of view. In some examples, the types of information being presented to the acute care provider may need to be modified based on which direction the acute care provider is looking. For example, when the acute care provider looks at a medical device, such as a defibrillator, information about device status may be displayed within the acute care provider's field of view. When the acute care provider looks in a different direction, the image of a virtual object with information about the defibrillator is removed and/or replaced with images of a different virtual object.

As shown at box 324, in some instances, captured three-dimensional information or images can be analyzed to identify gestures performed by the acute care provider. Identification of a gesture can comprise processing the captured images to locate the position and/or orientation of the acute care provider's hands. For example, the acute care provider's hands can be identified by scanning images for areas including a larger proportion of skin colored pixels. Tracking changes in positions of the hands over time can be used to identify movement representative of particular gestures being performed by the acute care provider. As discussed herein, gestures can include hand motions or signals, such as making a swipe motion, holding up a predetermined number of fingers, making a fist, clapping hands, and others, that can be identified in a captured image. The motion or signal can be used to interact with the images of the virtual objects displayed to the acute care provider's field of view by the augmented reality device. For example, a swipe can be used to toggle between different screens or pages of a user dashboard. In other examples, hand signals or motions can be used to identify particular acute care providers or a resuscitation activity to be performed. For example, an acute care provider may make a compression motion to inform the system that he will begin performing chest compressions and that his augmented reality device should begin providing feedback to assist in performance of chest compressions.

Processes for Determining Resuscitation Activity Parameters

Figure 4:
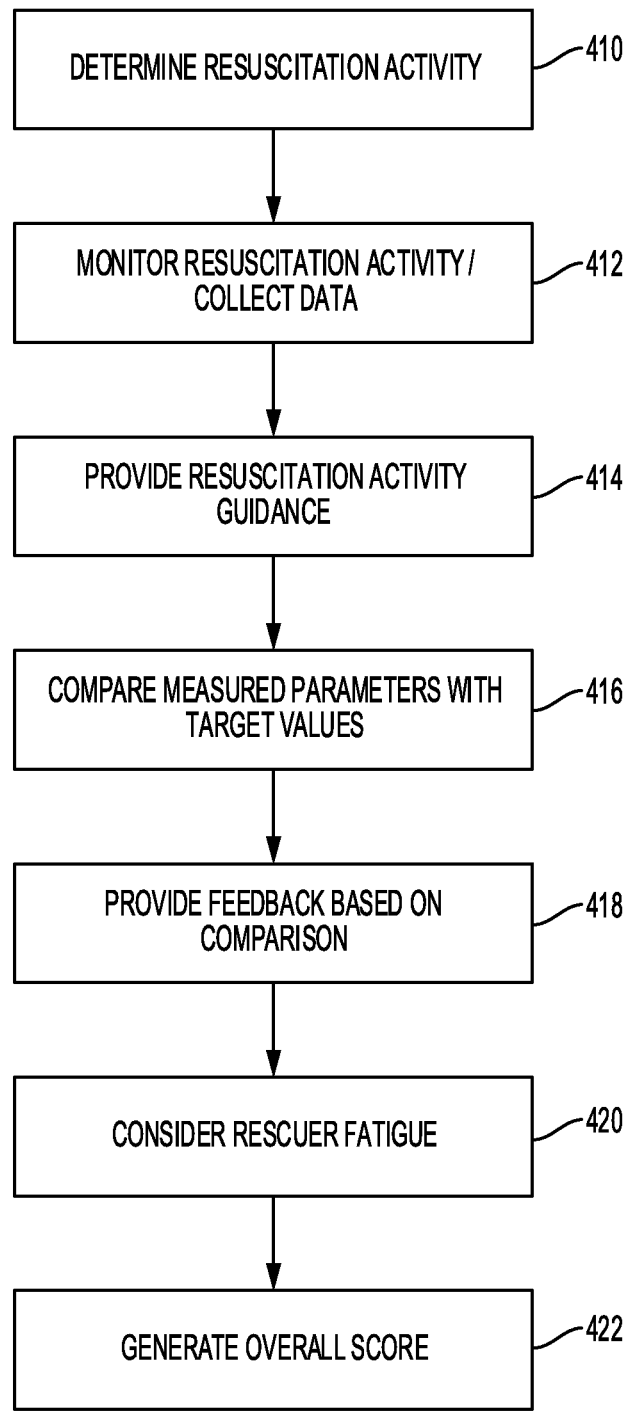
FIG. 4 is a flowchart of an exemplary process for manipulating a virtual information dashboard projected by an augmented reality device.

In addition to being used for generation of the three-dimensional representation of a rescue scene, images captured by the augmented reality device(s) may also be used for measuring and providing feedback, emergency resuscitation guidance, and/or medical treatment guidance for resuscitation and medical activity parameters. FIG. 4 is a flow chart showing a process for determining such parameters based on images captured by the augmented reality device(s).

As shown at box 410, the resuscitation activity being performed or to be performed is identified. Identifying the resuscitation activity can comprise identifying a gesture performed by the acute care provider representative of a resuscitation activity. The gesture can be identified in three-dimensional information or images captured by the optical sensor(s) of the augmented reality device as previously described. In other examples, identification of the resuscitation activity can comprise identifying arm or hand movements of the acute care provider indicating that performance of the resuscitation activity has already commenced. In other examples, the acute care provider may identify the resuscitation activity by speaking a phrase, such as "Beginning chest compressions now." The acute care provider's speech can be recorded by the microphone associated with the augmented reality device and processed by the controller to identify the resuscitation activity.

Once the resuscitation activity is identified, as shown at box 412, the controller begins processing received three-dimensional information and/or images to calculate or measure resuscitation activity parameters for the identified activity. For example, measuring or determining activity parameters can include tracking the acute care provider's movements to estimate range of motion, distance traveled, change of direction, or other relevant information. For chest compressions, movement and changes in direction of the acute care provider's hands during performance of chest compressions can be used to estimate chest compression rate and depth. Movement of the acute care provider's hands while compressing and releasing a ventilation bag during manual ventilation of a patient can be measured to estimate flow volume and/or flow rate during ventilations. Movement of the thumb and forefinger while holding a syringe can be identified and used to confirm that an injection was administered to the patient and/or to estimate a volume of a fluid being injected.

In some examples, a number, direction, or quality of images captured by cameras of the augmented reality devices may determine types of analysis that can be used for identifying the resuscitation activities and/or parameters in captured images. For example, if spectroscopic images of the patient or images from multiple cameras are available, then the images may be processed to determine depth or distance in captured images. Information about distance or depth can also be determined from three-dimensional information collected by three-dimensional sensors. Accurate depth and distance information can be used to determine parameters, such as chest compression depth, ventilation volume (e.g., how far the acute care provider compresses a ventilation bag), and others. In other examples, in order to preserve computing resources, the device may rely on static two-dimensional images of the rescue scene. In that case, since it may be more difficult to determine depth or distance traveled from captured images, information from other patient and resuscitation monitoring devices at the rescue scene (e.g., defibrillators, ventilators, accelerometer-based CPR assist devices, and others) may also be used to measure, or otherwise estimate, relevant resuscitation parameters. In a similar manner, images from stationary cameras positioned in the rescue scene may be used to supplement images obtained by augmented reality device(s).

As the resuscitation activity is being performed, the augmented reality device can provide feedback or guidance, such as emergency resuscitative guidance, for the acute care provider. For example, at box 414, the controller can cause the augmented reality device to display images of the virtual three-dimensional objects (e.g., visual indicators or holograms) in the acute care provider's field of view for the purpose of showing how the resuscitation activities should be performed. As discussed herein, the images can be positioned within the visual display in accordance with the spatially sensitive rules for positioning the virtual three-dimensional object(s) in interactive relation with respect to physical objects in the three-dimensional representation. The emergency resuscitation guidance can comprise, for example, icons or images showing the acute care provider correct positioning, placement, or movement for the acute care provider's hands and arms. Guidance can also include moving icons or images showing correct speed and direction for hand and arm motion to encourage the acute care provider, for example, to perform compressions at a desired compression rate, force, direction, and orientation.

In addition to providing guidance in performance of resuscitation activities, the augmented reality devices can also provide feedback about a quality of previously performed resuscitation activities. For example, as shown at box 416, as the resuscitation activities are being performed, the controller can also be configured to compare measured or identified parameters values to certain predetermined or calculated target parameters. As resuscitation activities are being performed, a time-stamped record can be created of resuscitation activity parameters to show changes in how resuscitation activities are performed over the course of the event or predetermined time interval.

For chest compressions, target parameters can include compression rate, depth, and compression cycle duration. In some examples, a preferred chest compression depth is about 2.0 inches, and an appropriate range for chest compression depths is between about 2.0 inches and 2.4 inches, according to the 2015 Guidelines by the American Heart Association (AHA) for Cardiopulmonary Resuscitation (CPR) and Emergency Cardiovascular Care (ECC). Target chest compression rate according to the AHA Guidelines can be between about 100 compressions per minute (cpm) and 120 cpm, and preferably about 105 cpm. These targets and ranges can be varied depending upon a selected protocol. For ventilation, target parameters can include ventilation rate and volume. Target ventilation rate may be about 10 ventilation breaths per minute (e.g., approximately 30 compressions for every 2 ventilation breaths) for adults and about 20 ventilation breaths per minute (e.g., approximately 15 compressions for every 2 ventilation breaths) for infants. Target parameters can also relate to synchronization or sequences of chest compressions and ventilations. For example, the augmented reality device can be configured to direct acute care providers to provide a number of compressions (e.g., about 15 compressions, 30 compressions) and then to pause compressions while delivering a specified number of ventilations (e.g., 2 ventilations). In some instances, target parameters can be predetermined and stored in memory associated with the controller, entered manually by the user prior to beginning the resuscitation activity, or automatically calculated by the device based, for example, on characteristics of the patient or acute care provider. For example, target compression depth can be based on a size or weight of the patient. In other examples, target compression rate and depth can be selected based on skill of the acute care provider. In other examples, target parameters can be received from an external source, such as an external computer or another medical device. For example, the target parameters can be based on a treatment protocol received from another medical device, such as a defibrillator or ventilator, or from a remote computer, computer network, or from a central server.

As shown at box 418, based on the comparison of the measured values and target parameters, feedback or guidance about quality of resuscitation activities being performed is provided to the acute care provider. As discussed herein, feedback can be provided in the form of visual indicators projected to the acute care provider's field of view by the augmented reality device. In some examples, feedback can be provided in a dashboard or heads-up display permanently displayed to be perceived by the acute care provider's peripheral vision. In other examples, visual indicators for providing feedback can be positioned within the acute care provider's field of view in relation to actual identified objects as images of the virtual objects presented on the visual display. For example, visual indicators related to chest compressions could be projected on top of the acute care provider's hands. Feedback related to cardiac blood perfusion or brain blood perfusion could be projected over the patient's heart or brain.

In some instances, audio or vibration feedback may be provided along with the visual feedback from the augmented reality device to provide additional information to the acute care provider. For example, the speakers of the augmented reality device may be configured to emit multiple tones (e.g., tones forming a major chord) to encourage the acute care provider in performance of the resuscitation activity, such as if the measured values are within a predetermined range of the measured values. Similarly, the augmented reality device can be configured to emit multiple tones forming a minor or descending chord to signify to the acute care provider to modify performance of the resuscitation activity, if it is determined that the measured values are more than a predetermined amount from the target values.

In some instances, as shown at box 420, acute care provider fatigue can be identified by monitoring changes in the comparison between the measured values and target parameter values over time. For example, if the comparison between measured values for the resuscitation activity being performed and the target parameter values demonstrates a decrease in quality of chest compressions (e.g., a difference between measured values for the resuscitation activities being performed and the target values increases over time), it can indicate that the acute care provider is becoming fatigued. If it is identified that the acute care provider is becoming fatigued, the device can provide a notification to inform the acute care provider that he or she should switch places with another acute care provider.

Following cessation of the resuscitation activities and/or after treatment of the patient is completed, as shown at box 422, an overall score or metric can be calculated from the time-stamped record of resuscitation activities. In some examples, a score or metric can be generated for each acute care provider at a rescue scene. In that case, the processing routine can include steps for receiving images from one or more augmented reality devices at the rescue scene, and for processing the received images to identify activities performed by particular acute care providers. The metric or score can be in the form of a numeric or letter score representative of quality of treatment provided to the patient. Since an acute care provider may perform a variety of different types of resuscitation activities over the course of a rescue event, the score or metric can be inclusive of quality of different types of resuscitation activities.

In some examples, a time interval can be selected to limit when performance of the resuscitation activity performance is considered. For example, a pre-selected interval can be used (e.g., an interval of 30 seconds). In other examples, the interval can be based on the duration of a normal CPR cycle (e.g., a cycle consisting of 15 compressions followed by two ventilations). In that case, a score or metric for each time interval can be calculated. In some examples, a separate score or metric can be calculated for each resuscitation activity performed based on motion signals received from a device in accordance with the present disclosure. A final total or overall score for all resuscitation activities performed by each acute care provider during the entire duration of treatment can also be calculated and provided to the acute care provider. Exemplary algorithms for calculating a score or metric representative of overall quality of CPR based on signals received from motion sensors are described in United States Patent Publication No. 2013/0296719, entitled "Rescue Performance Metric," which is hereby incorporated by reference in its entirety.

In some examples, calculation of a score or metric can be adjusted based on environmental factors. For example, it is recognized that performing resuscitation activities while a patient is being transported in an ambulance can be more difficult than performing resuscitation activities prior to transport of the patient. Therefore, if it is determined that the patient is being transported, the metrics for evaluating the acute care provider may be adjusted. For example, to account for the acute care provider being subject to conditions where it is more challenging to administer CPR or when CPR quality is likely to be compromised, the manner in which an acute care provider is evaluated may be relaxed and the overall performance evaluation may be higher. Or, for purposes of evaluating acute care provider performance, CPR measurements during transport may be discounted from the overall score.

The calculated score or metric can be provided to the one or more acute care providers. For example, the score or metric can be projected within the acute care provider's field of view by the augmented reality device. In other examples, a score or metric can be given to the acute care provider in the form of a report card provided to each acute care provider at a follow-up meeting or briefing after the rescue effort is completed. In some examples, the report card can include a score or metric for each resuscitation activity performed by the acute care provider. In addition, the report card can include an individual score for each time interval which demonstrates changes in treatment quality over time. In addition, the report card can include a combined or total care metric determined by combining scores for each of the acute care providers that treated the patient. Further, the total care metric can be considered in connection with outcome information related to the physical condition of the patient to provide a correlation between acute care providers, resuscitation activities performed, and effects of the treatment for the patient.

Exemplary Dashboard Displays

Figure 5:
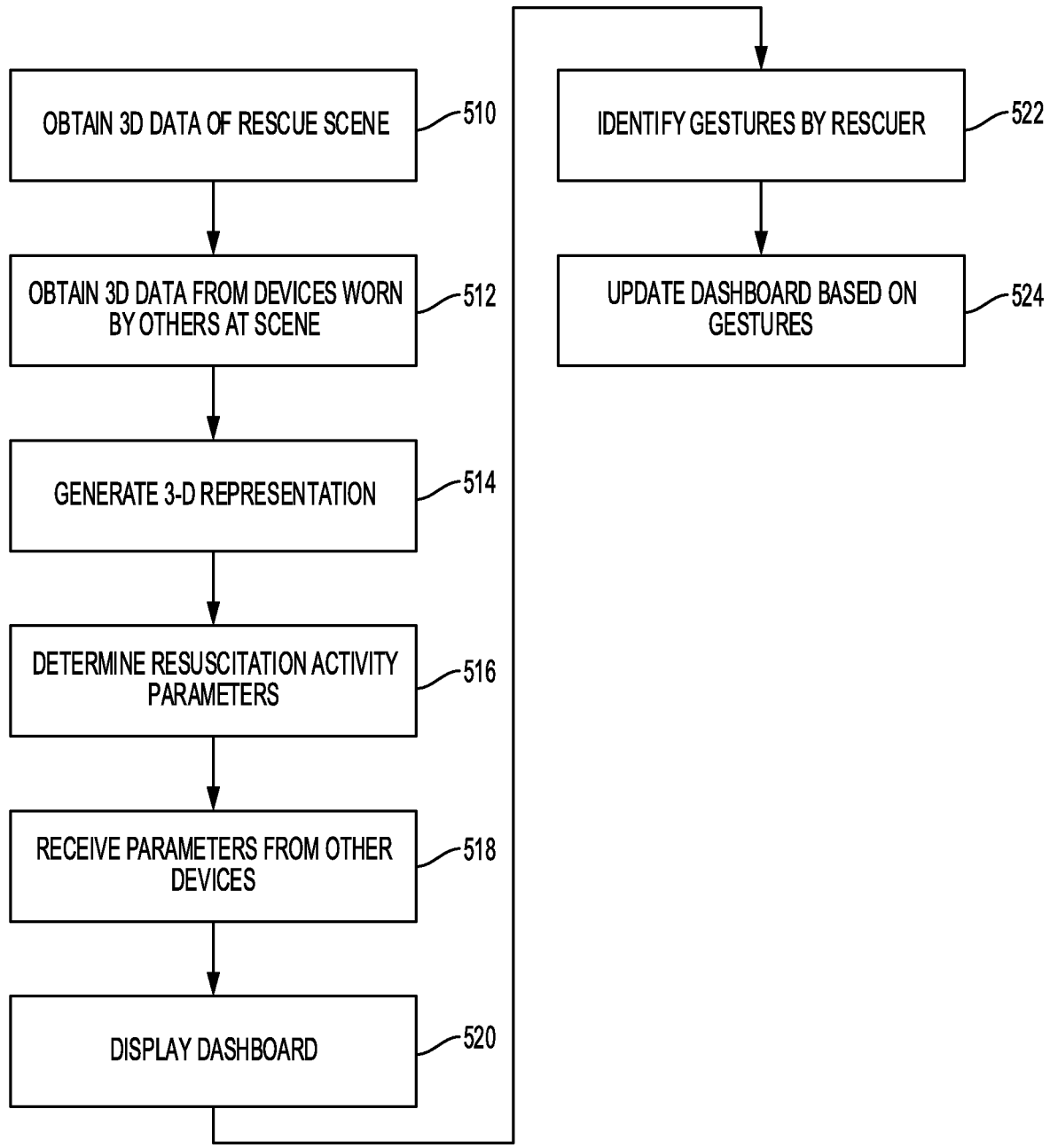
FIG. 5 is a flowchart of an exemplary process for providing and updating a dashboard display on an augmented reality device according to an embodiment of the disclosure.
Figure 6A:
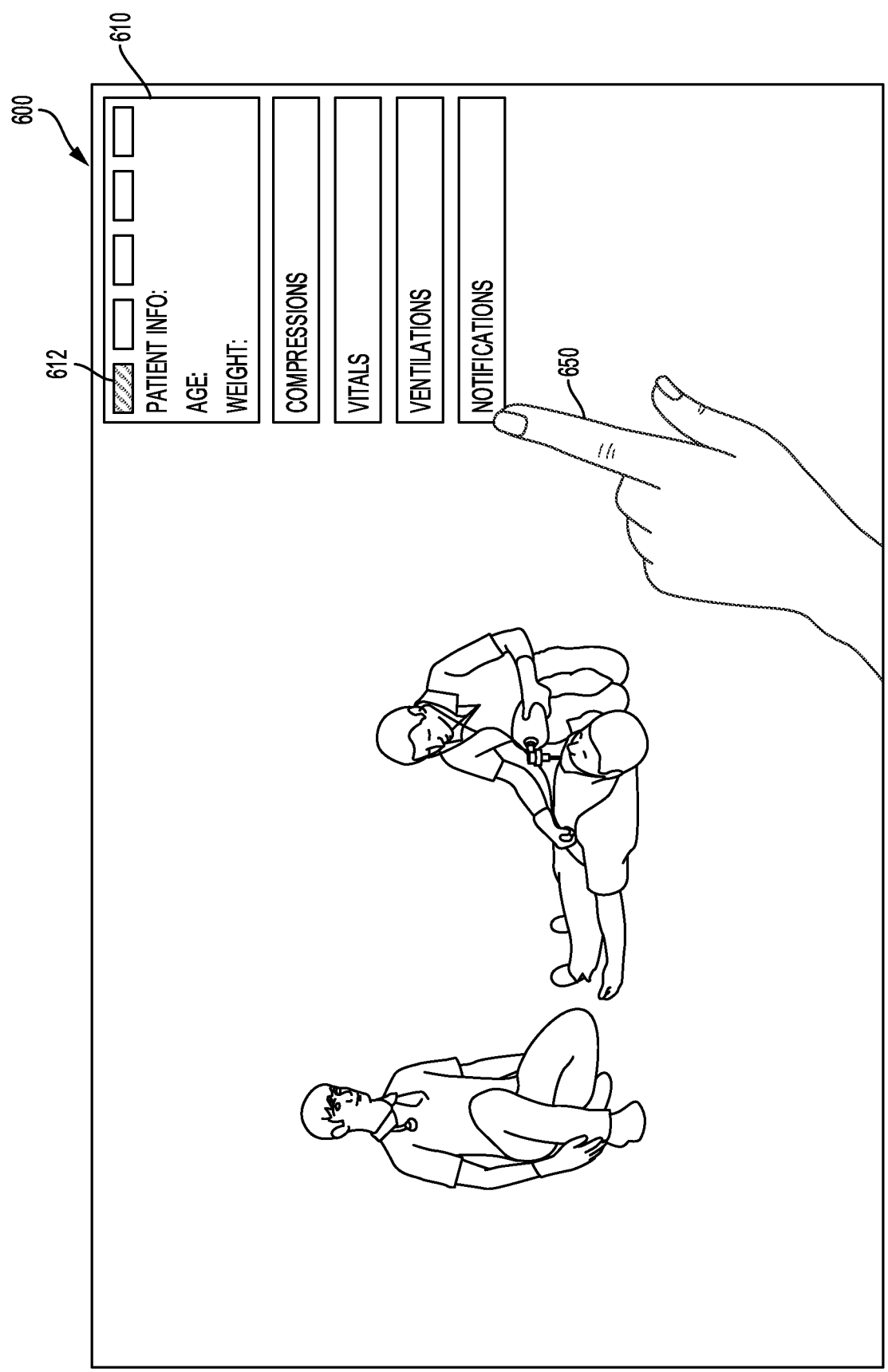
FIG. 6A shows an exemplary field of view through an augmented reality device including a dynamic dashboard display.
Figure 6B:
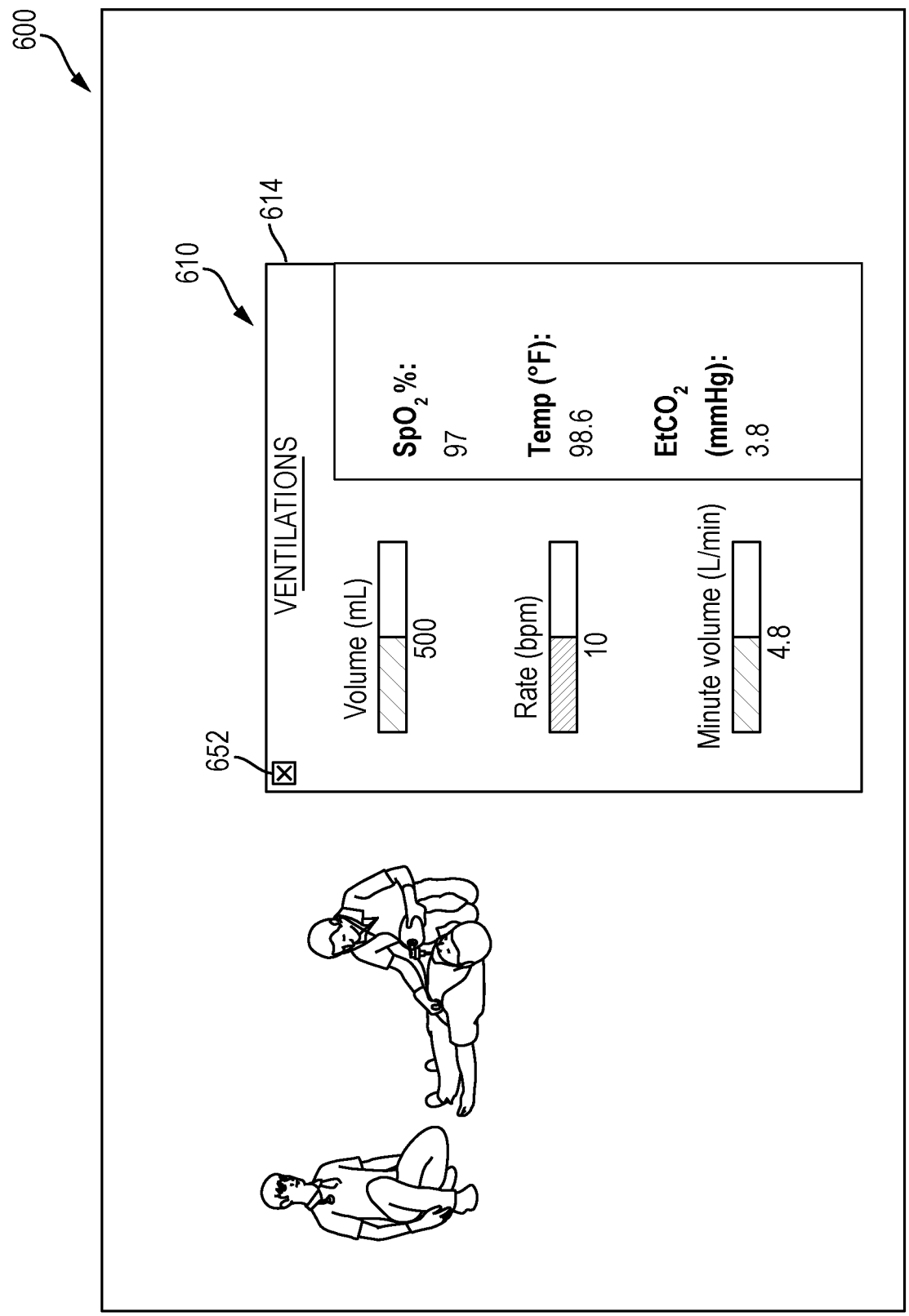
FIG. 6B shows an exemplary field of view through the augmented reality device with another screen of the dynamic dashboard display of FIG. 6A.
Figure 7:
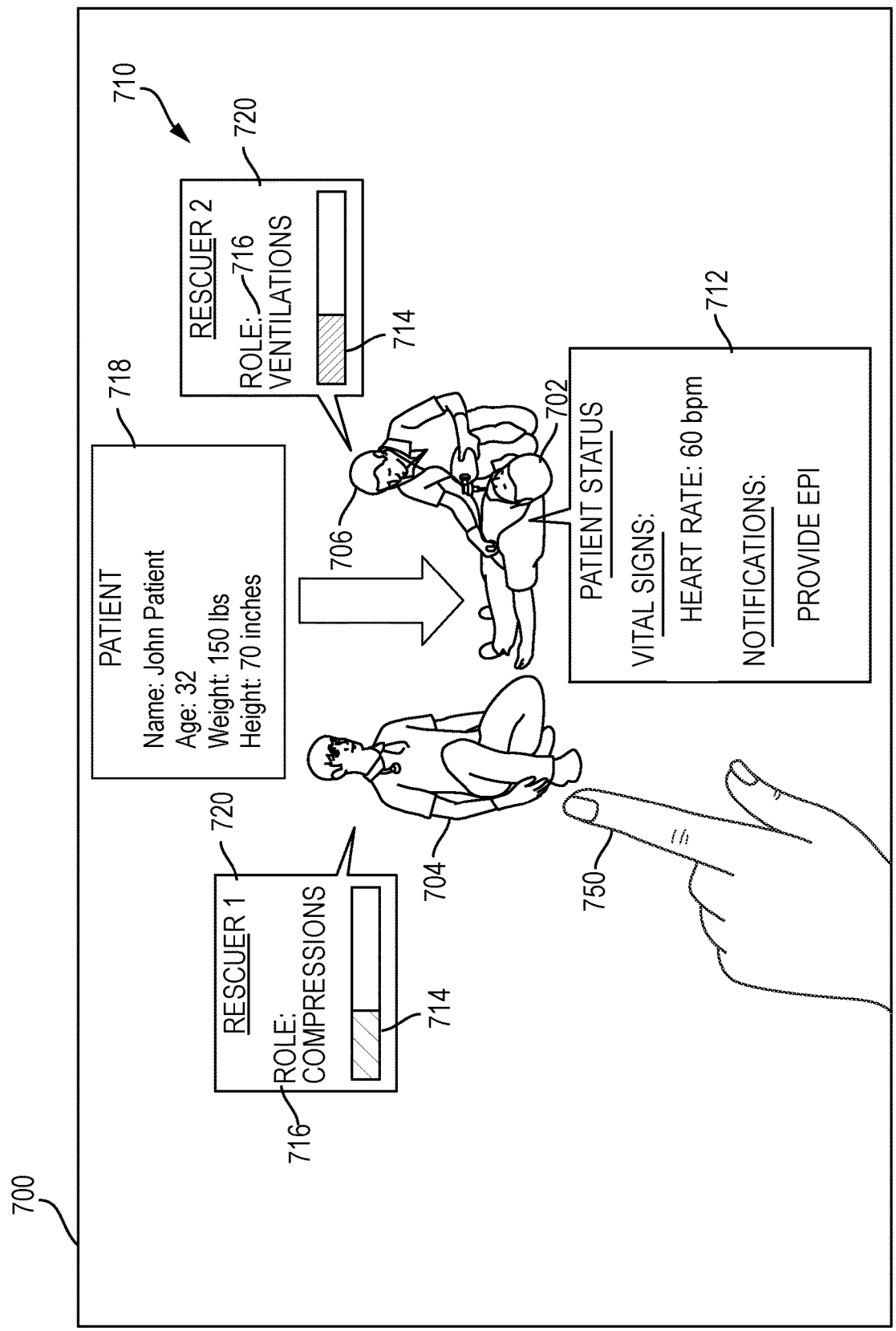
FIG. 7 shows an exemplary field of view through an augmented reality device including a dynamic dashboard display for a lead acute care provider.

According to an aspect of the disclosure, the augmented reality device can be used to project a dashboard display to the acute care provider's field of view. Processes for generating and manipulating a dashboard display are illustrated by the flow chart in FIG. 5. Exemplary dashboard displays projected to the field of view of an acute care provider using an augmented reality device are shown in FIGS. 6A, 6B, and 7.

In some examples, a dynamic dashboard comprises visual indicators, such as gauges, numeric values, text, and other images of a virtual object that are placed within the wearer's field of view for interaction with a generated three-dimensional representation of the environment to intuitively convey information about the rescue effort. For example, the dashboard display can comprise information about the acute care provider wearing the augmented reality device, the rescue effort (e.g., duration of rescue effort, or time until a resuscitation activity ceases), rescue scene (e.g., location information, environmental hazards), patient (e.g., patient age/weight, down time, known allergies or medications taken), or other acute care providers (status of acute care providers, resuscitation activities being performed by other acute care providers).

In some instances, the information is derived from images captured by the augmented reality device. For example, the captured images/video can be processed and analyzed to determine resuscitation quality parameters including chest compression depth, chest compression rate, and others. The dashboard display may also include information from other sources, such as patient monitors, therapeutic medical devices, and physiological sensors, connected to the patient. The dashboard can be a dynamic dashboard display meaning that the dashboard changes or adjusts based on environmental conditions and/or actions of the acute care provider. For example, the acute care provider can perform gestures or movements to select which information to display at a particular time. In other examples, the dashboard display can comprise one or more "pop-up" displays which appear when the acute care provider looks in a predetermined direction (e.g., glances at the corner of a room) or at a physical object in the rescue scene. For example, various pop-up displays may appear as image of virtual objects each time that the acute care provider looks at or begins to interact with a specific medical device or instrument.

Processes for Accessing and Manipulating a Dashboard Display

Processes for accessing and manipulating an exemplary dashboard display will now be described in detail. FIG. 5 shows a flow chart illustrating an exemplary process performed by the controller and augmented reality device for providing the dashboard display to the acute care provider and for updating the display based on gestures performed by the acute care provider. First, information and data about the rescue effort, patient, and acute care providers is received from a variety of sources. For example, at box 510, three-dimensional information and/or a series of images or other visual information of the rescue scene corresponding to the field of view of the acute care provider wearing the augmented reality device may be received by the controller. Optionally, at box 512, the controller may also receive and process images from augmented reality devices worn by other acute care providers at the rescue scene. At box 514, the received three-dimensional information and images can be processed by the controller to produce the three-dimensional representation of the rescue scene. In some implementations, the three-dimensional representation may be generated more directly than from multiple images or multiple received images, for instance, by using three-dimensional sensors, such as the Intel RealSense D415 camera or Apple TrueDepth camera employing vertical-cavity surface emitting lasers (VCSELs) such as those provided by Finisar (Sunnyvale, Calif.), or structured light source 3D sensors. For instance, three-dimensional sensors may be set up to structurally scan the field of view (e.g., by projecting a series of reference points, dots, and/or a grid outward into the field of view and sensing the location, orientation or movement of the reference points/grid to effectively generate a three-dimensional structural scan). Based on one or more received images and/or the three-dimensional representation, the controller may also recognize objects and persons within the field of view as well as determine the roles of those persons or objects (e.g., "victim," "rescuer #1," "rescuer #2,", "defibrillator", "defibrillator electrodes", "Ventilator bag", "Stretcher", "Ambulance" etc.).

Based on the aforementioned United States Patent Appl. Pub. No. 2014/0342331, a controller, module or other processor(s) can detect and identify faces of the people at the rescue scene 100 (shown in FIG. 1), such as the victim 102 and/or one or more of the rescuers 104, 106. For instance, the processor(s) can implement a facial detection algorithm (e.g., such as the facial detection algorithm described below) that analyzes the images from one or more of the cameras and/or the representation to automatically detect and identify faces at the rescue scene 100. The identified faces can be labeled in the representation, e.g., with a generic identifier (e.g., "victim," "rescuer #1," "rescuer #2," etc.). For instance, in one example, facial recognition can be performed using an algorithm that implements face detection as a specific case of object-class detection. In general, object-class detection aims to find the locations and sizes of all objects in an image that belong to a given class of objects, such as upper torsos, pedestrians, cars, or other objects. Face detection in particular aims to find the locations and sizes of an unknown number of faces in an image. Such facial detection techniques may implement one or more processes, methodologies, etc. For example, a principal component analysis (PCA) based technique may be employed that uses orthogonal transformation to convert a set of observations of relatively correlated variables (e.g., such as facial features) into a set of variable referred to as principal components. In some arrangements, representations (e.g., captured images) of various types of facial features may be used for PCA, for example, naturally occurring facial features (e.g., eye brows, wrinkles, etc.), artificial features (e.g., one or more markers, make-up, etc. applied to the face), combinations of natural and artificial features, etc. Techniques such as PCA, may also assist with compressing data representing facial expressions for later retrieval and analysis such as scene reconstruction.

Some examples of face detection algorithms focus on the detection of frontal human faces. Some examples of face detection algorithms attempt to solve the more general problem of multi-view face detection, which is the detection of faces that are rotated along the axis from the face to the observer (in-plane rotation) and/or rotated along the vertical or left-right axis (out-of-plane rotation). These latter face detection algorithms can take into account variations in images or video resulting from factors such as facial appearance, lighting, pose, and/or other factors.

In other examples, as known to those of skill in the art, neural networks, such as Convolutional Neural Networks (CNN) can be used for visual recognition tasks such as object detection, image captioning, and dense image captioning. For instance, an image with a defibrillator, two rescuers and a patient lying on the ground might be analyzed and appropriately captioned, for example, by, "Two rescuers are treating an unconscious victim with a defibrillator." Examples of such analysis and caption algorithms are described in "Imagenet classification with deep convolutional neural networks," Proceedings of the 25th International Conference on Neural Information Processing Systems, Volume 1, 2012, Alex Krizhevsky et al.

As shown at box 516, the one or more images, or the one or more generated three-dimensional ("two- and three-dimensional") representations of the rescue scene can be analyzed to determine certain resuscitation activity parameters for activities being performed by the acute care providers at the scene. For example, resuscitation parameters including compression depth, compression rate, ventilation rate, and ventilation volume can be determined based on analysis of the generated two- and three-dimensional representation(s) of the rescue scene. The two- and three-dimensional representation(s) can also be analyzed to confirm that certain activities or tasks have been performed and/or provided to the patient. For example, the augmented reality device may confirm that tasks, such as setting up medical devices, administering drugs to the patient, and taking patient vital signs, were performed at an appropriate time. At box 518, the controller can also receive resuscitation activity parameters from additional sensors and/or medical devices located at the rescue scene. For example, resuscitation activity parameters may be received from the CPR assistance device (e.g., CPR puck), ventilation sensors associated with the ventilation bag, patient sensors (e.g., pulse oximetry sensors, ECG sensors, heart sounds sensors), as well as medical devices such as the defibrillator and ventilator.

Once the information is received and processed, at box 520, the controller causes the augmented reality device to display the dashboard to the acute care provider within the acute care provider's field of view. The dashboard can be displayed at any convenient position within the acute care provider's field of view. In many cases, to avoid distracting the acute care provider during performance of resuscitation activities, it is expected that the dashboard will be displayed near the periphery of the acute care provider's field of view and/or spaced apart from the patient and other acute care providers at a rescue scene. In some examples, the dashboard can include text and numerical values representing different resuscitation activity parameters and measured physiological values. In other examples, measured physiological values can be presented graphically through gauges, graphs, charts, and other icons. In some examples, overview information about the patient and/or rescue effort can be displayed continuously on a dashboard projected to the acute care provider's peripheral visual. In other examples, the dashboard can include multiple screens or reports. The acute care provider may toggle through the various screens or select tabs corresponding to different types of information to select which information is displayed on the dashboard.

In some instances, the augmented reality device is configured to monitor and/or identify inputs from the acute care provider to adjust or update the dashboard display. For example, the augmented reality device can continue to collect and transmit images of the rescue scene in substantially real-time to the controller to provide a real-time indication of the acute care provider's field of view. The controller is configured to receive and process the images to identify objects in the processed images. With particular relevance to updating the dashboard display, at box 522, the images are processed to identify gestures and/or actions by the acute care provider's hands. For example, the acute care provider may perform a swiping motion to toggle between different pages or tabs of the dashboard display. In other examples, the gesture can be pointing to a particular measured value or data entry of interest to receive additional information about the selected entry. In other examples, the acute care provider can point to an object or individual at the rescue scene, such as a medical device (e.g., defibrillator or acute care provider), patient, or another acute care provider, causing a dashboard with information specific to the selected object or individual to pop up in the acute care provider's field of view. Based on the identified gesture, as shown at box 524, the controller causes the augmented reality device to update the dashboard display with the updated or new information.

Exemplary Dashboard Displays for Augmented Reality Device

FIGS. 6A and 6B show an exemplary field of view 600 through the augmented reality device including a dynamic dashboard display 610. As shown in FIG. 6A, the dashboard 610 is positioned in the upper right hand corner of the acute care provider's field of view 600 in an inconspicuous position that is intended not to interfere with the acute care provider's perception of other objects in his/her field of view 600 or with the acute care provider's performance of resuscitation activities. The dashboard 610 may comprise a first screen 612 or tab with general information about the patient and rescue effort. For example, as shown in FIG. 6A, the first screen 612 comprises information about the patient including age and weight. The first screen 612 may also comprise general information about the rescue effort including duration of resuscitation activities and patient down time (e.g., elapsed time since the physiological event such as a heart attack occurred).

The dashboard 610 may also comprise a number of more specific screens or tabs with detailed information about specific parameters or resuscitation activities. In some instances, the augmented reality device may automatically select the more detailed screen or tab to show to the acute care provider based, for example, on which resuscitation activity the acute care provider is performing, the patient's condition, or preselected preferences of the particular acute care provider. For example, if the acute care provider is providing ventilations to the patient, the screen displayed on the dashboard 610 may comprise measured values for ventilation volume and ventilation rate displayed along with target values for these parameters. In other examples, the user can manually select which more detailed screen to view by, for example, performing a selection gesture that can be recognized by the augmented reality device. As shown in FIG. 6A, one of the acute care provider's hands 650 is visible. The acute care provider's hand 650 is pointing to a virtual button for "Ventilation", thereby recording a selection that a more detailed screen with information about ventilation should be displayed to the acute care provider.

As shown in FIG. 6B, as a result of the selection by the acute care provider, a ventilation screen 614 with more detailed information about ventilations provided to the patient is displayed. The ventilation screen 614 can include gauges and numerical values for ventilation parameters including ventilation volume (L/min), ventilation rate (bpm), minute volume (L/min), oxygen saturation ($SpO_2$%), Temperature (° F.), and/or end tidal $CO_2$ (mmHg). In some examples, the ventilation screen 614 could also include graphs (not shown) showing changes in one or more of the parameters over time. In order to assist the acute care provider in reviewing the more detailed information, portions of the dashboard 610 can be automatically repositioned to the center of the acute care provider's field of view 600, so that it can be read more easily. The repositioned screen can remain in the center of the field of view 600 even as the acute care provider changes position or moves his/her head. When positioned at a prominent location within the acute care provider's field of view 600, the dashboard 610 and/or other images of a virtual object may be at least partially transparent (e.g., faded or see through), so that the wearer is able to perceive physical objects in an unobstructed manner. The acute care provider can manually close or minimize the dashboard 610 by performing a preselected gesture, such as a swipe or by pointing to a specific portion of the dashboard (e.g., pointing to an "x" icon 652).

Exemplary Dashboard Display for Lead Acute Care Provider

In some examples, a dynamic display is tailored for use by a lead acute care provider. The lead acute care provider can be responsible for overseeing the entire rescue effort. The lead acute care provider's responsibilities can include assigning roles to respective acute care providers of a rescue team, monitoring performance of an assigned resuscitation activity by each of the respective acute care providers, and deciding when acute care providers should switch roles. The lead acute care provider can also be responsible for coordinating transportation of the patient to a hospital emergency room and ensuring that any necessary information about the patient and/or rescue effort is provided to emergency room staff members. In some cases, the lead acute care provider may be positioned a distance away from the patient allowing him/her to view multiple aspects of the treatment effort simultaneously.

In view of such responsibilities, the dynamic dashboard tailored for the lead acute care provider can comprise information about the patient, other acute care providers at the scene, and/or about the location and rescue effort. The information is desirably provided in a coordinated and organized fashion, so that the lead acute care provider can quickly ascertain important information about the patient and team of acute care providers, while continuing to perceive events at the rescue scene as they occur. For example, feedback about the patient and team of acute care providers can be provided to the lead acute care provider as images of a virtual object overlaid on the patient and/or acute care providers. In some instances, the lead acute care provider may be able to manipulate the image(s) of virtual objects, such as by performing certain hand gestures, to obtain additional information about a particular acute care provider or patient and/or to remove images of a virtual object to more easily perceive the actual rescue scene.

An exemplary field of view 700 for a lead acute care provider including the dynamic dashboard display 710 is shown in FIG. 7. The field of view 700 includes the patient 702 and acute care providers 704, 706 providing resuscitation activities for the patient 702. The dynamic dashboard 710 includes popup boxes and messages at different locations within the field of view 700. For example, an overall status screen 712 is provided in a central location within the field of view 700. The overall status screen 712 can include detailed information about the patient's condition including patient vital signs, physical characteristics, and/or known medical information, such as any known medical conditions, allergies, and medications being taken. The overall status screen 712 can be partially transparent or see through, so that the wearer can see rescue activities occurring at the rescue scene. Further, as in other examples, the lead acute care provider can minimize or move the screen 712 by, for example, performing a gesture, such as touching a portion of the screen 712 or swiping the screen 712 out of the way.

The dynamic dashboard display 710 further comprises messages or pop-up boxes for the patient 702 and for the multiple acute care providers 704, 706 which appear to float above the individuals' 702, 704, 706 heads. For example, a patient box 718 could include identifying information about the patient, such as name, age, weight, and/or height. The box 718 could also include information about the patient's medical history or known medical conditions, if available. The patient information could be downloaded from a patient medical record or manually entered at the rescue scene by one of the acute care providers.

The dashboard 710 further comprises information boxes 720 with status information for the acute care providers 704, 706. For example, the box 720 can include an indication 716 of the type of resuscitation activities being performed by the acute care provider (e.g., "Chest compressions", "Ventilations", "Administering a medication", etc.). Alternatively or in addition, the box 720 can include information about which types of activities the acute care provider 704, 706 is capable of performing and/or for which the acute care provider has received suitable training. This information may assist the lead acute care provider in determining which of the acute care providers 704, 706 present at the rescue scene are available to switch to a new role if needed. The box 720 can also include an acute care provider fatigue bar 714 representing an estimated energy level of the acute care provider 704, 706. The fatigue bar 714 can provide a visual representation of how tired an acute care provider is and, importantly, an indication of when an acute care provider should change roles or take a break. Acute care provider fatigue can be determined based, for example, on identified trends or changes in a quality of resuscitation activities being performed by the acute care provider, an amount of time that the acute care provider 704, 706 has been performing a particular activity, and/or a predetermined acceptable activity length. In some instances, fatigue can be calculated by comparing changes in differences between resuscitation parameter values measured by the device and target values. If the discrepancy between measured and target values increases, it may be an indication that resuscitation quality is decreasing and that the acute care provider is becoming fatigued. The augmented reality device controller can be configured to periodically or continually update fatigue bars 714 for the acute care providers 704, 706 as fatigue is identified and/or becomes more pronounced. In other examples, the bar 714 can be a representation of a quality of a resuscitation activity being performed by an acute care provider 704, 706. For example, the bar 714 can be filled by an amount representative of a percentage of resuscitation activities performed by the acute care provider which fall within a target range of acceptable resuscitation activity quality.

As in previously described examples, the lead acute care provider can perform a gesture recognizable by the augmented reality device to obtain additional information about a particular object or individual within his/her field of view. For example, as shown in FIG. 7, the acute care provider's hand 750 is visible pointing to the acute care provider 704 to obtain additional information about the acute care provider 704 and/or resuscitation activities being performed by the acute care provider 704. When the acute care provider 704 is selected, the dashboard 710 can be configured to display one or more new information boxes 720 for the acute care provider. For example, the pop up display(s) (not shown) can comprise information about the particular resuscitation activity being performed by the acute care provider. Such information may include, for example, elapsed time since the resuscitation activity commenced, time that the respective acute care provider has been performing the activity, time until the acute care provider should switch roles with another acute care provider, time until the activity should be ceased or paused (if known), and target resuscitation parameters for the activity being performed. The pop-up display can also include information about the acute care provider performing the activity, such as a graph showing changes in quality of resuscitation activity over time, a list of activities previously performed by the acute care provider during the rescue effort, and/or a list of activities that the acute care provider is scheduled to perform in the future. In some examples, the popup display can also include a real-time or substantially real-time video feed obtained from cameras of the selected acute care provider's augmented reality device to provide the lead acute care provider with a real-time record of what the selected acute care provider is seeing and doing. As in previously described examples, the lead acute care provider can close or minimize the popup display by performing a predetermined gesture, such as a swipe or by pointing to a particular portion within the field of view.

Virtual Instrument Box

Figure 8:
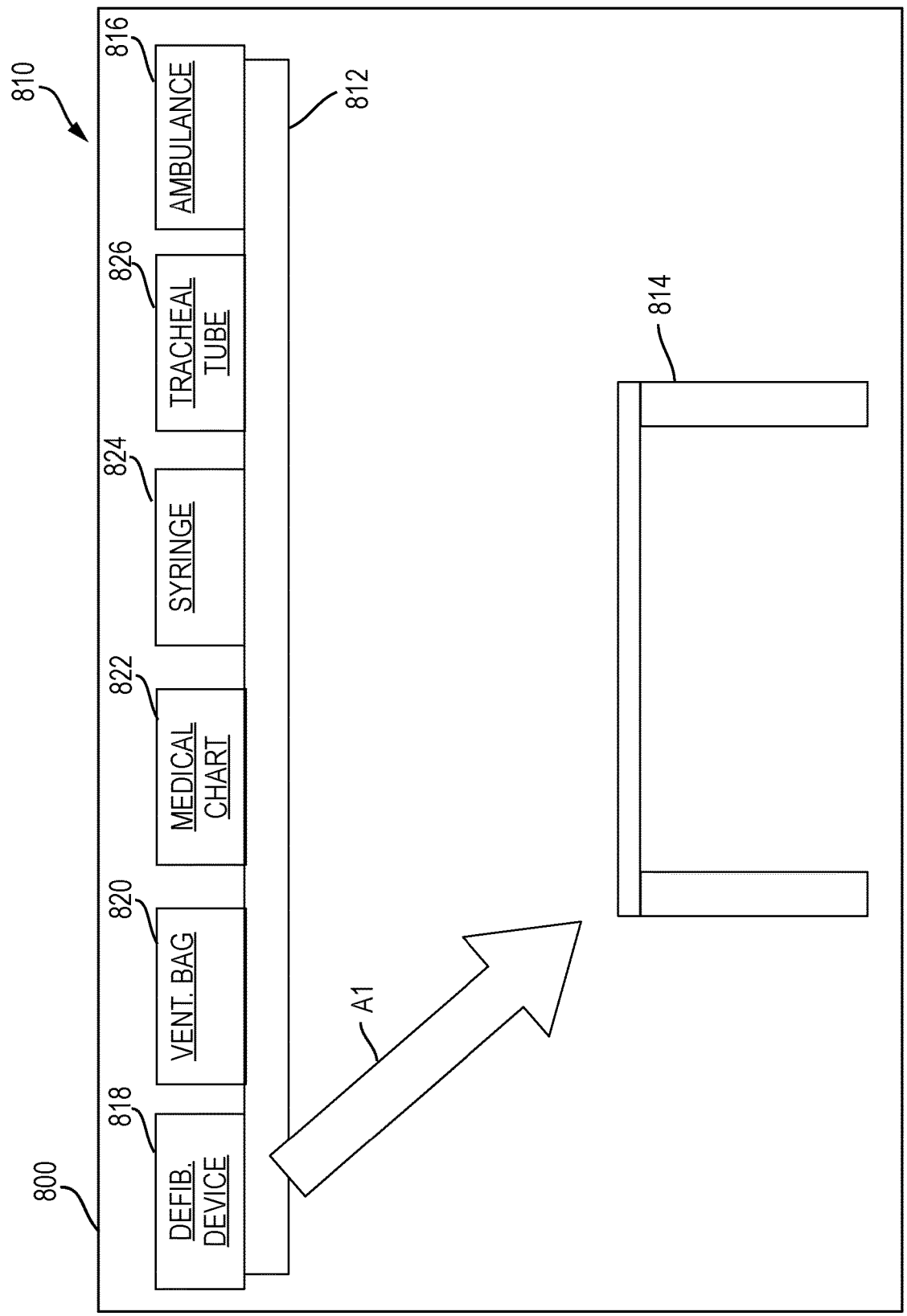
FIG. 8 shows another exemplary field of view perceived through an augmented reality device including a virtual instrument box that can be manipulated by an acute care provider.

As shown in FIG. 8, another exemplary field of view 800 for an acute care provider is illustrated. The field of view 800 includes an exemplary display for providing information about the patient, resuscitation activity parameters, and rescue effort to the acute care provider. Specifically, in the field of view 800, the previously described dashboard is replaced with a virtual instrument box 810 which is projected within the acute care provider's field of view.

Generally, the virtual instrument box 810 comprises a platform or shelf 812 with a plurality of icons representing different functions or tasks that can be performed at the rescue scene. The icons are dynamic and can be manipulated by the acute care provider by, for example, performing gestures such as pointing to, grasping, and dragging the icon to another location in the field of view 800. For example, the acute care provider may perform a gesture to drag an icon from the shelf 812 to a work bench 814 located at another location within the field of view 800 to indicate that the user is ready to set up and begin using the selected item or device. For example, as shown in FIG. 8, the user "selects" the icon or tool from the shelf by performing a drag and drop action, in which the user points to the icon, drags the icon across his/her field of view 800 in the direction of arrow A1 to the work bench 814, and then "releases" the icon on the work bench 814 by, for example, performing a hand opening gesture signifying that the icon has been selected for use. Once the icon is selected (e.g., dropped on the work bench 814), the augmented reality device can begin the selected process or program or display selected information within the acute care provider's field of view 800.

As shown in FIG. 8, the platform or shelf 812 is projected as extending across a top portion of the field of view 800. The icons are sitting on the platform or shelf 812 to indicate that the devices or tasks represented by the icons are available to be used by the rescuer. The icons on the shelf 812 can be static, meaning that options available to the acute care provider do not change as the rescue effort progresses. In other examples, the available icons on the shelf 812 can change based, for example, on patient status, an acute care provider's expertise or training, or on what devices and individuals are present at the rescue scene. For example, if an ambulance is available to transport a patient from the rescue scene to a hospital, then an ambulance or transportation icon 816 could be displayed on the shelf 812 to inform the acute care provider that this option is available. If patient transportation is not yet available at the rescue scene, then the ambulance icon 816 is not displayed on the shelf 812.

With continued reference to FIG. 8, the shelf 812 can also include a defibrillator icon, such as an icon 818 projected on a left side of the shelf 812. When the defibrillator icon 818 is selected (e.g., dropped on the work bench 814), the augmented reality device may display a series of screens with instructions for setting up the defibrillator. The platform or shelf 812 can also include a ventilation icon (such as a bag ventilator icon 820) which, when selected by the acute care provider, causes the augmented reality device to provide instructions for setting up and using a bag ventilator. The shelf 812 can also include an icon for a patient's medical chart 822 which, when selected, causes an electronic version of the patient's chart to be displayed. Other icons may include a fluid delivery device icon 824 (e.g., a syringe or IV bag), which can be selected to guide the acute care provider in providing a medical injection to a patient. For example, upon selection of the fluid delivery device icon 824, the augmented reality device may display a virtual image identifying a recommended fluid access site or vein for performing an injection. An exemplary field of view for guiding the acute care provider in determining vein location for performing an injection is shown in FIG. 13. In a similar manner, the augmented relativity device could also guide the acute care provider in using a syringe to draw blood from the patient. The shelf 812 may also include a tracheal tube icon 826 which, when selected, causes the augmented reality device to provide instructions for positioning the tube in the patient's trachea and/or provides confirmation of tube placement based on measurements from sensors associated with the patient and/or augmented reality device.

Virtual Data Input

Figure 9:
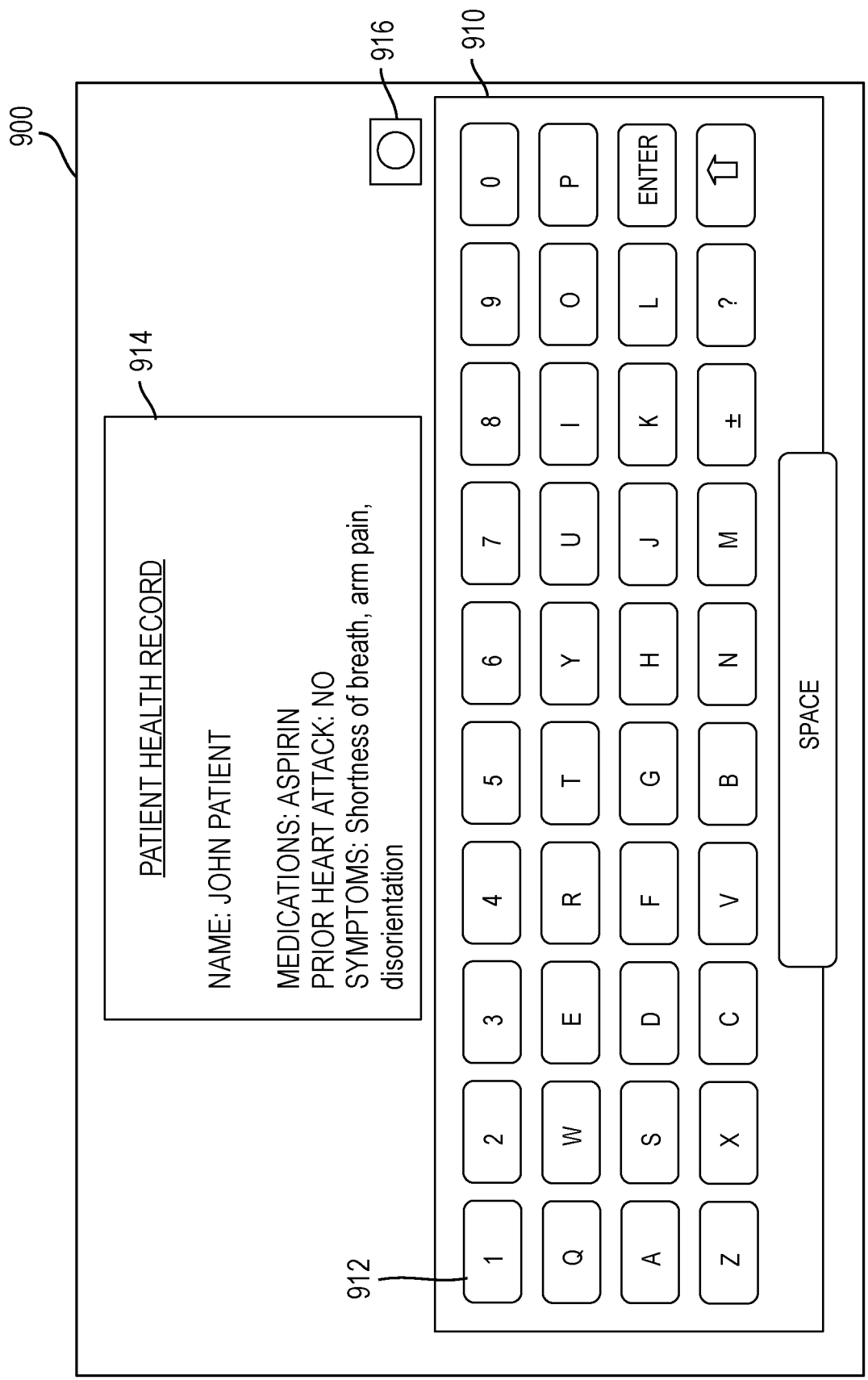
FIG. 9 shows another exemplary field of view through an augmented reality device including virtual data input features for use by the acute care provider.

FIG. 9 shows another exemplary augmented reality device field of view 900 for an acute care provider including features for virtual data input. The field of view 900 includes a virtual keyboard 910 for the user to enter information. The keyboard 910 can be laid out in standard QWERTY format or in any other order or arrangement. The acute care provider can select virtual keys 912 by pointing to a location of the projected keyboard 910 within the field of view 900. One use for a virtual keyboard 910 is when entering information about a patient. For example, the acute care provider may be responsible for entering certain information about the patient into a medical record. In that case, a virtual medical chart 914 may be projected within the field of view 900 above the keyboard 910. The virtual medical chart 914 can include some fields that are automatically completed by the augmented reality device. For example, the augmented reality device may be configured to receive certain physiological data from medical devices at the rescue scene, such as information about heart rate, AF burden, or similar physiological parameters which can be determined from a patient ECG. Such ECG parameters could be collected, for example, from a defibrillator connected to the patient. Oxygen saturation (e.g., pulse oxygenation) and ventilation parameters can be received from a ventilator or stand-alone oxygen saturation sensor. For information fields that cannot be filled in automatically, the acute care provider can select the information field and virtually "type" the information. For example, a physician or medical professional using the augmented reality device in a hospital setting could type notes during examination of a patient. In a similar manner, an acute care provider could type symptom information for the patient using the augmented reality device.

In another example, the information could be input by speaking rather than typing. For example, a record button 916 could be projected within the field of view 900. Upon pressing the record button 916, a microphone of the augmented reality device could begin recording the wearer's speech. The recorded speech could be automatically transcribed using automatic transcription software as is known in the art. The transcribed information could be saved in appropriate information fields of the patient medical record or stored with other related patient information for future review. In other examples, the field of view 900 could include other data entry icons including dials or knobs (not shown) for entering numerical values or ranges. In other examples, a user could virtually write notes using his/her finger on a virtual note pad displayed within the field of view 900. For example, the augmented reality device could be configured to extract or identify text as the user moves his/her hand or finger to form letters.

Examples for Guidance of Resuscitation Activities

In addition to displaying dashboards and collecting information about the patient or rescue effort, as discussed herein, the augmented reality device may also display images of a virtual object for providing emergency resuscitation guidance to the acute care provider in performing resuscitation activities. Exemplary fields of view for providing such guidance are shown in FIGS. 10-16B. These figures show that the augmented reality device can be configured to provide guidance in performance of resuscitation activities based on positioning and/or movements of the acute care provider and other individuals or objects present in images captured by the device. In some examples, the augmented reality device may process obtained three-dimensional information and images of the rescue scene, to determine which tasks need to be performed. Once a task is identified, the augmented reality device may apply spatially sensitive rules to generated three-dimensional representations of the rescue scene to determine types of guidance to be provided to the acute care provider including, for example, which types of virtual three-dimensional objects should be generated and positioned in the three-dimensional representation of the rescue scene, and where images of the virtual objects should be displayed on the visual display of the augmented reality within the acute care provider's field of view. In some instances, in accordance with spatially sensitive rules, once it is determined that the task was correctly performed, the displayed images of a virtual object can be suitably altered (e.g., disappear from the acute care provider's field of view or change appearance). Optionally, different images of a virtual object may then be displayed on the visual display of the augmented reality device, encouraging the acute care provider to continue the activity and/or perform another aspect of the resuscitation activity.

Electrode Placement

In one example, the augmented reality device and system can be used to assist the acute care provider in properly placing sensing or therapeutic electrodes (e.g., defibrillator electrodes, SpO$_2$ sensors, blood pressure sensors, ECG sensors, etc.) on a patient during set up of a resuscitation, defibrillation, or ventilation device.

Figure 10:
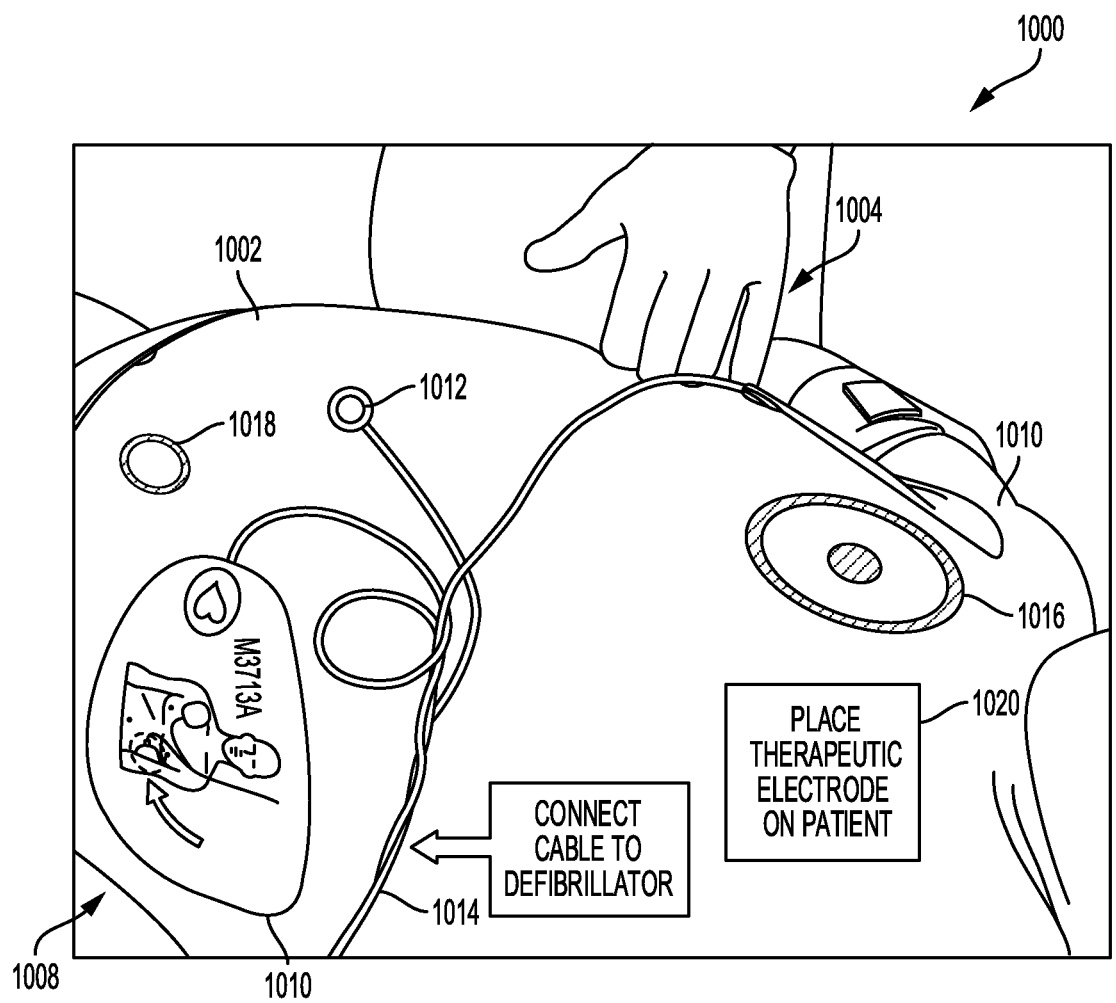
FIG. 10 shows an exemplary field of view through an augmented reality device during electrode placement.

Proper electrode placement is important for increasing or improving effectiveness of a defibrillation shock. Even small differences from preferred electrode positioning impacts an amount of electrical current provided to the heart and effectiveness of the shock treatment. Accordingly, the augmented reality device may generate one or more images of a virtual object indicating to the wearer where the electrodes (defibrillation and/or ECG sensing) should be placed on the patient. The augmented reality device may also provide audio feedback and/or haptic feedback when an electrode is placed according to a desired electrode placement position. FIG. 10 shows an acute care provider's field of view 1000 through an augmented reality device during electrode placement. As shown in FIG. 10, the acute care provider looking through the augmented reality device sees aspects of the rescue scene including, in relevant part, the patient 1002 (appearing as a physical object within the field of view 1000) and therapeutic electrodes 1010 and/or sensing electrodes (e.g., ECG sensing electrodes 1012) (also appearing a physical object) intended to be affixed to the patient's chest. The acute care provider is also able to view via the augmented reality device virtual objects, such as placement targets (e.g., shown as virtual electrodes that are presented on the visual display as virtual three-dimensional objects capable of interacting with the identified physical objects) that are located at the proper position and orientation at which the electrodes are to be placed (appearing as virtual image objects within the field of view). In some instances, therapeutic electrodes and ECG sensing electrodes can be provided together in a single electrode package, such as the package 110 (shown in FIG. 1). The acute care provider may also see, for example, the defibrillator 1008 and a cable 1014 extending from the defibrillator 1008 to the electrodes 1010. The acute care provider may also see other acute care providers 1004 at the scene, such as an acute care provider performing or preparing to perform ventilations.

In some instances, the controller may also be configured to confirm that a correct electrode type (e.g., an adult electrode or a pediatric electrode) is being positioned on the patient's chest. For example, the controller can be configured to determine, recognize, or detect whether the patient is an adult or child and whether the electrode being position on the patient is an adult or pediatric electrode. In some instances, identifying information about the patient can be manually provided by one or more acute care providers. For example, the acute care provider may manually input information about a patient dimensions, patient size, or patient age using the input features described in FIG. 9.

In other examples, the controller may determine patient dimensions or size based on analysis of the produced three-dimensional representation of the rescue scene and/or of images of the patient captured by cameras of the augmented reality device. The controller can be configured to determine what type of electrode is being used (e.g., adult, pediatric, pads only, pads plus compression sensor, therapy vs sensing electrodes) based on identifying information stored on or associated with an electrode assembly. For example, when an electrode assembly is connected to a medical device (such as a defibrillator), the defibrillator may download information about the electrode assembly (e.g., electrode type, age range, etc.) from computer readable memory of the electrode assembly. In other examples, the augmented reality device may be configured to automatically detect and extract information about the electrode assembly from labels, near field communication devices, bar codes, QR-codes, and other identifiers on or associated with the electrode assembly. In other examples, the controller may analyze images of the electrode assembly obtained as the electrode assembly is being positioned on the patient to identify the type and age range for the electrode assembly. In other examples, the user may manually enter information (such as a product ID number) using the data input features shown in FIG. 9. Once the patient information and electrode assembly type is known, the controller can confirm that the electrode assembly being positioned on the patient is appropriate for the patient and type of treatment being provided to the patient.

The augmented reality device can be configured to display virtual visual indicators in the visual field where the perspective and location, as well as persistence of perceptual co-location of the visual indicators and the anatomical locations on the surface of the patient, such that the displayed visual indicators appear to the provider to be "projected" onto the surface of the patient, and thereby assist the acute care provider in properly placing the electrodes 1010, 1012 on the patient 1002. For example, a placement target 1016—the "visual indicator"—is perceptually "projected" onto the patient's thorax having an outline that shows the acute care provider proper placement for the therapeutic electrodes 1010. In such an instance, if the patient's thorax moves within the field of view, the image of a virtual object shown to be on the thorax moves along with the thorax as if attached thereto in order to maintain indication of the proper placement location for the electrodes. The provider simply needs to align the real electrode they are holding in their hands as they are placing the electrodes on the real patient's chest with the virtual visual indicator in order to attain the preferred placement location and orientation of the electrodes. As noted above, for some embodiments, the placement target(s) may appear as virtual electrodes where the acute care provider intuitively aligns and overlays the actual electrodes with the virtual electrodes to achieve a proper placement orientation. It has been shown in studies (e.g., Resuscitation 61 (2004) 143-147, "Adherence to guidelines when positioning the defibrillation electrodes") that the accuracy of defibrillation electrode placement can be quite poor in actual clinical practice. Since the amount of therapeutic defibrillation current delivered to the heart can be altered by a factor of 3 or more (based, e.g., on teachings from "Effects of Paddle Placement and Size on Defibrillation Current Distribution: A Three-Dimensional Finite Element Model," Karlon, IEEE Transactions on Bio. Eng. Vol 40, No. 3, March 1993), electrode placement can have a significant impact on the defibrillation success rate. Therefore, an augmented reality system that interactively instructs the rescuer of defibrillation electrode placement may be of significant benefit to cardiac arrest victims.

In a similar manner, a placement target 1018 showing proper placement of the ECG sensing electrodes 1012 may also be displayed to the acute care provider. Similar to that for the therapeutic electrodes, the placement target 1018 may appear to the wearer as virtual ECG sensing electrodes where the objective would be for the actual ECG sensing electrodes 1012 to be aligned with the virtual electrodes in position and orientation. In this example shown in FIG. 10, the ECG sensing electrode is a limb lead, though, it can be appreciated that other appropriate placement locations (e.g., left arm limb lead, right arm limb lead, left leg limb lead, right leg limb lead, and V-leads positions) may also be presented by the augmented reality device. In some embodiments, the same electrodes (e.g., defibrillation electrode pads) used for providing therapy to the patient may also be used to sense ECG, and so the virtual object may be generated on the augmented reality device accordingly.

The placement targets 1016, 1018 may comprise text, images, icons, or similar indicators to inform the acute care provider of proper electrode placement. The acute care provider can be instructed to apply the electrodes 1010 to the patient 1002 at the location indicated by the projected placement target(s) 1016, 1018. Textual instructions 1020 can also be projected within the acute care provider's field of view 1000. For example, text guiding the acute care provider through the process for setting up the defibrillator 1008 and electrode 1010 placement can be displayed in the acute care provider's field of view 1000. Exemplary text instructions 1020 may include an instruction to "Place therapeutic electrodes on patient," "Place ECG sensing electrodes on patient" and "Connect cable to defibrillator." In some instances, the augmented reality device can process captured images to determine when a particular task has been completed. Once confirmation is received that the task has been completed, the augmented reality device can provide a text instruction 1020 instructing the acute care provider to perform a next activity. In other examples, instructions can be provided audibly through the augmented reality device speakers.

In use, the acute care provider may obtain the electrode(s) 1010, 1012 or electrode package from a storage location, such as from the ambulance or from a compartment of the defibrillator 1008. The controller and/or augmented reality device can identify that the acute care provider is holding an electrode package and that guidance should be provided for placement of the electrodes for the patient. As described above, the augmented reality device and/or controller can also be configured to identify a type of electrode(s) or electrode package (e.g., type, size, pediatric or adult) being held by the acute care provider based on either information stored on the electrode package or analysis of images of the electrode package. In a similar manner, the controller and/or augmented reality device can determine whether the type of electrode package is an appropriate size based on a manually entered or estimated age of the patient (e.g., either adult or pediatric). The device and/or controller then identifies the position of the patient's chest in the two- and/or three-dimensional representation(s) of the rescue scene where the electrode assembly should be placed. Information about placement of the electrode assembly can be based on patient size and the type of electrode assembly being held by the patient. For example, a pediatric electrode assembly may be a smaller package configured to be positioned in a central portion of the chest. An adult electrode assembly can be larger and have the z-shaped configuration shown, for example, in FIG. 1. Once the type of electrode assembly and patient's position are identified, the controller can cause the augmented reality device to display the visual indicators such as the placement targets 1016, 1018 on the patient's chest. The controller and/or augmented reality device can select or modify the images displayed to the acute care provider to provide guidance for the type of electrode assembly being positioned on the patient, so that the electrode assembly is correctly aligned and positioned for the patient. Text 1020 instructing the acute care provider to place the electrodes 1010, 1012 in the identified location can also be displayed to provide additional visual guidance for the acute care provider. As the acute care provider is positioning the electrodes 1010, 1012, the augmented reality device can be configured to continue to obtain information and images representative of the acute care provider's field of view 1000 and to offer guidance if the acute care provider appears to be performing in an incorrect manner. The guidance provided by the augmented reality device is desirably interactive guidance showing the acute care provider where the electrodes 1010, 1012 should be placed. Interactive guidance can include a color change in the virtual electrode assembly, a textual message in the field of view, or a graphical indication of whether the electrode assembly is properly placed.

In some examples, a shape or appearance of the placement targets 1016, 1018 can be modified based on how close the electrode assembly is to the desired position. For example, the placement targets 1016, 1018 may begin to flash or may become darker or more conspicuous as the electrodes 1016, 1018 are moved close to the desired position. In other examples, the placement targets 1016, 1018 can move through the acute care provider's field of view showing the acute care provider where the electrodes 1010, 1012 need to be moved to. Once an image showing the electrode(s) 1010, 1012 or electrode package affixed to the patient 1002 in the identified location is obtained by the augmented reality device, the controller and/or augmented reality device can be configured to emit an indication to the acute care provider confirming that the electrode(s) 1010, 1012 or electrode package have been positioned correctly. For example, the augmented reality device can display text 1020 stating that the electrodes 1010, 1012 have been correctly placed. In other examples, the augmented reality device can provide an audible confirmation, such as a positive sound (e.g., notes comprising a major chord) to confirm proper electrode 1010, 1012 placement for the acute care provider. If the acute care provider places the electrodes 1010, 1012 on the patient's chest in an incorrect position, the augmented reality device can provide negative feedback to inform the acute care provider that the electrodes 1010, 1012 are not positioned correctly. Negative feedback can include text or visual images alerting the acute care provider about the improper placement. Feedback can also include audio or vibration notifications alerting the acute care provider of the problem.

Guided Palpation of Body Regions

In another example, the augmented reality device can be used for providing guidance during palpation of the patient. For example, guided palpation can include showing the acute care provider where his/her hands should be placed on the patient. Guidance can also include displaying or providing messages about what structures or abnormalities the acute care provider should feel at different hand positions. In order to provide such guidance, the augmented reality device can be configured to identify anatomical features of a patient in the generated three-dimensional representation of the rescue scene. For example, an anatomical feature of the patient can include at least one of a sternum, a sternal notch, an axilla, ribs, an anterior portion of the patient, and a posterior portion of the patient. Based on positions of the identified anatomical features, the augmented reality device can position and manipulate virtual objects in the three-dimensional representation of the rescue scene to provide guidance for the acute care provider.

Figure 11:
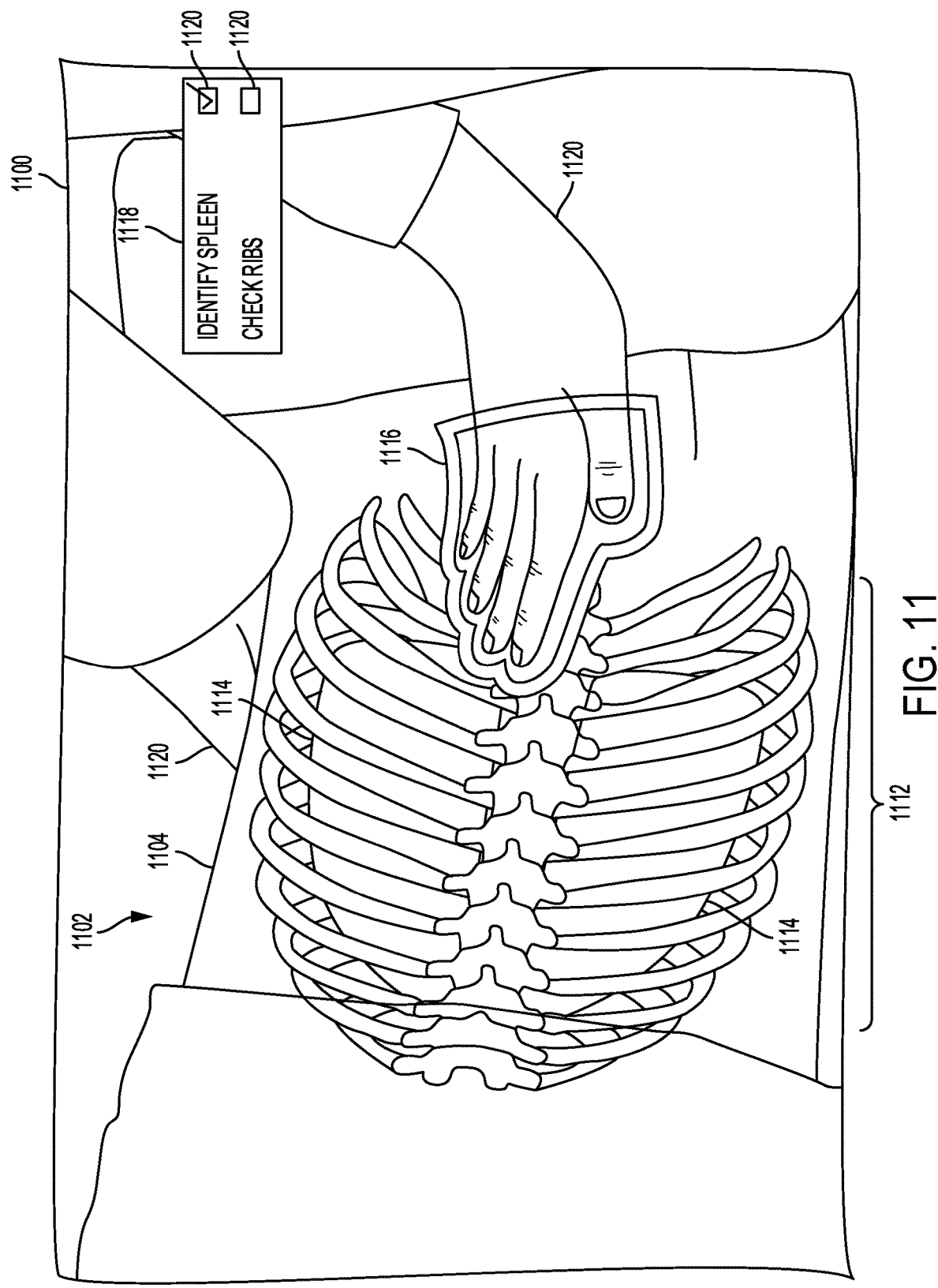
FIG. 11 shows an exemplary field of view through an augmented reality device during guided palpation of different body regions of a patient.

FIG. 11 shows an exemplary field of view 1100 of the acute care provider perceived through the augmented reality device as guided palpation of different portions of the patient 1102 are being performed. In general, palpation is used to identify injuries, abnormalities, and other problems that a patient may be experiencing. In order to assist the acute care provider in palpating the patient 1102, the augmented reality device can virtually display certain anatomical landmarks within the field of view 1100, where the perspective and location, as well as persistence of perceptual co-location of the anatomical landmarks and the actual anatomical locations on the surface of the patient, such that the displayed anatomical landmarks appear to the provider to be "projected" onto or into the surface of the patient. For example, anatomical landmarks could comprise three-dimensional bone structures 1112 appearing to be projected onto or into portions of the patient's body. In other examples, virtual images of organs 1114 or tissues could be displayed, such that they appear to be projected into the interior volume of the patient's body, e.g. the heart appears to be inside the patient's thorax, in the visual field such that the perspective and location, as well as persistence of perceptual co-location of the visual indicators and the anatomical locations on the surface of the patient, such that the displayed visual indicators appear to the provider to be "projected" onto the surface of the patient. In particular, virtual images of structures that the user should be feeling based on a detected position of the user's hands. In some examples, the augmented reality device may guide a user through guided palpation of the patient 1102 examining body regions of particular interest for a trauma patient as shown in FIG. 11.

The field of view 1100 for guided palpation may further comprise displaying a virtual hand outline 1116 projected overlaying the patient 1102 to guide the acute care provider in correct hand position while palpating the patient 1102. The user may be instructed to match his/her hand position with the position of the virtual hand outline 1116 and, in particular, to move his/her hands across the patient's body as guided by the virtual hands 1116. The field of view 1100 can further comprise instructions, such as text messages 1118, informing the acute care provider about what anatomical structures he/she should be feeling based on detected hand position. For example, as shown in FIG. 11, the acute care provider's hands 1120 are resting on a side and back of the patient's abdomen 1104. In this position, an instruction to feel for certain internal organs (e.g., spleen, lungs, etc.) can be projected within the field of view 1100 to inform the acute care provider that he/she should be attempting to identify such structures during palpation. In this hand position, the acute care provider may also be able to feel injuries, such as broken or cracked ribs, puncture wounds, and similar trauma. The acute care provider can confirm that he/she has identified the anatomical structure of interest by selecting a virtual confirmation button 1120 located near the text message 1118. In other examples, the acute care provider may confirm that he/she has identified the structure of interest verbally (e.g., by speaking a phrase such as "spleen position confirmed" or "no broken ribs identified"). The speech can be recorded by the microphone of the augmented reality device and included in the patient's medical record or in a report generated for the rescue event.

Vein Location/Position of IV Line

Figure 12:
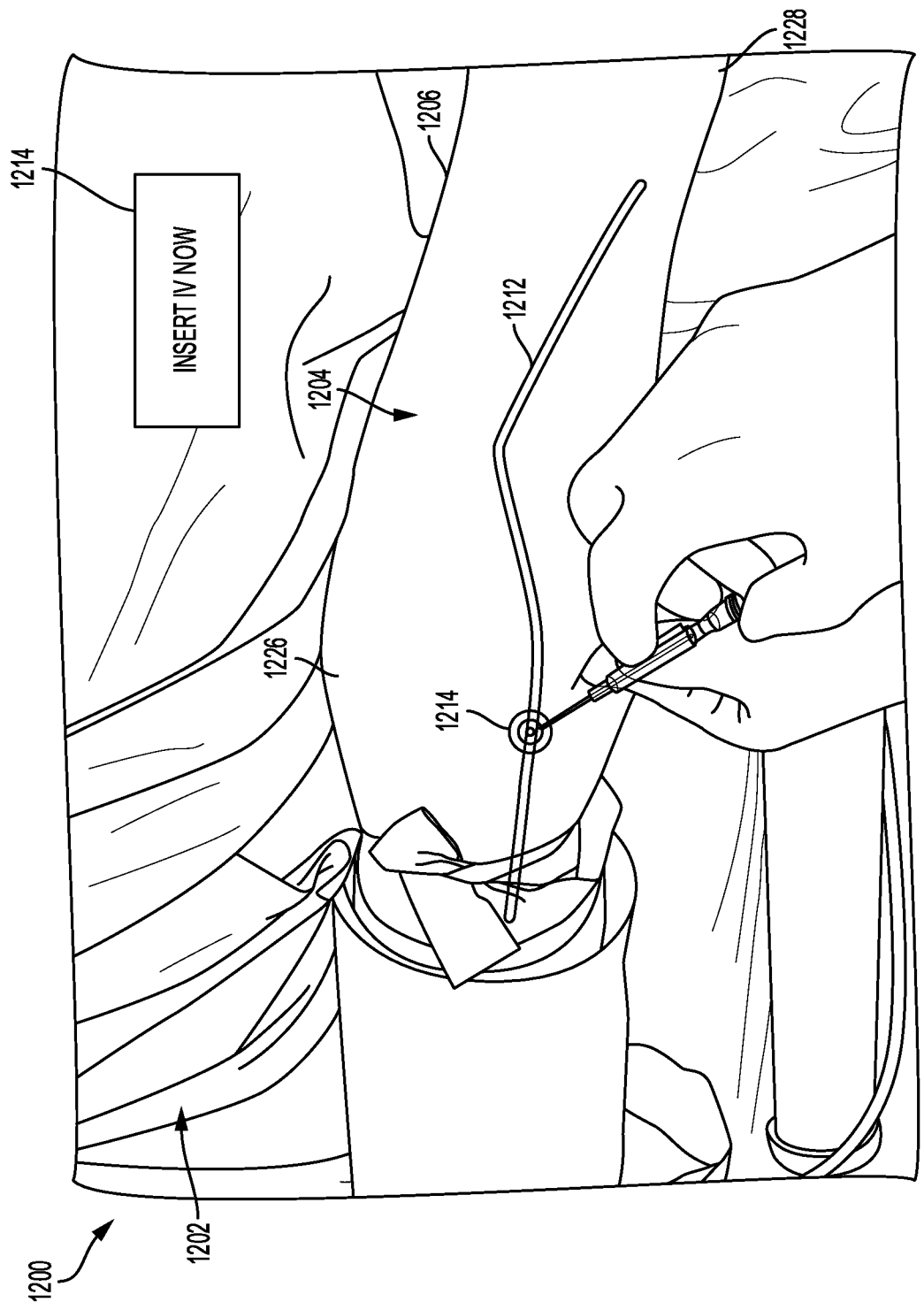
FIG. 12 shows an exemplary field of view through an augmented reality device during vein location and/or insertion of an IV line to a patient according to an aspect of the disclosure.

In some examples, the augmented reality device may also provide guidance for accessing a vein or performing an injection to a patient 1202. For example, the augmented reality device may provide a notification 1214 when an injection or intravenous fluid delivery should be performed for the patient, provide guidance about a preferred injection location on the patient's body, and record information about the injection, such as time of injection, medication concentration, fluid volume of injection, and other relevant factors. An exemplary field of view 1200 for an acute care provider perceived through an augmented reality device during insertion of a needle into the patient's vein as occurs, for example, while setting up an IV line is shown in FIG. 12. The field of view 1200 includes a virtual path or trace 1212 overlaying a suitable vein for the injection. The field of view 1200 can also include an icon 1214 identifying a preferred vascular access site. As shown in FIG. 12, the preferred access site can be at a convenient location, such as on the underside 1204 of the patient's arm 1206. Other usable injection sites include locations on the scalp, hand, foot, or leg.

In some examples, the augmented reality device is configured to analyze images of the patient 1202 captured by the camera to identify preferred veins and vascular access site. For example, the augmented reality device may process images using color correction or color enhancement techniques to distinguish veins from other portions of the captured image, such as by substantially increasing blue and/or violet contrast in captured color images to distinguish veins from skin tones. In other examples, infrared or ultrasound imaging techniques can be used to identify vein position. Once veins are identified in captured images, the augmented reality device may select a vein for using in the vascular access procedure based, for example, on accessibility, size, or other parameters. The augmented reality device can then map the location of the vein in captured images and, based on positioning information from the captured images, display the virtual path or trace 1212 in the field of view 1200 overlaying the patient 1202 (e.g., overlaying the underside 1204 of the arm 1026 as shown in FIG. 12). In a similar manner, the preferred location for the injection is identified by analysis of the captured images and displayed in the field of view 1200. For example, the preferred injection site (e.g., a location on the inner side of the patient's lower arm) can be identified by processing captured images to identify anatomical markers (e.g., the elbow 1226, wrist 1228, hand, or fingers (not shown)) and determining a location of the preferred injection site based on the position of the identified anatomical markers.

Chest Compressions

Figure 13A:
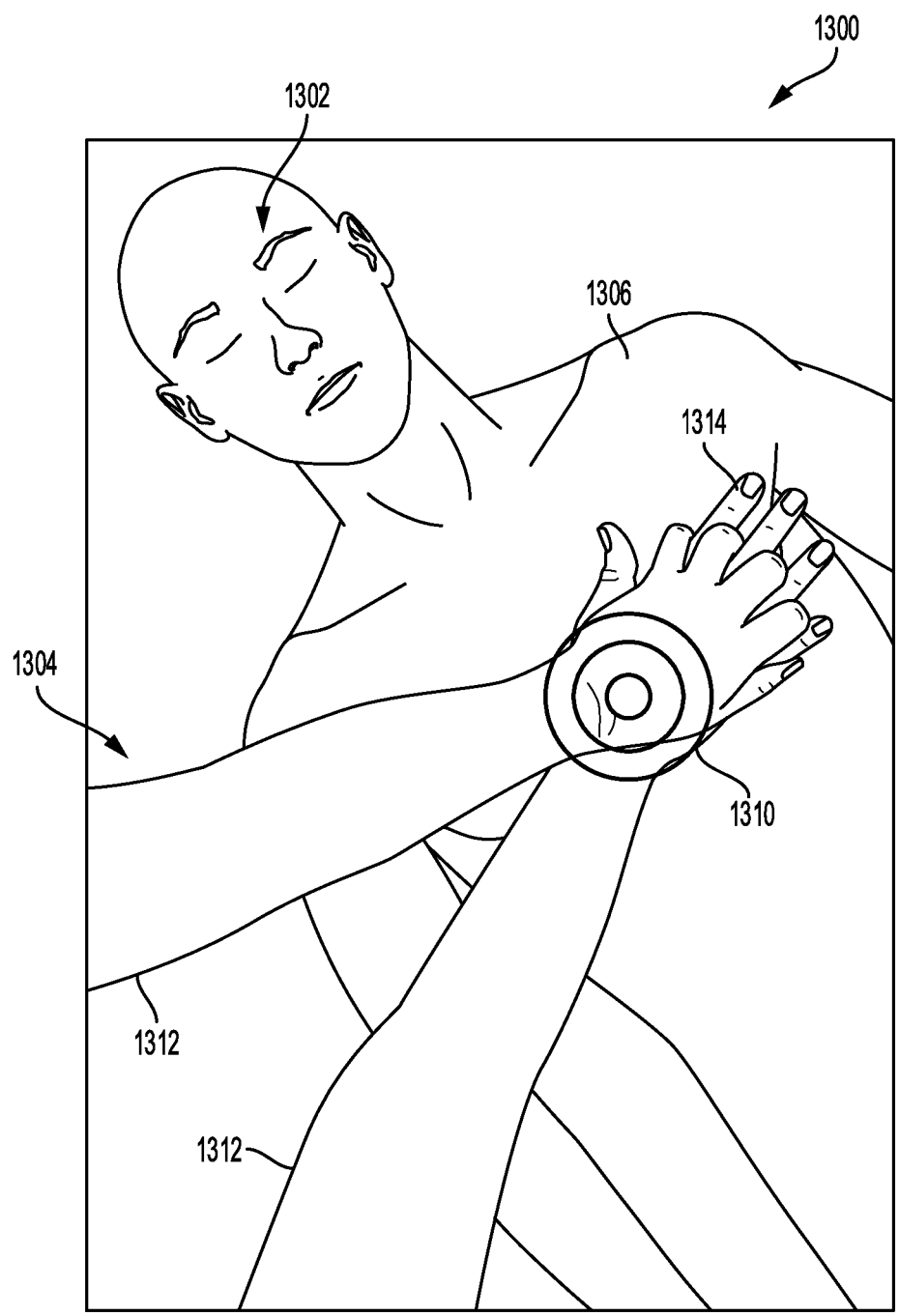
FIGS. 13A and 13B show exemplary fields of view through an augmented reality device during chest compressions for providing guidance about hand and arm positioning according to an aspect of the disclosure.
Figure 13B:
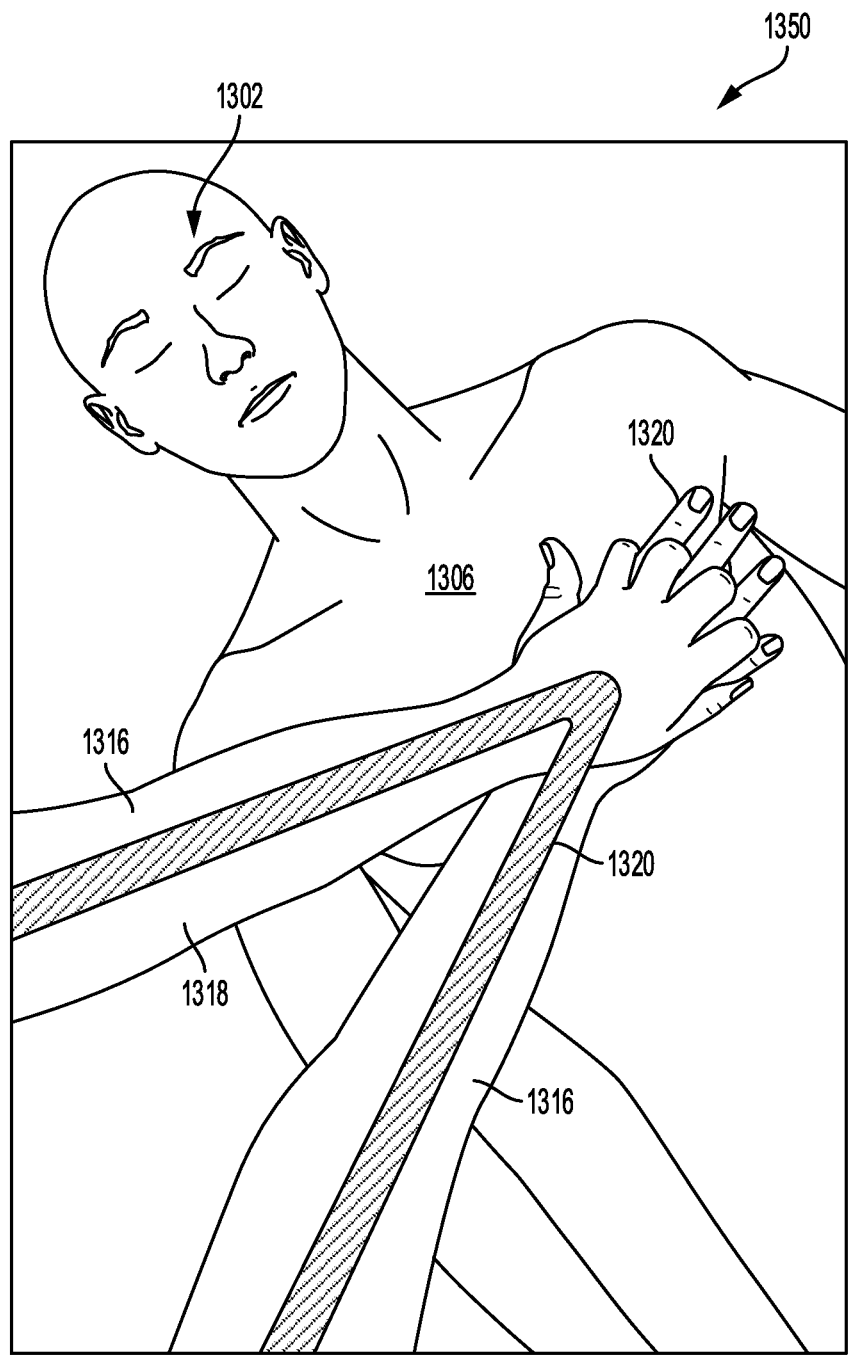
Figure 13C:
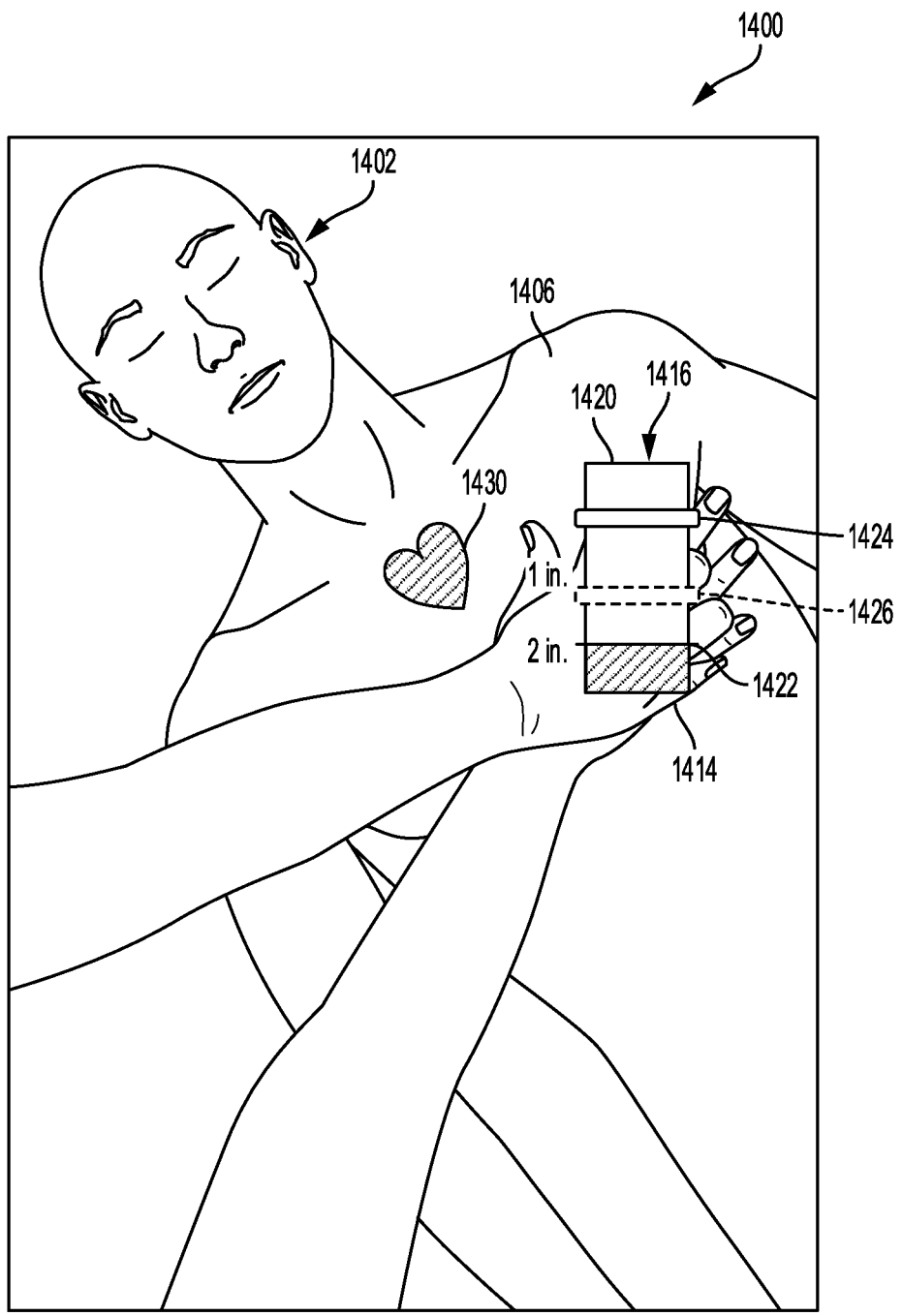
FIG. 13C shows an exemplary field of view through an augmented reality device during chest compressions and including a visual indicator in the form of a depth meter.

FIGS. 13A, 13B, and 13C show fields of view perceived by an acute care provider while performing chest compressions. The fields of view can include images of a virtual object, such as visual indicators which provide feedback about the quality of chest compressions being performed, guidance for performing chest compressions in accordance with a predetermined treatment protocol, as well as other relevant information about the rescue effort, patient 1302 or rescue scene. As discussed herein, in some examples, additional feedback can be provided in the form of an interactive or dynamic dashboard display, as described in FIGS. 6A and 6B.

As shown in FIGS. 13A and 13B, the acute care provider 1304 is shown kneeling adjacent to the patient's torso 1306 with arms 1312 stretched toward the patient 1302 preparing to begin chest compressions. An image of a virtual object, such as a target 1310, is displayed on the patient's sternum showing the acute care provider where his or her hands 1314 should be placed. Even if the wearer moves his/her head so that the field of view through the augmented reality device shifts, the target 1310 remains at the patient's sternum. In some examples, as shown in FIG. 13A, the target 1310 can be a simple icon, such as a projected circle, bullseye, or highlighted region, which appears to be resting on the patient's chest. In other examples, the target 1310 is an image, such as an image of a hand showing correct hand positioning and orientation. The target 1310 on the sternum may continue to be displayed until the augmented reality device determines that the acute care provider's hands 1314 are correctly positioned. Once the augmented reality device determines that the acute care provider's hands 1314 are correctly positioned, the target 1310 can disappear from the field of view 1300. Alternatively, the target 1310 may remain in the field of view 1300 as chest compressions are being performed. For example, the target 1310 may be shown overlaying or partially overlaying the acute care provider's hands 1314. Further, the target 1310 may change color or provide some other indication to inform the acute care provider that the hands 1314 are properly placed. In some instances, the augmented reality device may also provide audio or vibration feedback to confirm when the acute care provider's hands 1314 are correctly positioned. For example, the augmented reality device may emit a positive sound (e.g., three notes forming a major chord) when correct placement occurs. The augmented reality device may emit a warning or negative sound (e.g., three notes forming a minor chord) when the hands 1314 are placed incorrectly. Vibration feedback in the form of a vibrating or a buzzing sensation may also be provided to inform the acute care provider of incorrect hand placement.

As shown in FIG. 13B, a field of view 1350 including images of a virtual object is illustrated displaying appropriate arm 1316 position for performance of chest compressions. In high quality chest compressions, the acute care provider keeps his/her arms 1316 in a substantially straight position with the elbows 1318 locked. The acute care provider generally positions over the patient 1302, such that the acute care provider's weight contributes to the force of the compression. In general, during high quality compressions, the arms 1316 move in a substantially vertical direction (e.g., a direction normal to the patient 1302). In order to help the acute care provider to appreciate correct arm and shoulder orientation, arm positioning lines 1320 are displayed in the field of view 1350. For example, the positioning lines 1320 can comprise a straight line showing a correct position of the bicep connected to another line showing a correct position of the forearm. In some instances, the positioning lines 1320 can be replaced with projected images of a human arm at a correct position. The acute care provider can be instructed to try to align his/her arms 1316 with the line or image of the human arm during performance of chest compressions. In some examples, the augmented reality device can cause the positioning lines 1320 to move in a coordinated manner with the acute care provider, showing correct direction, arm position, and rhythm for high quality chest compressions.

In some examples, the augmented reality device may monitor chest compression quality by determining how closely the acute care provider's arm position matches the position of the projected positioning lines 1320. Further, the augmented reality device may emit an alert or notification if the acute care provider's arm 1316 position substantially deviates from the positioning shown by the positioning lines 1320. In some examples, the alert or notification can be a visual alert. For example, the positioning lines 1320 may flash a warning color, such as red or orange, to signal to the acute care provider that his/her movement direction and/or arm position during chest compressions does not conform to expected or preferred positioning. In other examples, arrows or other virtual objects may be projected into the field of view 1350 as an indication to adjust position. For example, arrows may be displayed to instruct the acute care provider to slide toward the patient 1302 (e.g., move closer to the patient's torso) if the acute care provider is not close enough to the patient 1302 for his/her arms 1316 to remain vertical during compressions. Alternatively or in addition, the augmented reality device may emit audio or vibration feedback to draw the acute care provider's attention to the fact that he/she is not following the positioning lines 1320.

FIG. 13C shows another exemplary field of view 1400 through an augmented reality device for an acute care provider performing chest compressions for a patient 1402 including a CPR guidance indicator 1416 which is projected over the acute care provider's hands 1414 as chest compressions are being performed. As shown in FIG. 13C, the acute care provider is performing chest compressions on the patient's chest 1406 and is looking in a downward direction at the CPR guidance indicator 1416. It has been determined that maintaining correct head position is an important aspect in performance of quality chest compressions. It is believed that encouraging the acute care provider to focus on his/her hands 1414 will help the acute care provider to maintain a consistent head position. It has also been determined that focusing the acute care provider's attention downwardly contributes to quality chest compressions by encouraging the acute care provider to exert force of his/her body weight to each compression.

The CPR guidance indicator 1416 can be an icon providing feedback about chest compression depth and rate. In some examples, the icon can comprise a gauge, such as a circular or linear gauge 1420, indicating compression depth compared to a target value. For example, the gauge 1420 can include a target line or region 1422. The acute care provider can be instructed to continue pushing downwardly on the patient's chest 1406 until an indicator line 1424 of the gauge 1420 reaches the target region 1422. If the acute care provider releases the compression before reaching the target depth, the gauge 1420 may flash or change color to signal the incorrect compression. In a similar manner, the gauge 1420 may flash or change color if the acute care provider compresses the chest below the target depth. In some examples, the gauge 1420 may also include an icon showing a target compression rate, such as a moving target line 1426 moving at a target compression rate. The acute care provider can be instructed to attempt to match his/her compression speed and rhythm to the guidance target line 1426. If the compressions are being performed too slowly, the target line 1426 may flash or turn color (e.g., turn from white to green) to indicate to the acute care provider that he/she needs to accelerate or speed up compressions. If the acute care provider is performing compressions too quickly, the target line 1426 may flash according to a second pattern or turn a different color (e.g., red or orange) to indicate to the acute care provider that he/she should slow down.

The augmented reality device may also provide audio and/or vibration feedback to supplement the visual indicators described herein. For example, the augmented reality device may emit a positive sound to confirm for the acute care provider that the compression has reached a target depth. The augmented reality device may also emit a negative or warning sound if the compression is released prior to obtaining the target depth or if the compression is too deep.

While a gauge 1416 is described herein and shown in FIG. 13C, other visual indicators can also be projected to the acute care provider's field of view 1400 by the augmented reality device to provide feedback about compression depth and rate. For example, the image of a virtual object could be a movable piston shown to be on the acute care provider's hands 1414 which moves in conjunction with compression of the patient's chest 1406 or torso. In other examples, the image of a virtual object may comprise a compressible ball that appears to be squeezed as compression depth increases. The acute care provider may be instructed to begin releasing the chest compression once the ball appears to be fully compressed. The ball can appear to expand toward a spherical shape as the compression is being released, which is representative of expansion of the chest when compression pressure is removed. When the ball returns to its spherical uncompressed state, the compression is fully released.

In other examples, as shown in FIGS. 2B-2E, the image of a virtual object for chest compression guidance can be an image, such as a cartoon image or informal line drawing, of a heart that appears to compress and expand in a coordinated manner with compressions performed by the acute care provider. In such embodiments, expansion and compression of the heart icon is intended to visually demonstrate to the acute care provider that the compression action drives blood from the heart to increase perfusion.

In some examples, the field of view 1400 further comprises virtual images comprising a performance indicator 1430 for providing feedback about a quality of chest compressions performed. The performance indicator 1430 can be a visual representation of the effectiveness or impact of resuscitation activities being performed on the patient 1402. While not based on actual measurements of blood flow or perfusion, a performance indictor 1430 aims to provide a visual summary of therapeutic effects of resuscitation, such as flow of oxygenated blood caused by the resuscitation activities being performed. The performance indicator 1430 can be based on parameters including compression depth, compression rate, compression release, ventilation volume, ventilation rate, and ventilation pressure. As one or more of the parameters improves (e.g., more closely matches target value(s)), the performance indicator displays an indication of positive performance of resuscitation activities. If the difference between the target values and measured values increases, the performance indicator signals a decrease in quality of resuscitation activities being performed.

The performance indicator 1430 can comprise a shape displayed to the acute care provider by the augmented reality device, such that it appears to be projected on or overlaid on the patient's chest or thorax 1406, possibly adjacent to or just above the location of the patient's heart. As described above, the indicator 1430 is not actually "projected" onto the patient's chest 1406. Instead, it appears to be "projected" on the chest 1406 because of how is the image is displayed to the acute care provider by the augmented reality device. The shape can be an easily recognizable geometric shape (e.g., a square, triangle, rectangle, or a heart shape), as shown in FIG. 13C. In other example, the shape can be a cartoon image of an organ or body structure, such as an image of a human heart or lungs. When measured performance of resuscitation activities is particularly poor, the shape outline is completely empty or, in the case of an image of an organ, the image may be faint or disappear completely. As measured quality of resuscitation activities improves, the shape outline is filled in. If the shape is completely filled, it signifies that the resuscitation activities being performed for the patient are of good quality. Exemplary performance indicators (referred to as a perfusion performance indicator) that could be displayed to a user by the augmented reality device disclosed herein, are described in U.S. Pat. No. 7,650,181 entitled "Synchronization of repetitive therapeutic interventions," and in U.S. Pat. No. 8,880,166, entitled "Defibrillator Display," both of which are hereby incorporated by reference herein in their entireties. Alternatively or additionally, the performance indicator can be represented as a number, for example, a "5" on a scale of 1 to 10, where "10" is the target for adequate CPR. For example, a number "5" can correspond to a shape being half filled. A number "10" can correspond to the shape being entirely filled in.

In some examples, the performance indicator 1430 provides information about the overall effects of resuscitation activities on the patient 1402. In other examples, the performance indicator 1430 may provide information about effects of treatment activities for specific organs or body regions. The acute care provider may select which body region(s) are being considered by the performance indicator 1430 by moving the indicator to different positions on the patient's body. For example, a performance indicator 1430 on the patient's thorax or chest 1406 can consider effects of ventilation and chest compressions on perfusion of oxygenated blood to the lungs and/or heart. In another example, a performance indicator 1430 is shown, which represents that oxygenated blood is delivered to the patient's brain and visually displays effects of the oxygenated blood to the brain. For example, if the acute care provider becomes aware that the patient 1402 may be suffering from a traumatic brain injury (TBI), in which case brain blood flow would be especially relevant for treatment, the acute care provider can perform a gesture causing a performance indicator 1430 for brain blood flow to be displayed. A performance indicator 1430 for brain blood flow would consider parameters, such as frequency of ventilations, end tidal $CO_2$, frequency and depth of compressions, and similar parameters to estimate whether blood flow to the brain is below normal, acceptable, or elevated. If TBI is suspected or diagnosed, the acute care provider may take steps to avoid elevated blood flow to the brain to avoid brain injury. In other examples, the acute care provider may select an extremity (such as an arm or leg) causing a performance indicator for the selected extremity to be displayed. In a similar manner, the acute care provider can cause a performance indicator to disappear by, for example, performing a swipe gesture.

Visual Representations Generated Based on Medical Image Data

Figure 14:
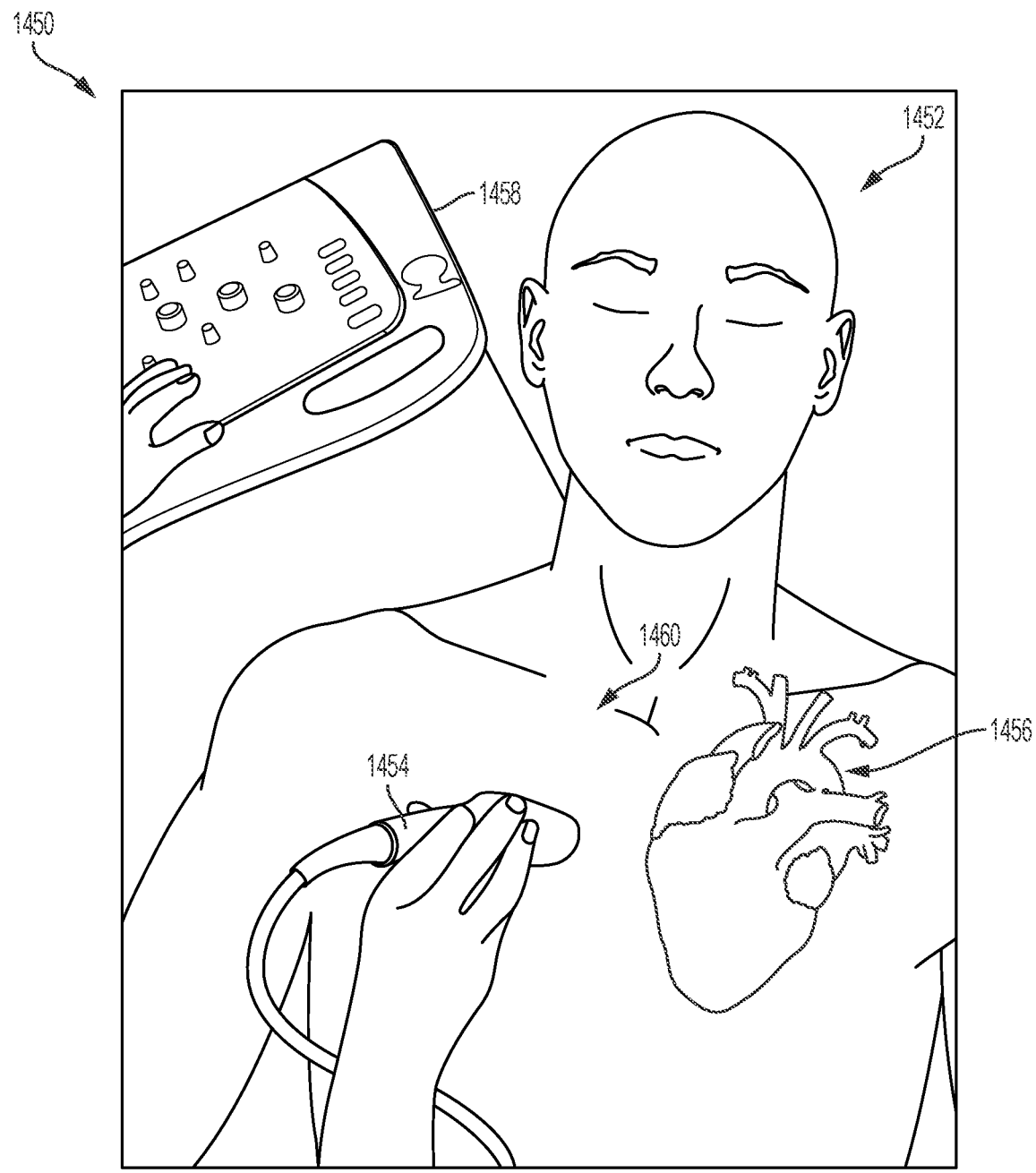
FIG. 14 shows an exemplary field of view through an augmented reality device showing a virtual representation of an organ displayed based on information from an ultrasound transducer.

FIG. 14 shows a field of view 1450 perceived by an acute care provider wearing the augmented reality device (not shown in FIG. 14). As in previous examples, the field of view 1450 comprises images of virtual objects, for example, which may provide feedback and/or guidance for performing resuscitation activities (e.g., chest compressions, ventilations, diagnostic activities, etc.), as well as other relevant information about the rescue effort and a patient 1452. Unlike in previous examples, in which a location of the virtual objects was largely determined based on information sensed by the augmented reality device, the augmented reality device worn by the rescuer in FIG. 14 is in wired or wireless communication with a medical imaging device or probe. The medical imaging device or probe can be configured to perform various radiological imaging techniques and, for example, can be configured to use one or more of ultrasound, infrared radiation, x-ray, sonography, and similar imaging techniques to detect medical images of anatomical or internal body structures of the patient 1452. For example, the probe can be a hand-held ultrasound probe 1454 connected to an ultrasound imaging device 1458, as shown in FIG. 14. The probe 1454 can be configured to detect, identify and characterize internal body structures of the patient 1452 including, for example, organ(s), soft tissue(s), bone(s), muscle(s), blood vessel(s), a fetus, and other anatomical structures. In one example, information from the hand-held probe 1454 is used to detect a position, orientation, and size of a patient's heart, so that the visual representation generated for the user to view through the augmented reality device may reflect the information collected from the probe 1454. Accordingly, as discussed in more detail below, the information gathered from the probe 1454 coupled with the view of how the probe 1454 is positioned and oriented, as gathered from the augmented reality device, may provide for a more accurate visual representation by the augmented reality device of the internal object (e.g., heart, organ) and its location within the body of the patient 1452.

In some examples, information collected from the probe 1454 can be used to display and adjust a representation of virtual objects within the field of view 1450. Information collected by the probe 1454 can also be used to help guide the rescuer in providing treatment for the patient. In order to collect information (e.g., image data) using the probe 1454, a user, such as the acute care provider wearing the augmented reality device or another acute care provider at the rescue scene, moves the probe 1454 over portions of, for example, a torso 1460 of the patient 1452 to capture image data of internal body structures in the patient's cardiothoracic region. For example, the user may move the probe 1454 in an up/down or back/forth pattern across the torso 1460 to capture images of the entire cardiothoracic cavity and the organs contained therein. In some examples, visual indicators guiding the user in positioning and movement of the probe 1454 can also be displayed within the field of view 1450. For example, arrow(s) could be generated and displayed in the field of view 1450 showing the user where to move the probe 1454. Images captured by the augmented reality device can be used to confirm that the user moves the probe 1454 to the identified locations on, for example, the patient's torso 1460. In other examples, portions of the torso 1460 could be highlighted or identified, showing the user where the probe 1454 should be positioned.

As described previously, during the rescue effort, the augmented reality device collects three-dimensional image information for the rescue scene to generate a three-dimensional representation of the scene. Based on analysis of the generated three-dimensional representation, the processor of the augmented reality device is configured to identify and track a location and orientation of objects at the rescue scene, including, for example, the imaging probe 1454 as it is being moved over the patient 1452. For example, the processor of the augmented reality device can be configured to detect a position and orientation of the probe 1454 relative to the patient 1452 as the probe 1454 is moved across the chest or torso 1460 of the patient 1452.

The processor is also configured to receive image data from the probe 1454, as it is being moved around the patient's torso 1460, and to associate the received image data of the probe 1454 with a specific location within the virtual three-dimensional representation when the image data was captured. In this way, the processor of the augmented reality device is able to more accurately determine where internal body structures, such as organs, bones, muscles, soft tissues, blood vessels, and other anatomical structures, shown in captured image data are located within the patient 1452 than would be the case if only images captured by visual cameras of the augmented reality device were used to estimate a position of such structures.

In some examples, the at least one processor of the augmented reality device can also be configured to analyze received image data from the probe 1454 to identify the internal body structures in the captured image data. For example, various artificial intelligence and machine learning processes can be applied to the captured image data to, for example, distinguish organs from each other or from other structures in the captured image data. For example, image processing can be applied to captured ultrasound data to determine an actual position, size and anatomy of the patient's heart in the chest cavity 1460.

Once an internal body structure is identified, the processor can be configured to generate a virtual object representing the identified internal body structure and position the virtual object at a correct location in the virtual three-dimensional representation of the rescue scene. In particular, information about positioning of the probe 1454 when image data was captured can be used to correctly position and otherwise generate identified body structures in the three-dimensional representation. In some examples, the virtual object of the identified internal body structure could be positioned in the three dimensional representation of the rescue scene and configured to move or change orientation based on detected movement of the patient 1452. Analysis of the captured image data can also be used to determine physical characteristics of the identified internal body structure, such as a size, orientation, outward appearance, and other features of the body structure.

As in previous examples, the at least one processor of the augmented reality device is also configured to generate images of the virtual objects. In previously described examples, the generated images are often either cartoon drawings (e.g., a cartoon drawing of a heart symbol) or stock computer generated images of organs or other anatomical structures. In some examples, an image can be generated based on the image data obtained from the probe 1454. For example, a size, outward appearance, or motion of an image of a heart 1456, as shown in FIG. 14, could be determined by analysis of ultrasound images of the chest cavity of the patient 1452 received from the probe 1454. Also, the image of the heart 1456 can be accurately positioned on the chest of the patient 1452 based on image data from the probe 1454. The at least one processor of the augmented reality device can also be configured to manipulate or reposition the image of the heart 1456 based on image data from the probe 1452 and the field of view 1450 of the augmented reality device in tracking the position and orientation of the probe 1454 itself. Once sufficient information concerning the heart (or other organ or structure within the body) is gathered (e.g., from the probe 1454 and the augmented reality device), then the heart (or other organ/structure) may be more accurately depicted in its position, size, or anatomy than would otherwise be possible. For example, the processor could continually or periodically reposition the image of the heart 1456 as the augmented reality device and wearer move around the rescue scene so that the heart 1456 appears to be correctly positioned on the patient's chest, even when the wearer's field of view 1450 changes.

In some examples, information about the position and/or orientation of internal body structures, such as the image of the heart 1456, can also be used by the processor of the augmented reality device to provide guidance to the rescuer(s) about treatment of the patient 1452. For example, the processor of the augmented reality device can be configured to display targets for connecting electrodes to the patient or hand position targets for performing chest compressions, as described previously in connection with FIGS. 10 and 13A-13C. A position of such targets could be determined or manipulated based on analysis of captured images of internal body structures. For example, a hand position target could be moved so that it is closer to the actual location of the patient's heart to improve efficiency of chest compressions being applied to the patient 1452.

In other examples, analysis of captured image data from the probe 1454 could be used to determine efficiency or quality of treatment being provided to the patient. For example, active chest compressions being applied to the patient 1452 could be tracked in real time based on images captured by the probe 1454 to judge, for example, whether the heart is adequately refilling with blood between chest compressions. Feedback or guidance for performing chest compressions provided by the augmented reality device, within the field of view 1450, could be modified based on the determination of whether refilling is occurring in an expected manner.

In other examples, ultrasound images captured as the heart is beating and/or as chest compressions are being performed could be used to determine how far the heart compresses during each chest compression stroke or to determine a blood flow volume driven from the heart by each compression stroke. Information about efficiency or effectiveness of the compression strokes could also be used to update chest compression parameters. For example, if each compression stroke produces lower than expected blood flow, target values for compression depth or rate could be increased to increase perfusion. Updated parameters could be displayed to the wearer of the augmented reality device within the field of view 1450 of the device.

Manual Ventilations

Figure 15:
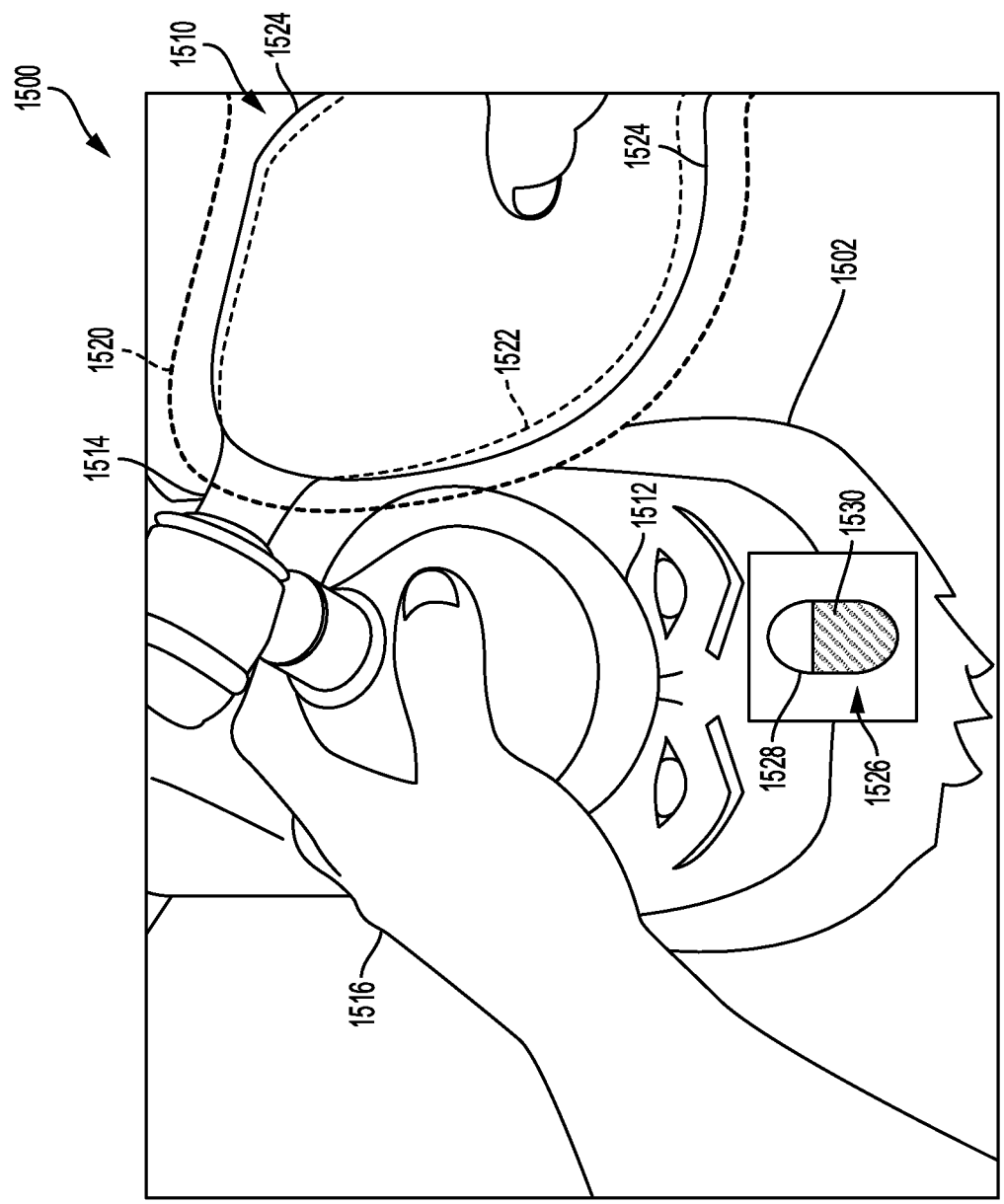
FIG. 15 shows an exemplary field of view through an augmented reality device during performance of ventilations and including a visual indicator of arm/hand position for a manual ventilation using a ventilation bag.

FIG. 15 shows an acute care provider's field of view 1500 through an augmented reality device while providing ventilations to a patient 1502. The acute care provider provides ventilations using a manual ventilation bag 1510. The ventilation bag 1510 is connected to a patient ventilation mask 1512 through an airflow pathway 1514. To provide manual ventilation to the patient 1502, the acute care provider grasps the ventilation bag 1510 with hand(s) 1516, such that his/her thumb(s) are positioned near a top portion of the bag 1510 and his/her fingers are positioned below the bag 1510. The acute care provider compresses the bag 1510 by moving his/her thumb(s) and finger(s) together.

As shown in FIG. 15, the field of view 1500 can include two-dimensional images of virtual objects, which are positioned in the three-dimensional representation of the rescue scene, for providing guidance for compression and release of the bag 1510 at a target ventilation rate and ventilation volume. For example, the images of a virtual objects can comprise an expanded virtual outline 1520 for a fully expanded ventilation bag 1510, a compressed virtual outline 1522, and a virtual movable or guidance outline 1524 configured to move between the outlines 1520, 1522 at a desired ventilation rate. While performing ventilations, the acute care provider can seek to match the shape of the actual bag 1510 to the overlaid moving outline 1524, which moves (e.g., appears to compress and expand) in accordance with a target ventilation rate and volume.

In use, the acute care provider can be instructed to continue compressing the bag 1510 following the virtual guidance outline 1524 until the bag 1510 is compressed to the position indicated by the contracted outline 1522. At that point, the acute care provider should slowly release the bag 1510 so that it begins to expand. Desirably, the acute care provider releases the bag at a speed matching the guidance outline 1524.

In addition to the guidance outline 1524, other information about ventilations and patient breathing can also be provided within the acute care provider's field of view 1500 by the augmented reality device. For example, medical information related to the patient's breathing ability, lung capacity, lung function, and other physiological ventilation characteristics can be relevant for optimizing ventilation treatment parameters. These breathing parameters can be shown in a pop-up information box in the field of view 1500 or appear in a summary screens of the dynamic dashboard display, as described herein.

As previously described, it is believed that ventilation volume is especially important for patients who have experienced traumatic brain injury (TBI), as increased ventilation rate can increase blood flow to the brain. In some examples, the field of view 1500 can further comprise the TBI performance indicator. An exemplary TBI performance indicator 1526 is shown in FIG. 15. The TBI performance indicator 1526 can be a hollow shape 1528 or outline positioned adjacent to the patient's head. In some instances, the shape 1528 may represent the shape of a human brain. The shape 1528 can transition from a filled appearance to an empty appearance to signify blood perfusion to the brain to illustrate blood perfusion to the patient's brain based on measured ventilation rate/volume. If blood flow to the brain is estimated to be too low, the shape 1528 can be empty or only fill a small amount. As blood flow increases toward a normal or acceptable level, the shape 1528 can be filled by a solid or cross-hatched region 1530. The shape 1528 can be completely filled to show that a desired or appropriate level of blood perfusion to the brain is being provided. In other examples, the shape 1528 can be shown in phantom or as a translucent image when blood perfusion is too low. The shape 1528 can become more opaque to indicate that blood perfusion is approaching a desired or acceptable level. If blood flow increases beyond expected or acceptable levels, the shape 1528 may change color to a warning color and/or may begin to flash to signal to the acute care provider that attention to brain blood flow is needed. In other examples, a visual indicator of the brain blood flow can be a gauge icon indicating a percentage of desired or appropriate blood flow (e.g., a gauge reading of 100% indicates that blood flow is substantially in accordance with desired levels and that the acute care provider should continue performing resuscitation activities in the same manner).

In some examples, the images of a virtual object for manual ventilation provided in the acute care provider's field of view 1500 can be based on information from sources other than analysis of images captured by the augmented reality device. For example, information from a flow sensor and/or pressure sensor in the airflow path 1514 extending between the patient's ventilation mask 1512 and the ventilation bag 1510 can be used to provide additional information about ventilations being provided to the patient 1502.

Measurements from the airflow and pressure sensors may be received by the augmented reality device and/or controller. If the augmented reality device and/or controller determines that ventilations being provided are resulting in flow rates and pressures above predetermined values, the controller can cause the augmented reality device to provide a visual indicator to the acute care provider alerting the acute care provider of the potential danger. In particular, ventilations which are provided at a flow rate and/or with high pressure may not be suitable for smaller or younger patients. For example, the projected outlines 1520, 1522, 1524 of the ventilation bag 1510 may be made to flash or change color to inform the acute care provider that compressions are resulting in elevated pressure and flow rate levels. If measured pressure and flow rate are substantially above desired levels, the augmented reality device may display an image of a virtual object in the form of a conspicuous notification or alert. For example, a textual warning stating "Release Now" may flash within the acute care provider's field of view 1500 indicating that the acute care provider has already provided sufficient volume and/or pressure and that the compression of the ventilation bag should be released immediately.

In some examples, as described herein, a dynamic dashboard or heads up display (shown in FIGS. 6A and 6B) can also be provided within the acute care provider's field of view 1500 during performance of ventilations. As in previously described examples, the dashboard can include information about the patient, rescue effort, or rescue scene. Information about traumatic brain injury, estimated values or percentages of blood perfusion, and similar parameters can be displayed in the dashboard. In addition, information collected from other sensors, such as a pulse oxygen sensor, in communication with the augmented reality device and/or controller can also be provided in the dashboard.

Guided Trachea Tube Placement

Figure 16B:
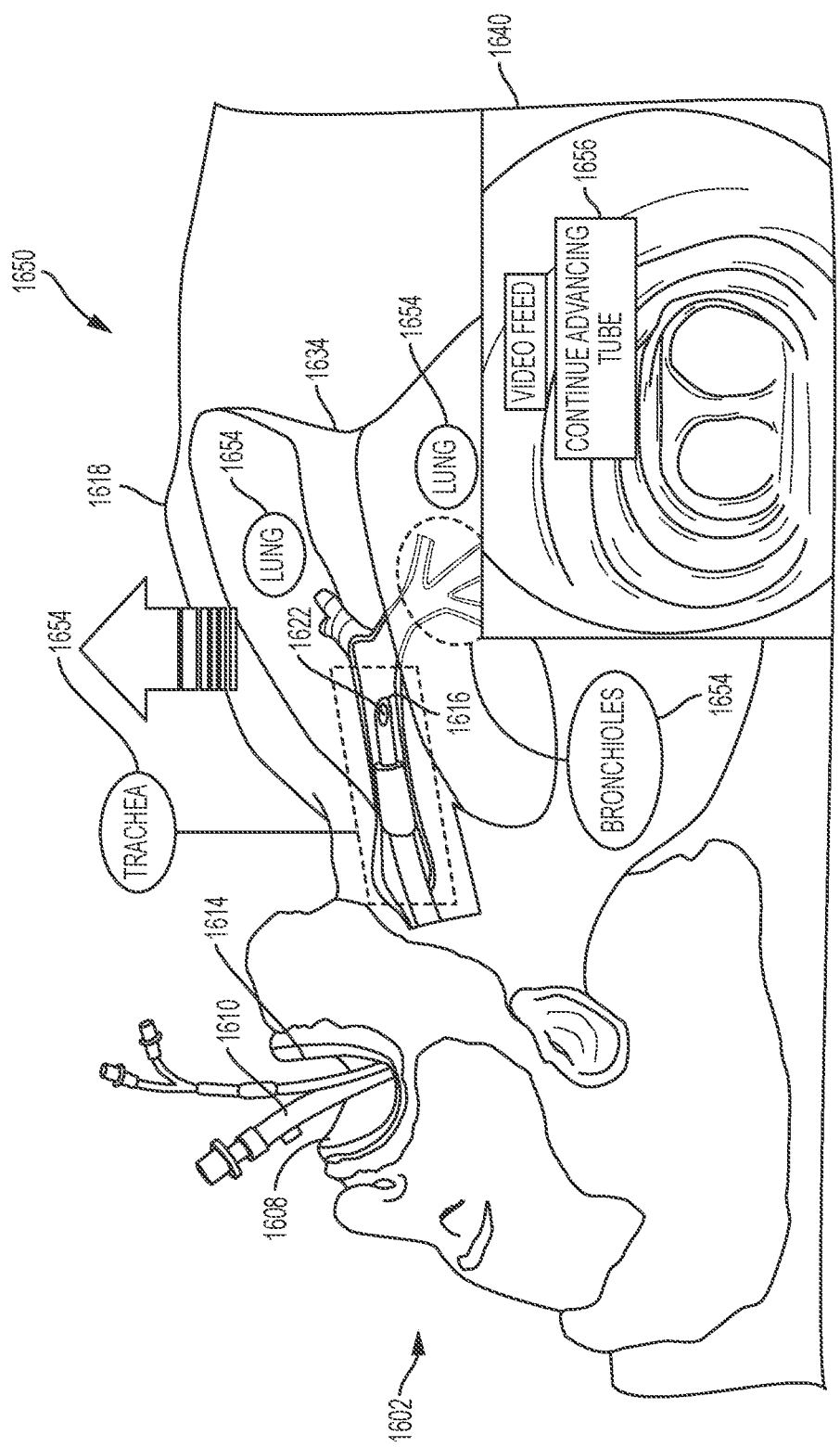
FIG. 16B shows an exemplary field of view through an augmented reality device during insertion and positioning of a tracheal tube and including an in vivo tracheal tube display.

In another example, the augmented reality device is used to guide the acute care provider during placement of a tracheal tube 1610. As shown in FIG. 16A, the tracheal tube 1610 comprises an elongated tubular member 1612 comprising a proximal end 1614 configured to remain external to a patient 1602 (shown in FIG. 16B), a distal end 1616 configured to be inserted through the patient's mouth 1604 (shown in FIG. 16B) to the tracheal or lungs, and a sidewall extending therebetween. The tube 1610 can also include an anchor or positioning portion, such as an inflatable balloon 1620 for maintaining positioning of the tube 1610 in a desired position within a patient's trachea and/or lungs.

As is known in the field, a challenge in placement of a tracheal tube 1610 is ensuring that the distal end of the tube 1610 is advanced to the patient's lungs and not to the esophagus. In order to confirm, verify, or monitor positioning of the tube 1610, the tube 1610 can include a transmitter or beacon 1622 on the distal end 1616 thereof. The beacon 1622 can be, for example, a near field transmitter or communication device which transmits a signal that can be identified by the augmented reality device. The augmented reality device can use the signal to determine where the distal end 1616 of the tube 1610 is within the patient's trachea or lungs. In other examples, information obtained from other medical devices associated with the patient 1602 can also be used for monitoring tube placement. For example, transthoracic impedance measurements can be obtained from a defibrillator connected to the patient 1602. Transthoracic impedance relates to an amount of air in the patient's lungs and, accordingly, is used to verify when the tracheal tube 1610 is correctly placed and providing air to the lungs. In other examples, airway pressure or end tidal $CO_2$ measurements from a mechanical ventilator can be monitored to determine whether the tracheal tube 1610 reaches the lungs. Exemplary ventilation monitoring devices and systems for confirming placement of the tracheal tube in the patient's lungs are described, for example, in United States Patent Appl. Pub. No. 2014/0180138 entitled "Ventilation Monitoring" which is hereby incorporated by reference in its entirety.

With continued reference to FIG. 16A, the tracheal tube 1610 can also include an imaging device, such as a fiber optic tube and digital camera 1630 for obtaining images of the patient's throat, trachea, and other anatomical structures to provide additional confirmation about tube placement. The fiber optic tube and camera 1630 can be, for example, a camera used for conventional laparoscopy procedures and other non-invasive surgery techniques as are known in the art. The tracheal tube 1610 can also include a light source 1632 on the distal end 1616 of the tube 1610 for improving signal quality. The tube 1610 and camera 1630 can be configured to record images and transmit the images to the augmented reality device to be displayed to the acute care provider.

In some examples, the tube 1610 further comprises an identifying code or tag 1652 (shown in FIG. 16A) which can be read by the augmented reality device. For example, the code or tag 1652 can be a QR code or barcode as are known in the art. In other examples, the code or tag 1652 can be a label including an identification number or model name. The augmented reality device can be configured to locate the identifying code or tag 1652 on the tube 1610 and, based on the code or tag 1652, determine information about the tube 1610. The information can include, for example, physical characteristics of the tube (e.g., inner cross sectional area, outer cross sectional area, length, flexibility, manufacturer, model number, or outward appearance of the tube 1610), as well as therapeutic information (e.g., recommended patient age, height, or weight, recommended airflow volume or airway pressure), or other useful information needed for deployment of the tube 1610 to the patient. The tag or code 1652 may also be used to select a virtual image or representation of the tube 1610 from system memory. The augmented reality device can be configured to display the generated image of the tube 1610 within a wearer's field of view 1650 (shown in FIG. 16B) based on stored image data for the tube 1610 identified by the code or tag 1652. Accordingly, information from the code or tag is used to enhance realism and accuracy of the field of view 1650 shown in the wearer of the augmented reality device.

FIG. 16B shows an exemplary field of view 1650 perceived through the augmented reality device for an acute care provider while performing insertion and positioning of a medical instrument configured to be inserted through a patient's mouth, such as a laryngoscope or the tracheal tube 1610. The field of view 1650 is provided to guide the acute care provider as he/she inserts the tube 1610 through the patient's mouth 1608 and, in particular, to provide a visual indication to the acute care provider regarding tube positioning. In order to generate the field of view 1650, the augmented reality device can be configured to first identify the medical instrument to be inserted to the patient. For example, the medical instrument, such as the tracheal tube 1610, can be identified by processing images captured by the augmented reality device. Additional information about the tube 1610 can be determined from the code or tag 1652 (shown in FIG. 16A).

The augmented reality device can also be configured to identify and receive signals emitted from the beacon 1622 or transmitter of the tube 1610 as the tube 1610 is being inserted into the patient's mouth and to determine a relative position of the distal end of the tube 1610 based on the received signal. The augmented reality device can also receive information about transthoracic impedance, end tidal $CO_2$ volume, and airway pressure to provide additional confirmation of tube placement. In response to the received beacon signal and other information, the augmented reality device can be configured to generate and display virtual images or animations 1634 of structures in the patient's cardiothoracic cavity and the tube 1610 showing the position of the distal end 1616 of the tube 1610 relative to the trachea, lungs, esophagus, or epiglottis. For example, the images or animations 1634 can comprise computer-generated representations of the patient's trachea, respiratory organs, and tube 1610. The images or animations 1634 can be projected overlaying the patient's chest 1618 as shown in FIG. 16B. In some examples, a computer-generated representation of the tube 1610 can be based, for example, on information about the tube 1610 identified by the augmented reality device and/or extracted from the code or tag 1652. For example, an accurate image of the tube 1610 can be created based on a computer-generated image of the particular type (e.g., module number and/or size) of tube stored on memory of the augmented reality device. In some examples, the generated virtual images or animations 1634 can also include annotations 1654 identifying the different structures of the cardiothoracic cavity. Based on the context of the field of view 1650 collected from the augmented reality device, the processor(s) may be able to identify anatomical structures of the body. For example, as shown in FIG. 16B, annotations 1654 of the "Lung", "Trachea", and Bronchioles" are displayed within the field of view 1650.

The generated images allow the acute care provider to "see" as the distal end 1616 of the tube 1610 passes through the patient's mouth 1608, moves towards the back of the throat, past the epiglottis, and into the lungs. By following the progress of the tube 1610 on the animations 1634, the acute care provider is alerted if the tracheal tube 1610 enters the esophagus or otherwise is prevented from reaching the lungs. Accordingly, the acute care provider can quickly take corrective action, as needed. For example, the acute care provider can reposition and/or remove the tube 1610 and reinsert it again in hopes of obtaining better tube 1610 placement.

In some examples, notifications and warnings can also be provided to the acute care provider either in the form of visual feedback (shown in the field of view 1650) or by audio and vibration feedback devices of the augmented reality device to alert the acute care provider regarding improper positioning of the tube 1610. For example, a message instructing the acute care provider to continue advancing the tube 1610 can be displayed at appropriate times. When the distal end 1616 of the tracheal tube 1610 approaches the epiglottis, a message could be displayed instructing the acute care provider to advance the tube 1610 more slowly and to ensure that the tube 1610 is advanced into the trachea and not into the esophagus. When the tube 1610 is advanced to a desired depth within the trachea or lungs, a message confirming that the tube is properly placed could be displayed to the acute care provider.

In some examples, the field of view 1650 also includes a real-time video feed 1640 of images captured by the camera 1630. The video feedback 1640 can be real-time or substantially real-time video projected within the field of view 1650, which shows the acute care provider the position of the tube 1610 as it is advanced through the throat and toward the lungs. This arrangement allows the acute care provider to obtain visualization of the esophagus and other anatomical features to ensure that the tube 1610 is placed properly. Directly seeing such anatomical features provides an additional level of protection which prevents the acute care provider from positioning the tracheal tube 1610 in an incorrect manner. Once the tube 1610 is correctly placed, the video feed 1640 may be automatically removed from the acute care provider's field of view 1650, so that the acute care provider has a less obstructed view of the rescue scene and to remove potential distractions. In other examples, the acute care provider can remove or minimize the live video feed 1640 by performing a hand gesture such as, for example, a swiping motion or touching an "x" symbol located adjacent to the feed 1640.

In some examples, the augmented reality device can also be configured to automatically analyze the real-time video feed 1640 of the images captured by the camera 1630 (shown in FIG. 16A) as the tube 1610 is being moved through the patient's mouth and trachea. For example, various machine learning and artificial intelligence processes can be applied to the captured images of the video feed 1640 to identify anatomical structures and landmarks in the captured images and to determine a position of the end 1616 of the tube in the patient's airway. Based on the analysis of the images, the processor of the augmented reality device can be configured to generate instructions or notifications 1656 related to insertion of the tracheal tube 1610 and/or treatment of the patient 1602. For example, instructions could include an instruction to advance the tube or not to advance the tube in a particular direction or to stop advancing the tube when it is correctly positioned in the airway. The at least one processor of the augmented reality device can also be configured to display the notifications 1656 within the field of view 1650. For example, a notification 1656 can be displayed within the field of view 1650 overlaying the video feed 1640.

In one example, as shown in FIG. 16B, the analysis of the captured images from the camera 1630 can determine that the tube 1610 has not been advanced far enough into the patient's trachea. In that case, a notification 1656 instructing the acute care provider to "Continue Advancing Tube" can be displayed within the field of view 1650 near to the live video feed 1640. Once the tube 1610 is advanced to an appropriate position within the trachea, a notification 1656 instructing the acute care provider to "Stop" advancing the tube 1610 can be displayed. In this way, the notifications 1656 provide guidance to the acute care provider for insertion of the tube 1610 and, in some cases, other aspects of treatment of the patient.

Augmented Reality Emergency Response System

The augmented reality devices described herein can be in communication with one another and with other medical and communications devices at a rescue scene forming an augmented reality emergency response system 1700 that guides and coordinates activities of multiple acute care providers during a rescue effort. More specifically, the augmented reality devices 1720 worn by the several rescuers can be linked or associated, so that information collected by one augmented reality device 1720 is made available to other acute care providers and so that acute care providers wearing the respective augmented reality devices 1720 are able to simultaneously view and manipulate a virtual object in the same mixed reality environment. In some examples, movements to the virtual object by one acute care provider may cause the system to adjust or manipulate images of the virtual objects displayed to other acute care providers. In some aspects, three-dimensional information and images sensed or obtained from augmented reality devices can be accumulated and used to generate more robust two- and three-dimensional representation(s) of a rescue scene. Augmented reality devices worn by the acute care providers may also be configured to obtain three-dimensional information and images of the rescue scene and to transmit the images and/or three-dimensional representations to a centralized computing device, referred to herein as a rescue management device.

Figure 17:
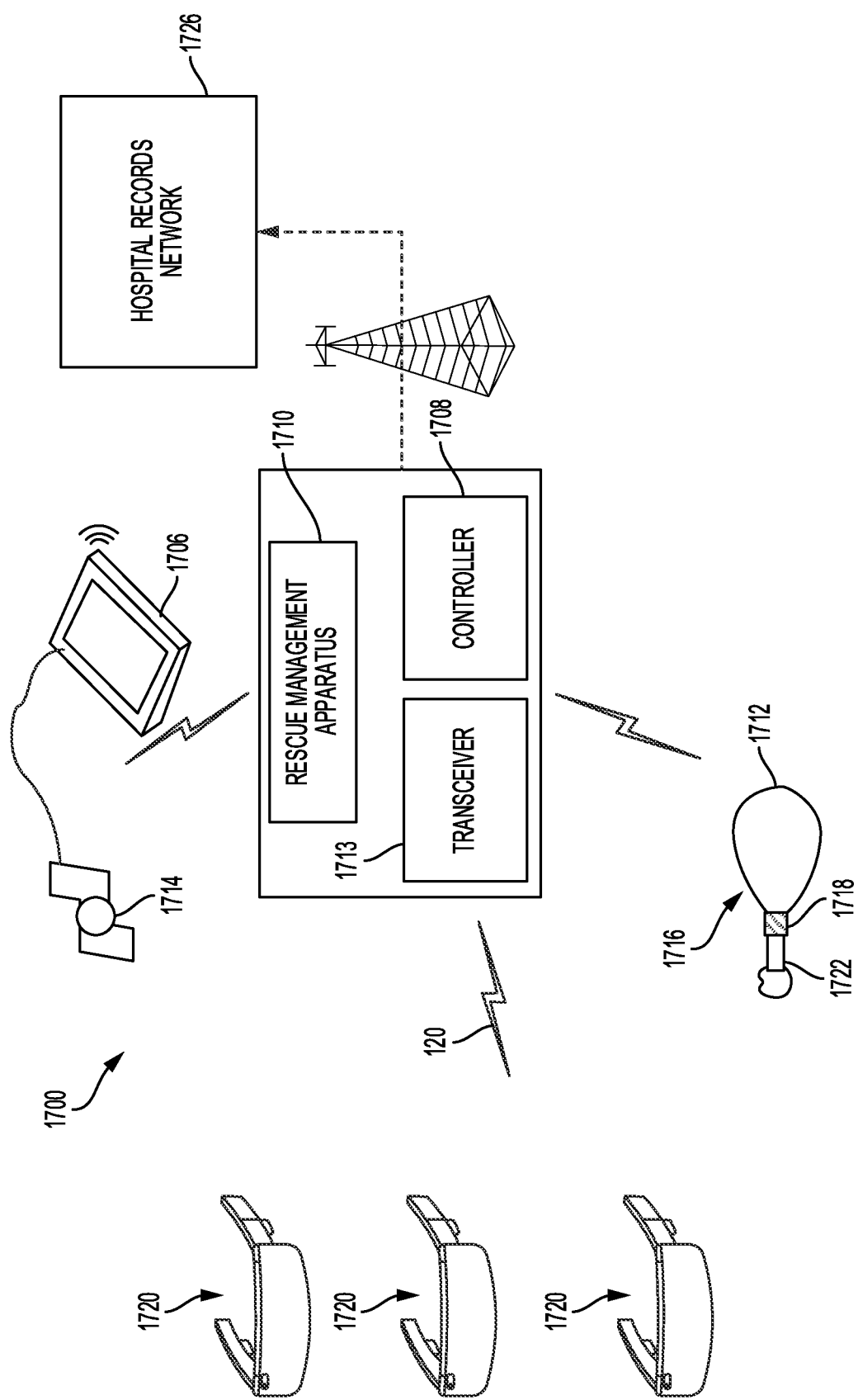
FIG. 17 shows an exemplary augmented reality system including augmented reality devices worn by multiple rescuers.

With reference to FIG. 17, the rescue management system 1700 comprises the augmented reality devices 1720 worn by the acute care providers. The system 1700 further comprises a rescue management device 1710 configured to receive information from augmented reality devices 1720 worn by the different acute care providers at the rescue scene and to make determinations about the rescue effort based on the received information. For example, the rescue management device 1710 may assign particular roles to different acute care providers and monitor status of the acute care providers as the respective roles are being performed. The rescue management device 1710 may also issue alerts instructing acute care providers to switch roles at predetermined intervals. The rescue management device 1710 may also identify other medical devices at the scene and determine and update treatment protocols for the patient based on which medical devices and/or acute care providers are available to provide treatment for the patient.

The rescue management device 1710 can be a dedicated electronic device located at the rescue scene comprising a controller 1708 for executing instructions related to management of the rescue effort and a transceiver 1713 for establishing wireless communication with the augmented reality devices 1720, other medical devices at the scene, and/or remote servers or computer devices at other locations. Alternatively, the rescue management device 1710 can be coupled to other electronic devices at the rescue scene, such as a long-range communications device (e.g., a wireless router or Internet gateway). The rescue management device 1710 can also be associated with multipurpose computerized devices, such as a desktop computer, laptop computer, tabletPC, smartphone, or PDA, running downloadable software (e.g., an app) for interacting and/or communicating with other devices of the system 1700. In some examples, the rescue management device 1710 can be remote from the rescue scene. In that case, the rescue management device 1710 can include circuitry for long-range data communication to interact with the augmented reality devices 1720 and/or other computerized devices and medical devices located at the rescue scene. The app can include instructions that when executed by one or more processors of the controller cause the controller to issue instruction and receive information from the one or more devices of the system 1700.

The rescue management device 1710 may be configured to pass information collected by an augmented reality device 1720 worn by one acute care provider to a device 1720 worn by another acute care provider. For example, images captured by one augmented reality device 1720 can be passed to other augmented reality devices 1720 through the rescue management device 1710. Such visual feedback may be particularly useful as cameras associated with augmented reality devices 1720 worn by others may be in better position to capture images of resuscitation activities being performed than an acute care provider's own device 1720. For example, images captured by an augmented reality device 1720 worn by an acute care provider standing far enough away to "see" both the patient and the acute care provider may more accurately show aspects of chest compression quality, such as arm position, whether elbows are locked, hand position, and release. Images captured by an augmented reality device 1720 while the wearer is performing chest compression could also be unstable or blurry due to rapid movements by the acute care provider.

The rescue management device 1710 can also be configured to control what types of information are displayed to each acute care provider based, for example, on each acute care provider's assigned role. For example, displayed information could be limited to the resuscitation activity being performed by the acute care provider. Displayed information could also be limited based on a level of experience or training of the acute care provider, patient status or condition, or on what devices and individuals are present at the rescue scene. Limiting the amount of information displayed and/or provided to the acute care provider may help to avoid distracting the acute care provider from tasks being performed and may allow the acute care provider to perform his/her role more effectively.

Defibrillator and Treatment Electrodes

The system 1700 can further comprise one or more therapeutic medical devices for treating the patient, such as the defibrillator 1706. As described above in connection with FIG. 1, the defibrillator 1706 comprises sensing electrodes attached to the patient for monitoring cardiac function of the patient. Sensing electrodes can monitor patient ECG, heart rate, and other cardiac parameters. The defibrillator 1706 can further comprise wireless communications circuitry for transmitting the sensed information to the rescue management device 1710 and/or to individual augmented reality devices 1720. In some examples, the defibrillator 1706 can monitor patient ECG to identify a shockable cardiac rhythm that can be treated by the defibrillator 1706. When a shockable rhythm is identified, the defibrillator 1706 can transmit signals to the rescue management device 1710 and/or augmented reality devices 1720 instructing the acute care providers to stop performing resuscitation activities and to step away from the patient. In other examples, information from the defibrillator 1706 can be transmitted to the augmented reality devices 1720 to be projected on the dashboard or heads-up display for each device 1720. In this case, the augmented reality device(s) 1720 can be a remote display or remote alarm for the defibrillator 1706. Beneficially, the user can receive information about operation of the defibrillator 1706 without being required to divert his or her attention from the resuscitation activity being performed.

CPR Assistance Device

In some examples, the system 1700 further comprises a CPR assistance device or puck 1714, such as the accelerometer based device enclosed within the electrode package 110 shown in FIG. 1, for measuring and/or providing guidance regarding rate and depth of chest compressions. The CPR assistance puck 1714 is configured to be placed on and/or held against a patient's chest. The puck 1714 is placed adjacent to the sternum of the patient to identify downward and upward movement of the patient's chest representative of chest compressions. The acute care provider is instructed to grasp and press the puck 1714 against the patient while performing chest compressions. Vertical movement of the puck 1714 can be monitored to assess chest compression depth. Acceleration of the puck 1714 representative of initiation of chest compression can be monitored to assess chest compression rate. In some examples, the puck 1714 is a stand-alone device including electronic circuitry enclosed within a substantially rigid housing. The puck 1714 can be wired or wirelessly connected to the defibrillator 1706 for receiving signals from motion sensors of the puck 1714. In other examples, as shown by electrode package 110 in FIG. 1, the puck 1714 can be integrated with sensing and/or treatment electrodes that are also configured to rest against the patient's chest.

Information from the defibrillator 1706 and puck 1714 can be used to supplement visual images and other sensor information from the augmented reality devices 1720 to improve feedback and guidance provided by the system 1700. The rescue management device 1710 can be configured to compare movement information from the augmented reality device 1720 and CPR puck 1714 to assess aspects of compression quality. For example, movement of the acute care provider's head as measured by processing captured images and/or based on information sensed by accelerometers associated with the augmented reality device 1720 should generally correspond with movement of the hands and arms during compressions. If the sensed movement information is not related in this manner, it may signify that the acute care provider's arm and hand position is improper. In that case, the rescue management device 1710 can cause the acute care provider's augmented reality device 1720 to provide feedback about kinematic aspects of chest compressions to improve the acute care provider's movement. The acute care provider's augmented reality device 1720 may also display data sensed by the CPR puck 1714. For example, the augmented reality device 1720 can provide feedback based on compression rate and depth measurements, as measured by the puck 1714 rather than from analysis of captured images by the augmented reality device 1720. Similarly, rate and depth information from the augmented reality device 1720 and puck 1714 can be compared to assess accuracy of obtained measurement values and/or to calibrate the augmented reality device 1720.

Patient Ventilation Monitoring

With continued reference to FIG. 17, the system 1700 further comprises one or more mechanical and/or electronic devices 1716 for providing ventilation to the patient and/or for monitoring ventilation status of the patient. A ventilation device 1716 can be a manually operated ventilation device, an automatic ventilator, or a mechanical compression device, such as a compression belt or cuirass. The ventilation device 1716 can comprise one or more sensors for measuring ventilation parameters comprising, for example, ventilation rate, ventilation volume, inhaled oxygen concentration, and exhaled $CO_2$ concentration ($ETCO_2$) of the patient. The ventilation device 1716 and/or sensors can be in wireless communication with the augmented reality devices 1720 and/or rescue management device 1710 for informing acute care providers about ventilation status.

As discussed herein in connection with FIG. 1, in some examples, the ventilation device 1716 can comprise a ventilation bag 1712. The ventilation bag 1712 can include a flow sensor 1718 positioned, for example, on a breathing tube 1722 extending from the bag 1712 to the patient. The flow sensor 1718 can be a pneumatic flow sensor comprising a tube having an airway restriction and pressure sensors for measuring changes in airway pressure caused by the airway restriction. The flow sensor 1718 can comprise communications circuitry for wired or wireless communication with other electronic devices, such as an associated augmented reality device 1720 and the rescue management device 1710. Measurements obtained from the flow sensor 1718 can be used to guide administration of mechanical ventilation to the patient by, for example, helping the acute care provider to control ventilation volume and/or rate. In particular, if either ventilation volume or rate exceeds predetermined threshold values, the controller 1708 of the rescue management device 1710 can cause an alert to be provided to the acute care provider. For example, the alert can be wirelessly transmitted from the rescue management device 1710 and/or flow sensor 1718 to the augmented reality device 1720 worn by the acute care provider performing the ventilation activity. The notification or alert can, for example, instruct the acute care provider to modify ventilation volume and/or compression force to adjust output of the ventilation bag 1712 for the purpose of modifying a flow rate.

External Computer Networks

In some examples, the system 1700 can comprise one or more external computer networks and databases remote from the rescue scene. One exemplary external computer network that can be accessed by the augmented reality device(s) 1720 and/or rescue management device 1710 is a hospital records network 1726 including electronic medical records for individual patients. Information about a physiological condition of a patient and/or for medications being taken by the patient can be received from the hospital network 1726 and displayed to acute care providers on the dashboard or heads-up display provided by each acute care provider's augmented reality device 1720. In other examples, medical information about a patient recorded during treatment at the rescue scene can be uploaded to the hospital network 1726 as the patient is being transported to the hospital. The uploaded information can be used by doctors at the hospital during treatment once the patient arrives. Uploaded information, such as medications administered and treatments provided, can also be used for electronic billing purposes and for inventory purposes for the emergency responders.

Resuscitation Activity Management Processes

The augmented reality device(s) 1720 and rescue management device 1710 can also be used for coordinating various aspects of patient care at the rescue scene by, for example, providing instructions and/or feedback to multiple acute care providers to coordinate treatment of one or more patients by a team of acute care providers. In these scenarios, the rescue management device 1710 can be configured to assign a role to each acute care provider to coordinate actions of multiple acute care providers at the rescue scene. The augmented reality device(s) 1720 can capture images of the rescue scene from many different angles and perspectives as the assigned activities are being performed and, based on information determined through analysis of captured images, guide acute care providers in performance of the activities.

Exemplary processes for coordinating such rescue activities will now be discussed in further detail. The processes and routines discussed herein are exemplary processes for directing activities of acute care providers and/or for coordinating treatment for a patient using elements of the systems described herein. The elements of system 1700 are merely exemplary and the processes discussed herein can be carried out by many different types of electronic and/or computerized devices.

Sharing Data Between Augmented Reality Devices

Figure 18:
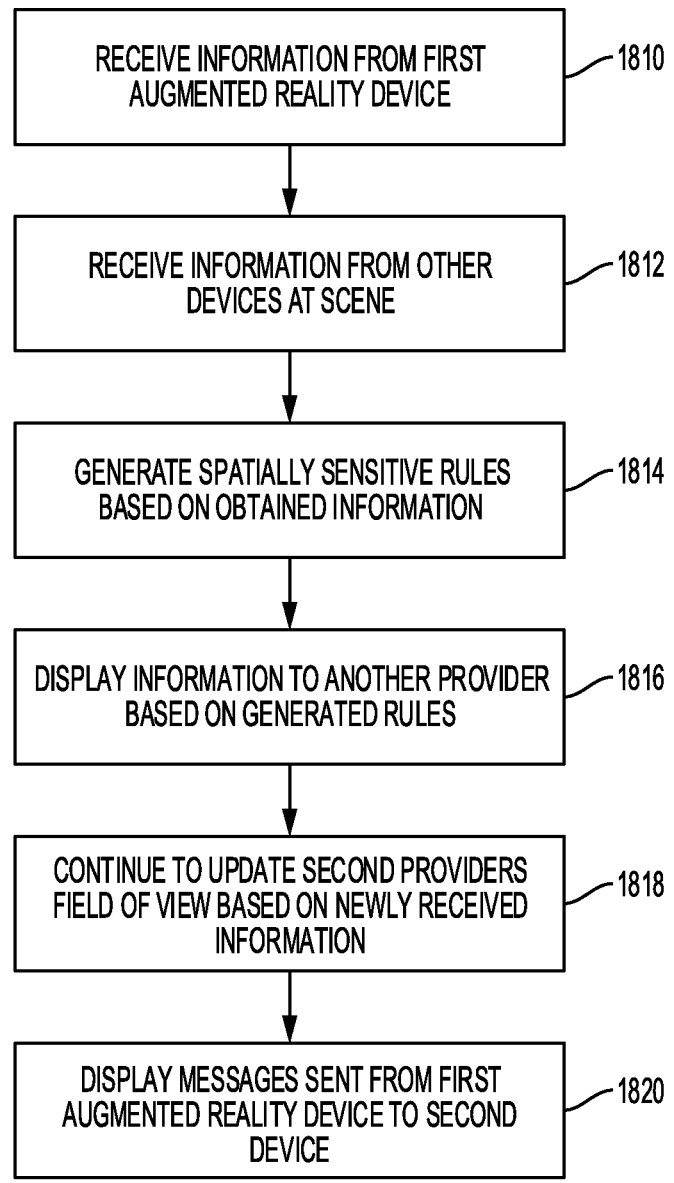
FIG. 18 is a flowchart of a process for sharing information between multiple augmented reality devices according to an aspect of the disclosure.

In one example, the augmented reality system is configured to share data between augmented reality devices worn by different acute care providers and to allow the different acute care providers to perceive and interact with a single mixed reality environment. With reference to FIG. 18, at box 1810, a controller of a rescue management device and/or augmented reality system can be configured to receive and process information, such as three-dimensional information and captured images, from a first augmented reality device worn by a first acute care provider. In some instances, receiving and processing the images can comprise generating the two- and three-dimensional representation(s) of the rescue scene based on the received information. In a similar manner, images may be processed to identify certain physical objects in the captured images or to record objects which pass through the field of view of the respective cameras over time.

At box 1812, in some examples, the controller may also be configured to receive and process information, such as captured images, from other sources at the rescue scene. For example, images may be collected from stationary cameras positioned at the rescue scene. Information may also be collected from other medical devices at the scene. Obtained images from multiple sources can be analyzed to extract information about the rescue effort and/or rescue scene and, in some instances, to identify resuscitation activities performed by one or more acute care providers. Information from the additional sources can be used for generating more robust two- and three-dimensional representation(s) of the rescue scene.

At box 1814, the controller can be configured to apply spatially sensitive rules according to the processed information from the first augmented reality device and/or from other sources. For example, as discussed herein, the spatially sensitive rules can be applied to identify or select types of images of a virtual object and other visual features to be displayed to acute care providers through the augmented reality device(s). In some instances, the same images of a virtual object may be displayed to all acute care providers at a rescue scene. In other examples, spatially sensitive rules may dictate that certain images of virtual objects are only shown to a limited group of acute care providers. Spatially sensitive rules may also cover which images of a virtual object are associated with physical objects identified in captured images. For example, some images of a virtual object are positioned at specific portions of the acute care provider's field of view. Other images of a virtual objects may appear to be projected on or to overlay physical objects and move through the acute care provider's field of view in accordance with the physical objects.

As shown at box 1816, after applying spatially sensitive rules, the controller can be configured to cause a second augmented reality device to generate and display the images of the virtual objects to another acute care provider according to the spatially sensitive rules. Generated images of the virtual objects can be used to provide resuscitation guidance for the second acute care provider such that the images of a virtual object abide in the acute care provider's field of view in accordance with the spatially sensitive rules. In some examples, images of a virtual object may be simultaneously displayed to multiple acute care providers through their respective augmented reality devices. Optionally, an appearance or orientation of an image of a virtual object can be modified based on each acute care provider's position and/or which direction the acute care provider is looking. In this way, different acute care providers can simultaneously view and examine certain three-dimensional holograms from different perspectives.

As shown in box 1818, the system controller can be configured to continue to receive and process images as the acute care provider(s) interacts with the generated images of a virtual object. The system can continue to apply the spatially sensitive rules to the newly acquired information to update or reposition images of a virtual object being displayed to the acute care provider(s) as the rescue effort progresses. For example, performance indicators displayed to the acute care provider(s) may be updated based on quality of resuscitation activities performed by the acute care provider(s). In a similar manner, one of the acute care providers may manipulate an image of a virtual object by, for example, appearing to touch, adjust, or reposition the image. The version of the image of a virtual object shown to the other acute care providers can be updated to reflect actions performed by the other acute care providers.

In one example, captured images may be shown directly to other acute care providers so that they can see aspects of the rescue scene from different perspectives. Accordingly, an acute care provider can, in effect, see the rescue scene from the point of view of another acute care provider. For example, an acute care provider performing chest compressions on the patient may be shown video or static images of how the compressions appear from another perspective (e.g., from the other side of the patient). These videos or static images may help the acute care provider to appreciate whether chest compressions or other resuscitation activities are being performed correctly. For example, being able to see how chest compressions are performed from another perspective may help the acute care provider to appreciate whether he/she is maintaining the correct posture and arm position throughout the chest compression.

At box 1820, during the course of the rescue effort, the acute care provider may select certain information, data, messages, or notifications to send to one or more other acute care providers at the rescue scene. For example, images of a virtual data storage area—"dropbox"—or email mailbox can be displayed within the user's field of view and used to visually depict information to be transmitted or shared with others. In some examples, the acute care provider can virtually drag or drop images of a virtual object and other data shown in his/her field of view into another acute care provider's dropbox or mailbox. The system controller can cause the selected acute care provider's augmented reality device to generate and display the dropped images or data.

Generating and Providing Feedback for a Treatment Protocol

Figure 19:
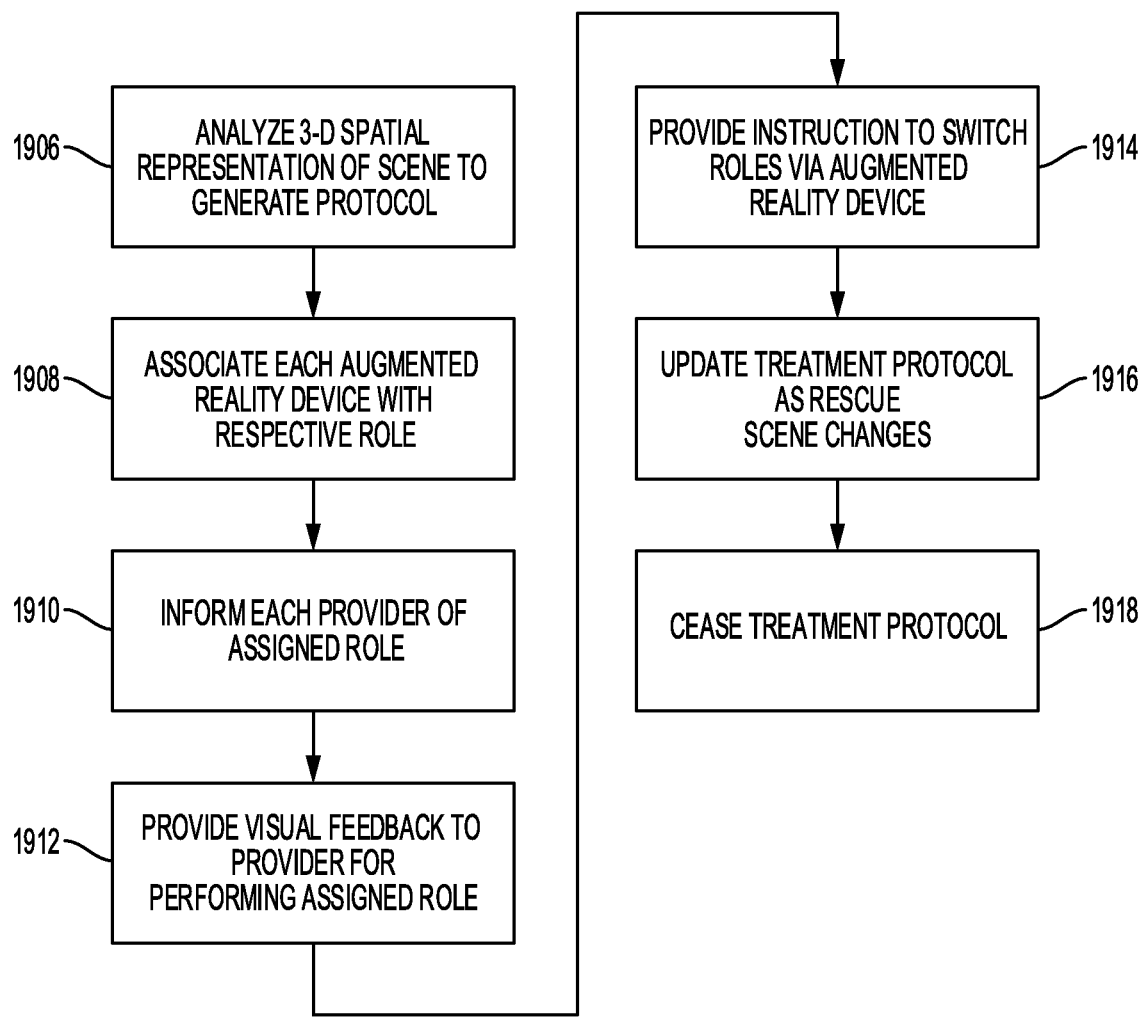
FIG. 19 is a flowchart of a process for coordinating resuscitation activities performed by acute care providers at a rescue scene according to an aspect of the disclosure.

FIG. 19 is a flowchart illustrating an exemplary process for coordinating resuscitation activities performed by acute care providers at the rescue scene. As shown in FIG. 19, upon arrival at the rescue, a controller of a rescue management device is configured to receive images from augmented reality devices worn by one or more acute care providers. The controller can also receive images from one or more stationary cameras located at the rescue scene. The controller is configured to process the received images to generate a two- and/or three-dimensional representation(s) of the rescue scene and to analyze the generated two- and/or three-dimensional representation(s) to identify, for example, a number of prospective patients and acute care providers present at the rescue scene, who may be available to perform resuscitation activities for the identified patients. At box 1906, the analysis of the two- and/or three-dimensional representation(s) of the rescue scene can be used to generate a treatment protocol for identified patients. The treatment protocol can include, for example, a list of resuscitation activities to be performed on one or more of the patients and a determination of when such treatment activities should be performed. For example, generating the treatment protocol can include dividing tasks to be performed between available acute care providers. The treatment protocol can further comprise scheduling when acute care providers should switch roles or, in some cases, when one or more of the acute care providers can rest.

At box 1908, once the treatment protocol is determined, the controller of the rescue management device can be configured to associate each of the identified augmented reality devices with a respective role to be performed. In some examples, the rescue management device automatically assigns particular tasks or roles to particular acute care providers either randomly or according to predetermined criteria. For example, the assignment of a role to an acute care provider can be based on characteristics of the acute care provider, such as physical strength, experience, or skill with particular types of resuscitation activity, as well as on an acute care provider's size, height, or weight. In some instances, information about physical characteristics of the acute care provider can be determined based on analysis of images captured by augmented reality devices (e.g., the generated two- and/or three-dimensional representation(s) of the rescue scene). In other examples, information about each acute care provider can be stored, for example, on computer readable memory on or associated with the respective augmented reality device and/or on memory associated with the rescue management device. In other examples, the rescue management device can consider elements of the rescue scene when associating a particular role to an acute care provider. For example, the assignment of roles can be based on the location of a particular acute care provider (e.g., an acute care provider that is still in the ambulance can be assigned to take out and set up the defibrillator, an acute care provider sitting near the patient's torso can be instructed to begin chest compressions). Similarly, if space or access to the patient is a concern, such as is the case in a vehicle accident, smaller acute care providers can be assigned to provide treatment to the patient while larger acute care providers are assigned other tasks.

In other examples, the acute care provider can select a role and/or a resuscitation activity to perform based, for example, on experience and/or personal preference. For example, the acute care provider can select a role by performing a gesture recognizable by the augmented reality device representative of the selected role. If the acute care provider will perform chest compressions, he or she can place his/her hands next to one another and move them in a downward direction to mimic a compression action. For performance of a ventilation activity, the acute care provider can place his or her palms in an upward position and close the hands towards the thumbs to mimic compressing a ventilation bag. The controller can analyze obtained images of the rescue scene to identify these gestures performed by respective acute care providers. Following identification of the gesture, the controller and/or rescue management device automatically associates the acute care provider with the identified role.

At box 1910, the system can provide a notification to each acute care provider to inform the acute care provider which role he/she has been assigned. For example, the rescue management device may cause each augmented reality device to provide the respective acute care provider with guidance for beginning to perform an assigned resuscitation activity. An acute care provider assigned to perform chest compressions may "see" a visual indicator of where to place his/her hands on the patient's sternum. An acute care provider assigned to setup a defibrillator may "see" a visual indicator to assist in electrode placement.

At box 1912, once the controller confirms that the acute care provider is ready to begin providing the assigned resuscitation activity by, for example, analysis of images obtained by the augmented reality devices, the controller can cause each acute care provider's respective augmented reality device to provide feedback to the respective acute care provider regarding performance of his/her assigned resuscitation activity. For example, feedback can comprise guidance on positioning during performance of the assigned resuscitation activity (e.g., kinematic feedback), information about resuscitation activity parameters (e.g., whether compression or ventilation rate is in accordance with target values), or about an impact of certain resuscitation activities on the patient (e.g., performance indicators).

As shown at box 1914, after a period of time, the acute care providers can be instructed to switch roles. Determinations of when acute care providers should switch roles can be based, for example, on portions of the treatment protocol determined in box 1906. In some examples, the controller can be configured to cause each acute care provider's augmented reality device to provide a notification informing him or her to switch to another role. In some cases, the acute care provider can be instructed which new role to perform. In other examples, the acute care provider can select the new role by, for example, beginning to perform a different type of resuscitation activity. In that case, analysis of captured images and/or analysis of signals received from motion sensors of the acute care provider's augmented reality device can be used to determine which new role the acute care provider has selected. In some examples, the instruction to switch roles is provided after a predetermined period of time (e.g., about two minute). In other examples, the determination of when to instruct acute care providers to switch roles can be based on a determined level of acute care provider fatigue. For example, if analysis of images obtained by the augmented reality device(s) indicates that an acute care provider is not providing resuscitation activities of an expected quality, the acute care provider can be instructed to switch to another role.

As shown at box 1916, in some implementations, the treatment protocol can be modified or updated during treatment of a patient to account for factors that can occur at the rescue scene. One reason for updating a treatment protocol would be if additional acute care providers arrive at the rescue scene increasing the number of acute care providers available to provide treatment. For example, if initially one acute care provider is present, the single acute care provider can be responsible for providing both chest compressions and manual ventilation to the patient. If a second acute care provider arrives, the treatment protocol and respective roles can be updated, so that one acute care provider provides compressions while, in a coordinated manner, the second acute care provider provides ventilation. Similarly, the treatment protocol can be updated as additional medical devices are set up and/or become available. For example, the rescue management device can be configured to identify when a medical device, such as a defibrillator, is set up and ready for use. At that point, the treatment protocol can be updated to include instructing the acute care providers to step away from the patient and providing treatment, in the form of a defibrillating shock to the patient, provided that a shockable rhythm can be identified.

The acute care providers can continue to provide treatment to the patient in accordance with the treatment protocol for as long as necessary or appropriate for the emergency situation. However, after a period of time, at box 1918, the acute care providers are instructed to cease providing treatment to the patient. The instruction to cease treatment could occur, for example, because the acute care providers and patient have arrived at a hospital or medical facility and others have taken over responsibility for treating the patient.

Generating a Report or Code Summary of the Rescue Effort

The augmented reality system can also be used to generate a time-stamped record, summary, or report of the rescue effort based on information collected by the augmented reality devices and/or on analysis of resuscitation activities performed by system components. In some examples, the system can output a code review summary including a time-stamped list of resuscitation activities performed for a patient by different acute care providers at the rescue scene. The code review summary can be based on information collected by each of the augmented reality devices and transmitted to the rescue management device and/or to a remote computer device or a central server. The summary can also include metrics or scores representative of a quality of resuscitation activities performed by the acute care providers.

Previously, acute care providers were responsible for manually recording when particular aspects of the resuscitation activities occurred. For example, an acute care provider may write down in a notebook, sheet of paper, or hand/arm when a particular medication was administered to a patient. In other examples, the acute care provider may identify that a particular resuscitation activity was performed by pressing a button on a medical device, such as the defibrillator or ventilator, to record when the resuscitation activity, such as administration of the medication, was performed. Code markers may be useful for post-rescue review to evaluate the overall course of a resuscitation after the fact, particularly in determining the timing of therapeutic interventions administered to the patient.

Using the augmented reality system disclosed herein, code markers can be recorded automatically. For example, the two- and/or three-dimensional representation(s) of the rescue scene generated from images captured by the augmented reality device can be processed to identify when certain activities are performed by acute care providers. In other examples, a code marker can be identified by analysis of an acute care provider's speech (e.g., the acute care provider can speak a phrase that can be recorded by a microphone associated with the augmented reality device). For example, the user can speak the phrase "Give Epi" while providing an epinephrine injection to the patient. Or, the user may be able to enter the code marker through another action input, such as gestural recognition.

Exemplary code markers, which can be recorded during a rescue effort, include, for example, CPR, Intubate, Airway (clear airway), CPAP (apply continuous positive airway pressure), IV (intravenous medication), IO (intraosseous infusion), Nebulize, Cooling, Sedate, Event, Epi (e.g., administration of epinephrine), Atrop (administration of atropine), Dopa (administration of dopamine), Valium (administration of valium), Phen, Bicarb (administration of sodium bicarbonate), Analges (administration of an analgesic), RSI (rapid sequence intubation), Aspirin, Oxygen, Morphine, B-block (administration of a beta blocker), Lido (administration of lidocaine), Mag Sulf (administration of magnesium sulfate), Thrombo (administration of a thrombolytic), Sedation (administration of a sedative), Heparin (administration of heparin), Procain (administration of procaine), Amio (administration of amiodarone), Amiodar, Gluca (administration of glucagon), Thiamine, Dilantin, Narcan, Atrovent, Adenosine, Fentanyl, Digoxin, Vasopr (administration of vasopressin), Dextrose, Paralytic, Nitro (administration of nitroglycerin), Ca Block, Etomidate, Ativan, Glucose, Albuterol, Amrinon (administration of amrinone), Benadryl, Demerol, Oral Glu (administration of oral glucose), Lasix (administration of furosemide), Calcium, Versed (administration of midazolam), Steroid, Bolus, amongst others. Some code markers may be more appropriate for certain patient conditions. For example, code markers appropriate for cardiac arrest may include CPR, intubate, Epi, Atrop, Dopa, Phen, Bicarb, Lido, Narcan, B-block, Atrovent, Mag Sulf, Procain, Adenosin, Fentanyl, Digoxin, Vasopr, and/or others. In another example, code markers relevant for respiratory distress and/or traumatic brain injury may include Oxygen, Intubate, Morphine, Valium, Sedation, Atrovent, Paralytic, Albuterol, Lasix, Versed, and/or others.

Each of the code markers may have one or more associated treatment protocols which are performed in sequence following identification of an initial code marker. For example, some drugs, such as epinephrine, are administered to patients multiple times at predetermined intervals over the course of a rescue event. When an Epi code marker is input, the controller may automatically schedule another injection at the predetermined interval. The controller can cause the augmented reality device to notify the acute care provider when the next injection should occur.

The augmented reality system can also be used for reviewing aspects of the rescue effort using the code review summary and evaluation metric(s). Reviewing aspects of the rescue effort, which is referred to as code review, can comprise reviewing treatment activities or code markers provided for the patient in chronological order to assess whether appropriate treatment was provided at an appropriate time. Patient information from other sources, such as therapeutic and/or patient monitoring devices, can be considered along with code markers to evaluate whether certain treatment activities had a positive result for the patient.

Figure 20:
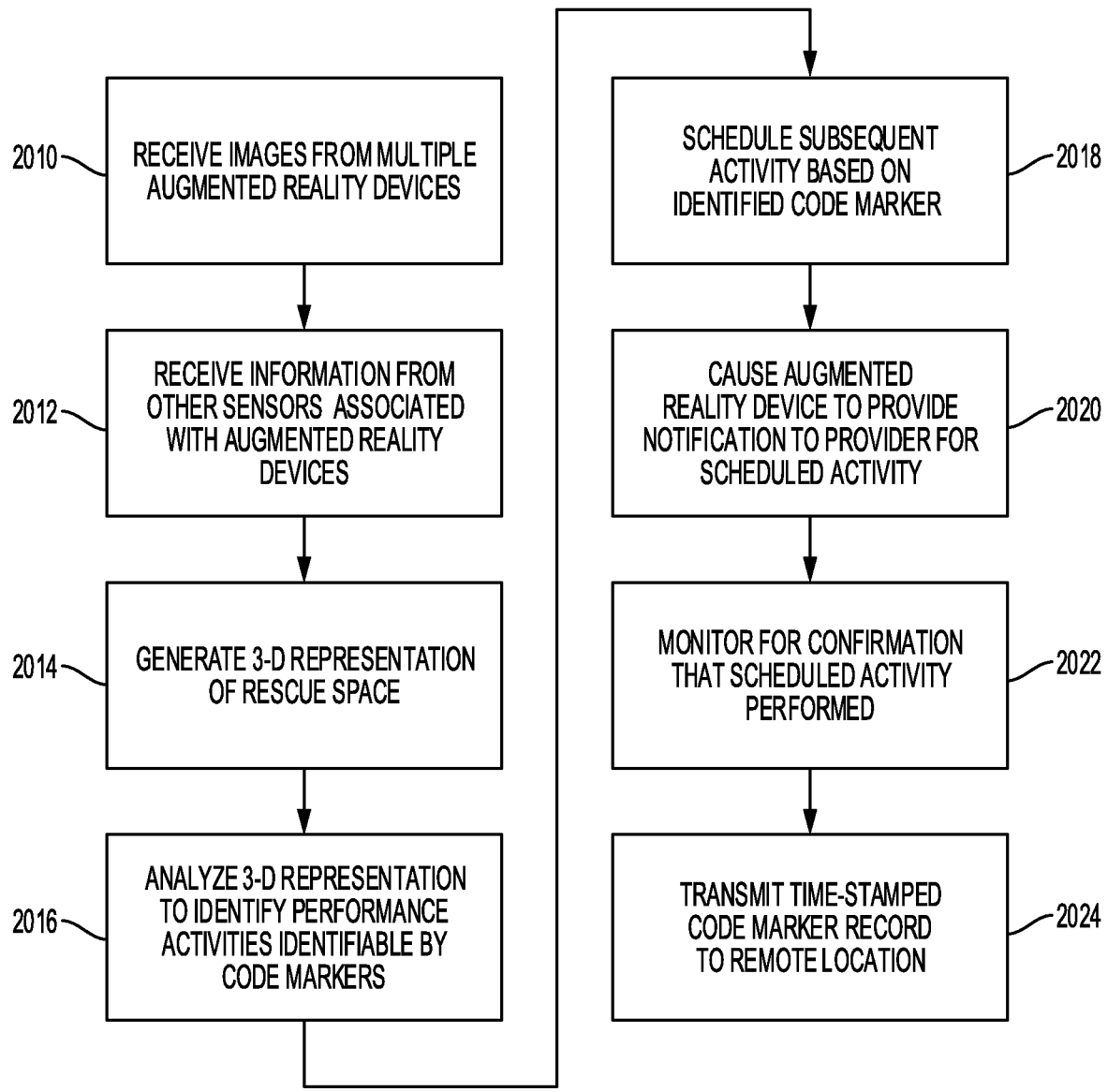
FIG. 20 is a flowchart of a process for generating a time-stamped record of resuscitation activities performed for a patient based on information captured by augmented reality devices according to an aspect of the disclosure.

An exemplary process for creating a report or summary of the rescue effort using the augmented reality system including augmented reality devices worn by multiple acute care providers is shown in FIG. 20. The report could be generated and reviewed immediately following a rescue event, such as immediately after the patient has been transferred to a hospital or medical facility. In other examples, the report or summary could be reviewed several days after the rescue event, such as during a weekly debriefing or training session.

As shown in FIG. 20, the process for generation of the time-stamped record of the rescue event comprises, at box 2010, receiving a series of images from augmented reality devices worn by multiple acute care providers and associating the received images with respective acute care providers or devices. Information from the microphone (for code markers identified by acute care provider speech), as well as other sensors associated with the augmented reality device, such as motion sensors, location sensors, or proximity sensors, may also be received and processed. The augmented reality device and/or system controller can also be configured to record the time that the confirmation or code marker is received. In some instances, the recorded time can be coordinated with a patient physiological signal (e.g., ECG) recorded by a medical device or patient monitoring device for the recorded time, so that a summary report showing effects of the performed resuscitation activity on patient physical condition can be provided.

At box 2014, the received information is used to generate a three-dimensional representation of the rescue scene. At box 2016, the two- and/or three-dimensional representation(s) are analyzed, along with motion and location information, to identify performance of activities which can be identified by a code marker. Upon identification of performance of an activity, a time-stamped record or confirmation of performance of the activity is recorded by the controller. Following identification of a code marker, subsequent activities can be scheduled at box 2018. For example, in the case of administering epinephrine, an acute care provider may be scheduled to re-administer epinephrine at predetermined intervals.

At the scheduled time, at box 2020, the controller can cause a particular acute care provider's augmented reality device to provide a notification to the acute care provider to perform a scheduled resuscitation activity. The notification can include one or more of a visual notification (e.g., text, images, or animations projected within the acute care provider's field of view), an audio notification emitted from the device speakers, and/or a tactile or vibration notification, such as causing the device to vibrate according to a predetermined vibration pattern.

At box 2022, the acute care provider's augmented reality device can be configured to monitor for confirmation that the scheduled activity has been and/or is being performed by analysis of the two- and/or three-dimensional representation(s) and/or other information received from respective augmented reality devices. For example, if the scheduled activity is performing chest compressions to the patient, the confirmation can comprise processing the received images to confirm that chest compressions are being provided to the patient. In other examples, the acute care provider may perform a confirmation action that is not directly derived from performance of the scheduled resuscitation activity. For example, the acute care provider can speak a phrase, such as "Starting Chest Compressions," "Starting Ventilations," "Administering Drug," "Alert acknowledged," or "Task completed" to document that he or she has heard and/or received the notification or alert from the augmented reality device and performed or is performing the required activity. A microphone of the augmented reality device can record the acute care provider's speech and process the recorded signal to confirm that the spoken phrase matches an expected confirmation activity. Alternatively, the acute care provider can perform a predetermined hand gesture or make a selection via interaction with a virtual three-dimensional object projected on to the user's field of view (presented as an image on the visual display of the augmented reality device) to confirm that the alert was understood and that the assigned task was completed. Similarly, the acute care provider may perform a different gesture to instruct the device to repeat the notification or to reschedule the assigned resuscitation activity for a new time (e.g., repeat notification in five minute).

As shown at box 2024, in some examples, the system controller can be configured to transmit a time-stamped record of code markers and/or resuscitation activities identified during treatment of a patient. The time-stamped record can include, for example, data representative of when notifications were provided, when confirmation that the resuscitation activity was performed was received, and when and what code markers were identified. The time-stamped record can be used to generate the summary or report of treatments provided to the patient. The summary report can include a timeline of code markers for particular resuscitation activities shown in a coordinated manner along with sensed physiological signals for the patient, such as patient ECG. The time-stamped record and/or summary report can be sent, for example, to a central patient monitoring facility or data storage facility, where it can be added to a patient's electronic health record. In other examples, the time-stamped record and/or summary report can be forwarded to other medical personnel, such as to a physician responsible for treating the patient once he or she arrives at a hospital or other medical facility. The time-stamped record can be sent to the external source once treatment is completed or, for example, when the patient is transferred from the acute care providers to a hospital or medical facility. In other examples, the time-stamped record can be sent from the device to the external source at predetermined intervals, as treatment is being provided to the patient. For example, a time-stamped record can be uploaded to the external device once every 5 or 10 minutes. In other examples, the device can be configured to upload information when the device is not performing other processor-intensive functions such as, for example, times when the acute care provider is resting or switching roles and when the device is not providing feedback about resuscitation activities being performed.

Figure 22:
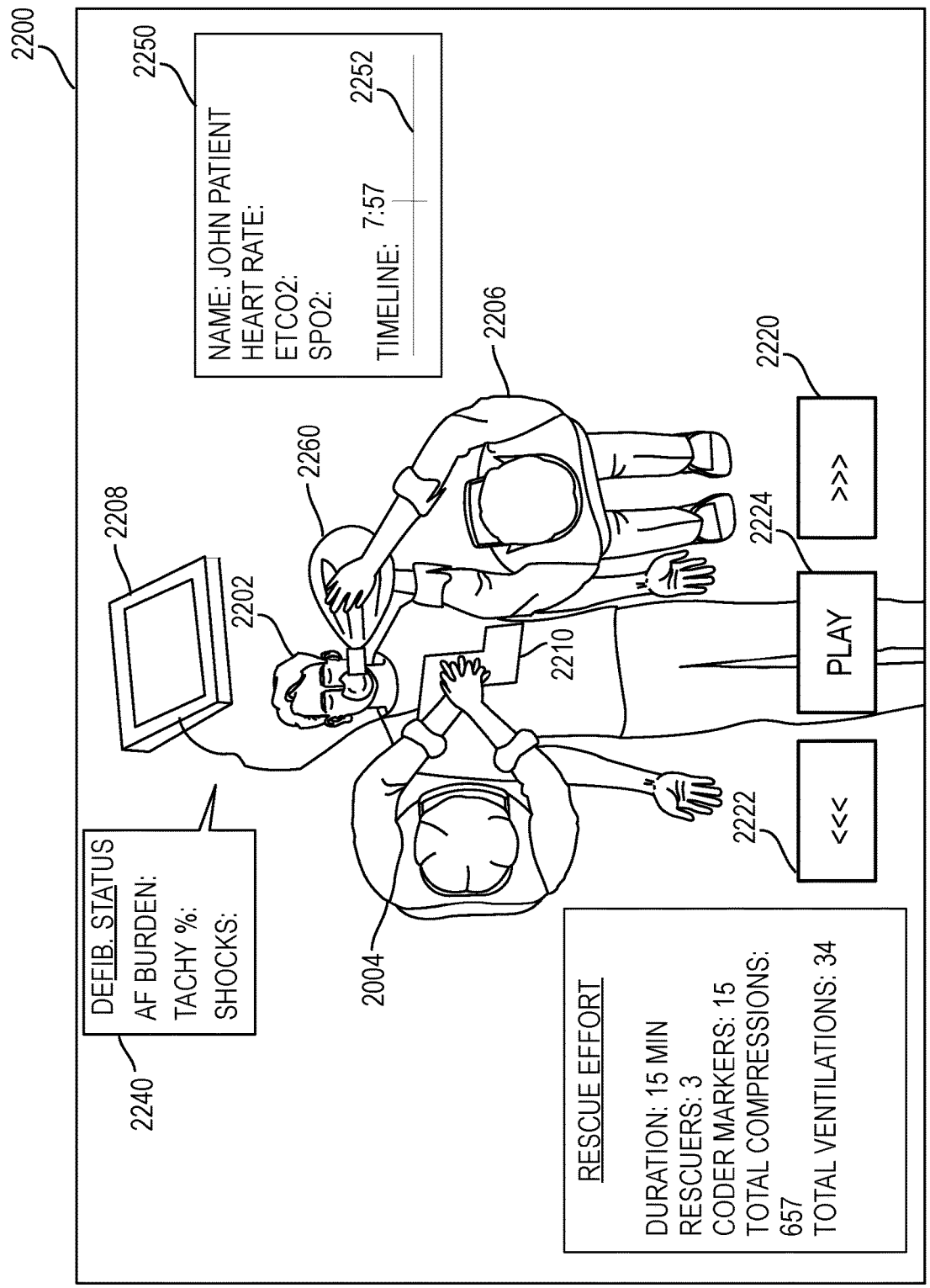
FIG. 22 shows an exemplary field of view for a wearing of an augmented reality device during code review.

In some examples, the received time-stamped record and/or summary report is used for reviewing the rescue effort during a process referred to as code review. Previously, code review could include reviewing a list of code markers collected during the rescue effort. A reviewer may also consider physiological data collected for the patient when certain code activities were performed to consider whether the performed activity resulted in an expected improvement for the patient. The augmented reality system disclosed herein may be used to provide a more immersive code review experience. For example, a reviewer wearing the augmented reality device may step through portions of the rescue effort as recorded in captured images of the rescue scene and the time-stamped record or summary report to assess a quality of care provided for the patient. An exemplary field of view for performing code review using the augmented reality system is illustrated in FIG. 22.

Report of Resuscitation Activity Quality

The augmented reality system can also be used to generate a summary or report including an evaluation metric or score representative of a quality of the various resuscitation activities provided to the patient. Since it may be difficult to determine which acute care provider performed which specific activity, especially if multiple acute care providers perform the same activity at different times during the rescue effort, a summary and/or evaluation metric may be created for each acute care provider showing which activities a respective acute care provider carried out during the rescue effort.

Figure 21:
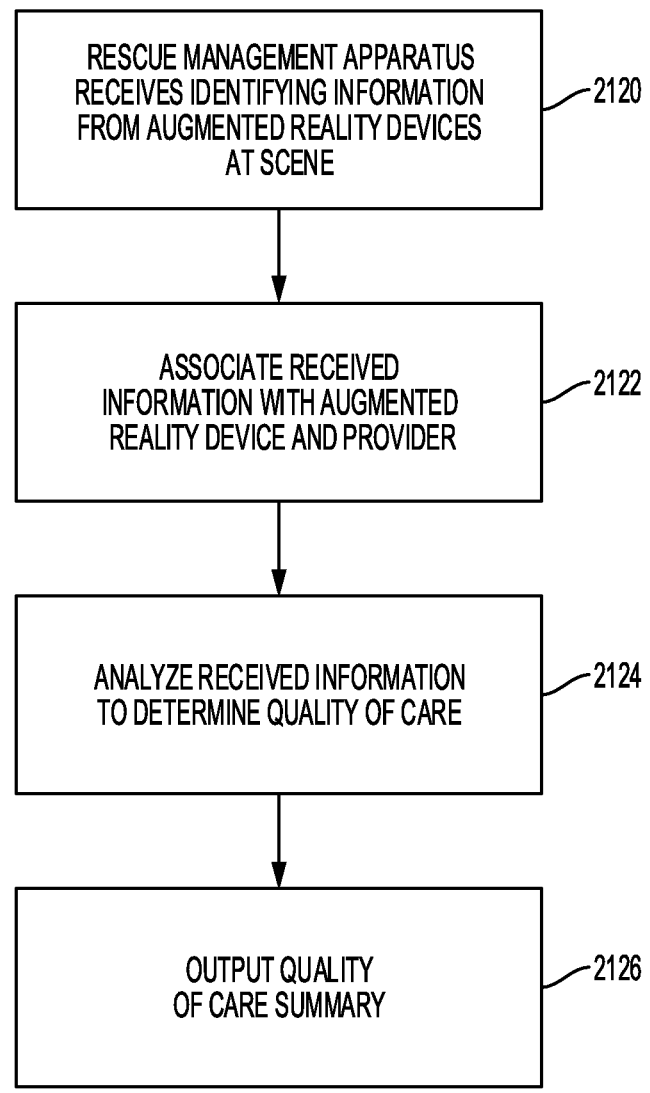
FIG. 21 is a flow chart of a process for generating a quality of care summary based on information collected by augmented reality devices at a rescue scene according to an aspect of the disclosure.

A process for generating a summary report with information about a quality of resuscitation activities performed for a patient is shown in FIG. 21. At box 2120, a rescue management device receives information from one or more augmented reality devices at a rescue scene. As in other examples described herein, the information can comprise captured images showing resuscitation activities performed by the acute care provider(s). The received information can also include information about the rescue effort determined by the augmented reality devices including, for example, information about rescue effort duration, quality of resuscitation activities provided to the patient, patient status information, and information about the rescue scene. Information can be uploaded from the augmented reality device(s) to the rescue management device in real-time as the rescue effort is progressing. In other examples, information about the rescue effort including a list of identified code markers could be uploaded from each augmented reality device as a batch upload at some time following completion of patient treatment.

At box 2122, the rescue management device is configured to process the received information which can include, for example, associating the received information with a respective augmented reality device and acute care provider. In addition to processing the information and associating certain information with a respective acute care provider, the rescue management device may further be configured to provide a time-stamped record for each acute care provider based on analysis of the received information. For example, the rescue management device may be configured to identify and record a time that each resuscitation activity was performed and/or that each code marker was identified. Based on the recorded times, a time-stamped record or timeline for the rescue event including tasks performed by each acute care provider for a patient can be created.

At box 2124, the rescue management device can be configured to analyze the time-stamped records for resuscitation activities performed by the acute care providers to determine information about the quality of care provided by the acute care providers at the rescue scene. For example, the analysis can comprise generating a score or metric for individual acute care providers or for the team of acute care providers. The metric can be a number or letter score based on movement and/or physiological information recorded by the augmented reality devices worn by the respective acute care providers and/or by patient monitoring devices.

The analysis of received information can further comprise automatically annotating received physiological signals (e.g., ECG, blood pressure, breathing rate, pulse oximetry levels) with code markers identified by the acute care providers to produce a correlated report of patient treatment and physiological status. In a similar manner, the analysis can comprise analyzing physiological information for the patient to show how certain resuscitation activities affected the patient. For example, the rescue management device can be configured to coordinate the received time-stamped reports with physiological information for the patient received from other therapeutic and/or monitoring devices.

At box 2126, the rescue management device is configured to output a summary for quality of care based on the analyzed time-stamped record of activity of each acute care provider received from each acute care provider's augmented reality device. The calculated metric or score can be displayed to the acute care providers on their respective augmented reality devices. Alternatively or in addition, metrics or scores for treatment quality can be sent to external sources for storage and further analysis. For example, a report card file including acute care provider's score information and/or physiological outcome information can be uploaded to a data repository, remote computer database, website, or cloud storage environment.

The summary or report of the rescue effort can also be sent from the rescue management device to one or more external computing devices or computer networks. For example, reports listing treatments provided to the patient can be provided to other caregivers responsible for the patient, such as physicians and nurses at a hospital or medical facility that admits the patient for further treatment. In some instances, summaries or reports generated by the rescue management device can also be included in the patient's electronic health record.

Code Review Field of View

According to another aspect of the disclosure, an individual, referred to herein as a "reviewer," may perform code review activities using the augmented reality system. The reviewer can be the acute care provider who performed the resuscitation activities at the rescue scene. In other examples, the reviewer can be a supervisor, physician, or other medical personnel seeking to learn information about the patient and/or rescue effort.

Using the augmented reality system, the acute care provider reviews tasks performed during the rescue effort and patient physiological information by viewing a virtual or mixed reality environment through the augmented reality device. The virtual or mixed reality environment can comprise images, such as images of the patient and/or acute care providers, captured by augmented reality devices at the rescue scene. The virtual or mixed reality environment can further comprise visual indicators, icons, gauges, numerical values, and other virtual objects reporting information about the rescue effort.

In some cases, code review using the augmented reality system may involve going through each code marker entered for the patient to evaluate whether the assigned task was correctly performed and/or whether performing the assigned task improved patient physiological status and/or outcome. For example, the acute care provider may view a patient dashboard display or patient physiological information for a time when a particular code was ordered or carried out. In this way, the reviewer can evaluate why certain activities were performed and whether they should be performed in similar situations in the future.

A field of view 2200 for a reviewer wearing the augmented reality device during code review is shown in FIG. 22. In some examples, all or most of the elements viewable in the field of view 2200 are virtual images based on images captured during the rescue event. In that case, the reviewer can experience a virtual reality representation of the rescue scene. In other examples, the field of view 2200 can include a combination of physical objects and virtual images. For example, acute care providers who participated in the rescue effort may position themselves in the field of view 2200 in a similar position as they were during the rescue effort. This would allow acute care providers to re-experience the rescue effort and to consider how and why certain resuscitation activities were performed.

In the case of a virtual reality representation of the rescue scene, the field of view 2200 comprises virtual representations of a number of medical devices and accessories, which were present at the rescue scene, including, for example, a defibrillator 2208, therapeutic electrodes 2210, and a ventilation bag 2260. Virtual representations of individuals at the rescue scene, such as the patient 2202 and acute care providers 2204, 2206 could also be projected to the field of view 2200. The field of view 2200 can further comprise virtual buttons, such as an advance button 2220, a rewind button 2222, and a pause/play bottom 2224, for advancing through and/or focusing on particular aspects of the rescue effort. The buttons 2220, 2222, 2224 may operate in a similar manner to how a user advances through a television show or movie with a VHS or DVD playing device. For example, pressing the advance button 2220 may cause the environment displayed in the field of view to advance or change to the next code marker in the generated list of time-stamped code markers.

As shown in FIG. 22, various popup displays and/or dashboards, can also be provided within the field of view 2200. A dashboard 2250 can include general information about the patient 2202, acute care provider(s) 2204, and rescue effort for a particular time (e.g., an elapsed time since the start of patient treatment) displayed within the field of view 2200. The dashboard 2250 can further comprise a timeline 2252 showing what time (e.g., elapsed time) during the rescue effort is being displayed. As the user advances forwards or backwards in time through the rescue effort by selecting the appropriate button 2220, 2222 or performing some other predetermined gesture, the information shown in the dashboard 2250 can be updated to reflect the newly selected time. In addition to the general dashboard 2250, as in previously discussed examples, the reviewer can select (e.g., point to) objects or individuals in the field of view 2200 to cause the augmented reality device to display additional information about the selected object. For example, as shown in FIG. 22, a display 2240 is shown with information about the defibrillator 2208. The field of view 2200 can further comprise a dashboard or box 2242 with information about the overall rescue effort. For example, the box 2242 can display overall statistics, such as a rescue event duration, number of acute care providers present at the rescue scene, a number of code markers entered during the rescue event, average compression depth/rate, average ventilation rate/volume, and similar parameters. The box 2252 could further comprise summary information for the rescue event such as the overall score or metric for an individual acute care provider or for all acute care providers at the rescue scene.

In use, the reviewer may initially "see" a rescue scene including only the patient 2202. As the virtual representation of the rescue effort advances, the reviewer "sees" one or more acute care providers 2204 arrive at the rescue scene and beginning to perform resuscitation activities for the patient. The reviewer may also "see" acute care providers set up and begin to operate medical devices (e.g., a defibrillator 2208, ventilator 2260, or patient monitor (not shown)) for the patient. The virtual representation can be interactive, allowing the reviewer to select different individuals to "see" information about the selected individual including, for example, information about the individual's status and/or tasks performed by the individual. Since the virtual environment can be a three-dimensional representation of the rescue scene, the reviewer may also be able to change position or walk around the rescue scene to "see" the rescue effort from different perspectives. The reviewer can also manipulate the virtual representations of the patient 2202, acute care provider(s) 2204, and medical devices in the field of view 2200 to determine additional information about the rescue effort. For example, the reviewer may remove or hide some individuals from the field of view 2200, so that he/she can focus on activities performed by one individual. The reviewer continues to advance through the rescue effort using the buttons 2220, 2220 until all of the code markers entered during the rescue effort have been reviewed. Once all entered code markers have been reviewed, the virtual representation may end. For example, a message may be displayed in the field of view 2200 informing the reviewer that all of the code markers have been reviewed and/or that all relevant information about the rescue effort recorded by the augmented reality system has been displayed.

Training Simulations with Augmented Reality Devices

According to another aspect, the augmented reality device and system can also be used during training simulations to provide guidance and information to a trainee. The augmented reality training simulation can allow the trainee to perceive and manipulate physical objects, such as actual medical devices, disposable medical items, as well as a patient manikin (e.g., a rescue dummies) while also seeing virtual objects or images to guide the training session. The augmented reality device and system can allow trainees to practice resuscitation activities, such as chest compressions and ventilations, in an immersive mixed reality environment which more closely resembles a rescue scene than previously used training techniques. The augmented reality device can also provide sounds or vibration feedback to the trainee during the training simulation to better resemble real world situations. It is believed that exposing trainees to an immersive environment including many aspects of a real world situation or rescue scene can better prepare trainees for actual rescue events. As in previous examples, a controller (e.g., a rescue or training simulation management device) can be configured to receive and coordinate information from augmented reality devices worn by multiple acute care providers performing the simulation, so that the acute care providers can practice working as a team during a rescue effort.

Figure 23:
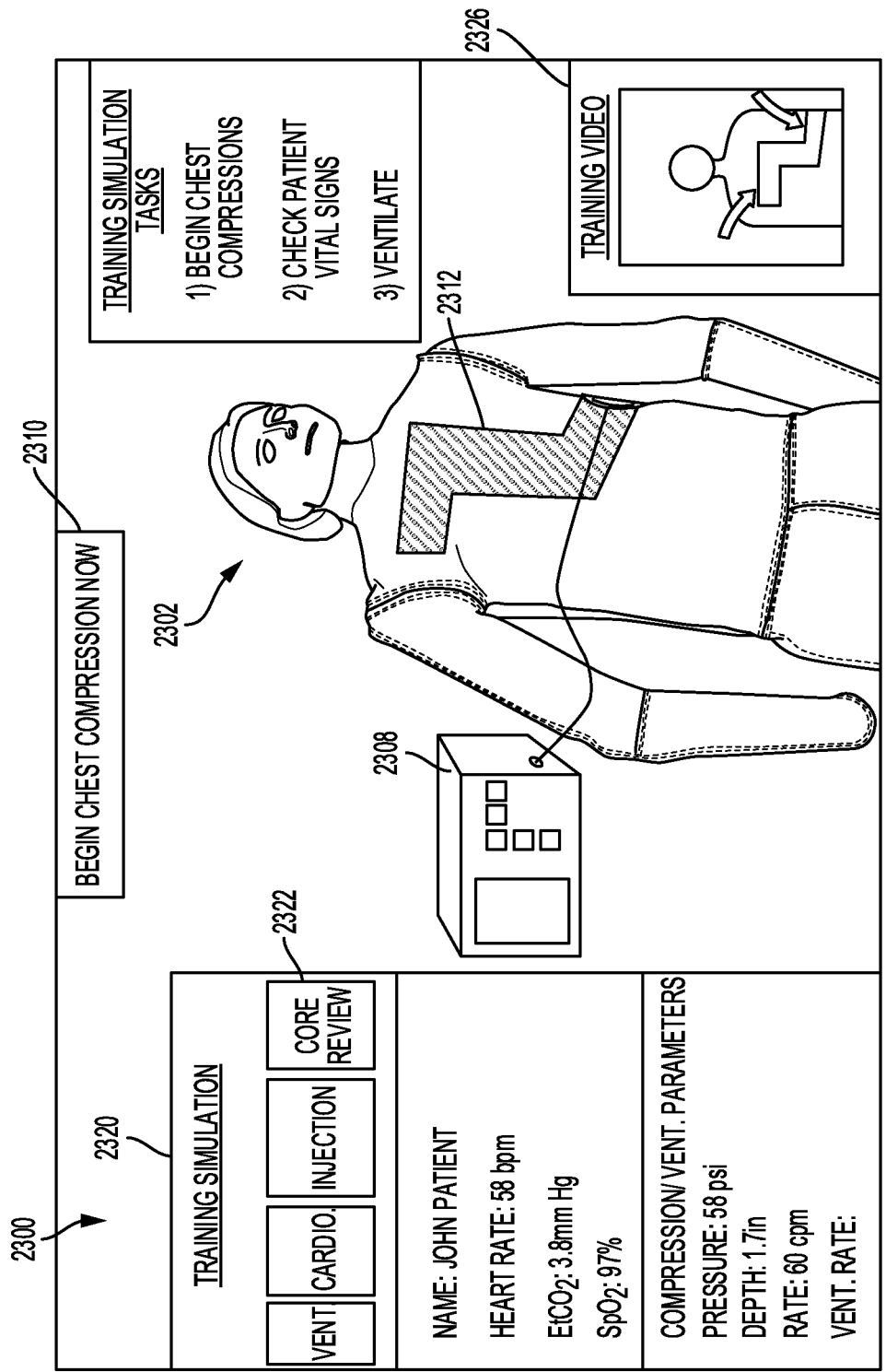
FIG. 23 shows an exemplary field of view of an acute care provider during a training simulation according to an aspect of the disclosure.

FIG. 23 shows a field of view 2300 of an acute care provider through an augmented reality device during a training simulation. As shown in FIG. 23, a manikin 2302 or rescue dummy, which represents a patient to be treated can be provided for use by the acute care provider. The field of view 2300 can also include a defibrillator 2308 and other medical devices commonly found at a rescue scene. These devices can be virtual objects projected in the trainee's field of view 2300 (viewed as images on the screen of the visual display) to increase accuracy of the simulation. In other examples, medical devices, such as the defibrillator 2308 can be physically present and used by the trainee during the simulation. The controller can cause the augmented reality device to provide an instruction to perform a resuscitation activity for the manikin 2302 to the acute care provider. For example, the instruction can be in the form of a textual message 2310. For example, the textual message to "Begin Chest Compressions Now" is displayed within the acute care provider's field of view. Alternatively or in addition, audible messages can also be provided through the device speakers. Along with the message, the augmented reality device may also provide guidance for performance of the resuscitation activity. For example, a visual indicator 2312 can be provided on the sternum of the manikin 2302 showing the acute care provider where his/her hands should be placed. The controller can be configured to monitor movements of the acute care provider, such as by receiving and processing images of the rescue scene obtained from the augmented reality device, to confirm when the acute care provider's hand(s) are in position. In some examples, the controller can cause the augmented reality device to emit notifications or warnings when the acute care provider's hand(s) are not correctly placed. For example, a warning can be a negative sound emitted by the device speakers. Once the acute care provider's hands are in the desired position, the device can emit a positive notification, such as a positive sound, confirming to the acute care provider that his/her hands are correctly placed and that chest compressions on the manikin 2302 should commence. In some examples, the controller and/or augmented reality device may monitor elapsed time from when the notification to begin compressions is provided until chest compressions are commenced. During review of the training simulation, the information may be provided to the acute care provider to ascertain whether the acute care provider needs additional practice correctly positioning his/her hands in an expeditious manner. Once compressions begin, the controller can cause the augmented reality device to provide feedback in a manner similar to feedback described in connection with FIGS. 6A and 6B.

In some examples, the training environment or field of view 2300 further comprises a dashboard 2320 or heads-up display similar to the displays discussed herein in connection with FIGS. 4, 5, 6A, and 6B. For example, the dashboard 2320 can include information about the imaginary patient, rescue effort, and/or acute care provider. The acute care provider can practice interacting with the dashboard 2320 to review and practice responding to the imaginary patient information. For example, the trainee can manipulate virtual buttons 2322 on the dashboard to display more detailed information about particular aspects of the rescue effort. As in previously described examples, the dashboard 2320 can further comprise sections or icons comparing a quality of resuscitation activities being performed to expected or target values. The dashboard 2320 for a training exercise or simulation can further comprise fields or messages which are relevant to training, but which may not be provided when the augmented reality device is used at an actual rescue scene. For example, the dashboard 2320 can include a list 2324 of activities to be performed (e.g., tasks to be performed to complete the training simulation).

In some examples, the dashboard 2320 can also display information obtained from sensors or associated with the manikin 2302 or rescue dummy. For example, the manikin 2302 can include sensors for measuring compression pressure, rate, and depth. The manikin 2302 can also include sensors for measuring airflow rate, volume, and pressure provided to the manikin 2302 by compression of the manual ventilation bag. In some examples, the augmented reality device can also include a real-time video or audio feed 2326 displayed within the field of view 2300 from a trainer or another acute care provider which can be used to coach the trainee through aspects of the training simulation.

In some scenarios, the trainee may practice responding to changes in patient condition based on patient physiological information presented on the dashboard 2320. For example, during the training simulation, the controller may cause the dashboard 2320 to display certain information indicating that the simulated patient is in physical distress. The trainee should recognize and respond to the changes in patient physiological information. For example, the controller may cause the dashboard 2320 to display information (e.g., an ECG trace) which indicates that the imaginary patient has a shockable rhythm. The trainee may respond to the displayed ECG trace by preparing to provide a defibrillation shock to the patient. In a similar manner, if measured ventilation information presented on the dashboard 2320 indicates that the imaginary patient is spontaneously breathing, the acute care provider may modify how ventilations are being provided or may cease providing ventilations entirely.

The augmented reality device can be configured to monitor actions performed by the trainee by image processing of images of the rescue scene obtained by the augmented reality device. The received images can be used to confirm that the trainee responds to changes in patient physiological condition in an expected manner. For example, if the displayed ECG trace shows that a shockable rhythm is presented, the controller may process images to confirm that the trainee has turned his or her head and is looking at and/or manipulating the defibrillator. However, if the trainee does not recognize the ECG trace and continues to perform chest compressions, the controller may cause a notification to be provided to the trainee. For example, a pop up message may be provided in the trainee's field of view 2300 informing the trainee that chest compressions should have ceased and that he/she should be preparing to provide a defibrillation shock to the patient.

Automated External Defibrillator Location and Deployment

According to another aspect of the disclosure, the augmented reality systems and devices disclosed herein can be used for checking a status of, locating, and deploying wall mounted automated external defibrillator (AED) devices. For example, the augmented reality device may display images of a virtual object on the visual display to an acute care provider to direct the acute care provider to a location of a nearest wall-mounted AED. The system can also be configured to identify locations of multiple AEDs and determine which of the AEDs are operating normally and are easily accessible for the acute care provider. Further, the augmented reality device may display images of a virtual object (e.g., arrows, a highlighted path, images of footsteps) on the visual display to direct the acute care provider to the selected AED's location. Once the acute care provider arrives at the AED location, the augmented reality device may display images of a virtual object on the visual display comprising instructions for deploying and using the AED.

An individual nay need to locate an AED in a variety of different situations. For example, the individual wearing an augmented reality device could be an acute care provider or other emergency personnel in situations in which portable defibrillators (such as devices stored in ambulances) are not available. In other examples, the individual wearing the augmented reality device could be a technician or repair person responsible for keeping defibrillators in businesses, government buildings, and other locations in working order. Such technicians and repair persons are responsible for locating and testing multiple AEDs during performance of their repair duties. As such, an augmented reality device for assisting the wearer in identifying an AED of interest would be useful.

Figure 24:
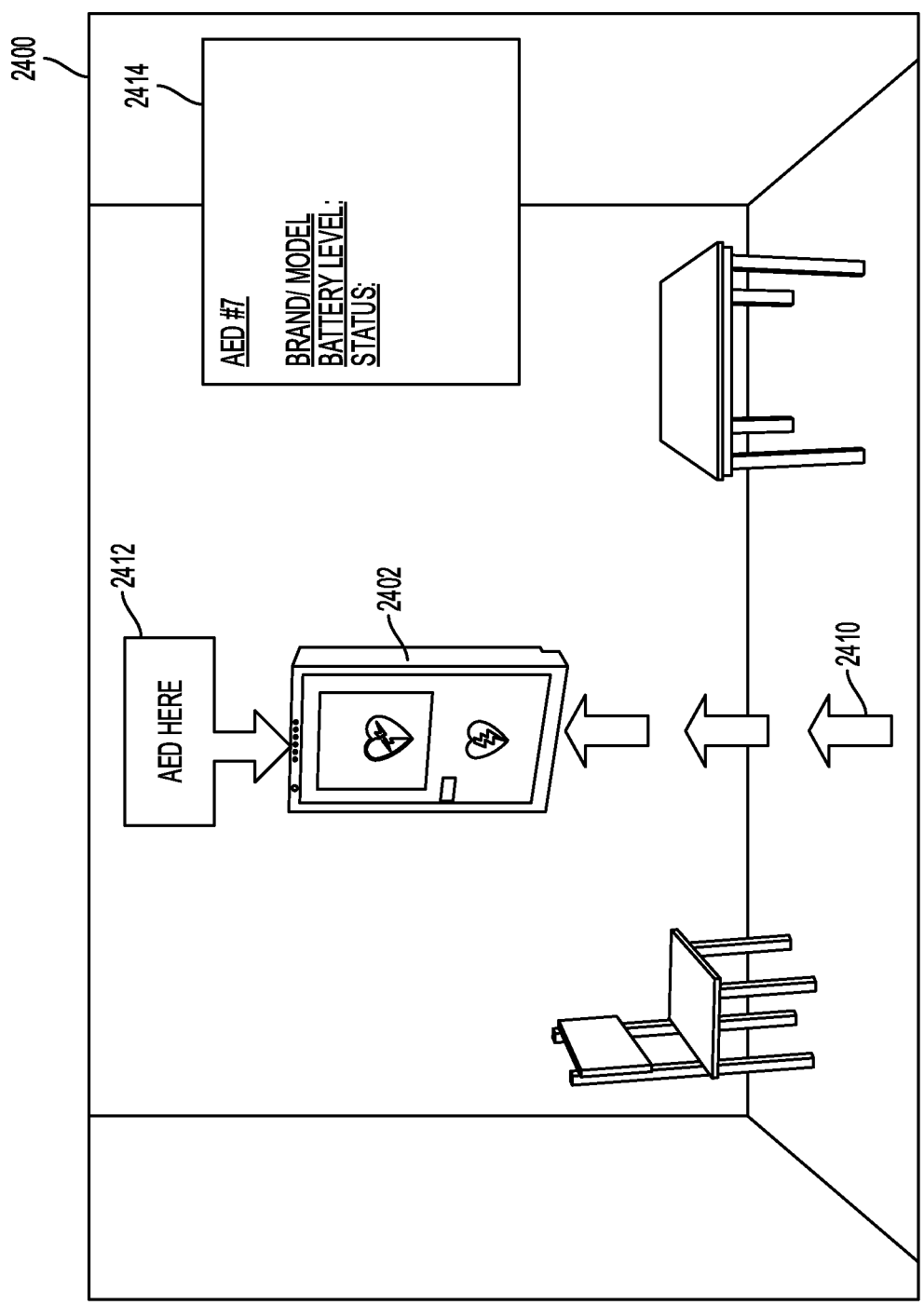
FIG. 24 shows an exemplary field of view of an acute care provider wearing an augmented reality device during defibrillator location and deployment according to an aspect of the disclosure.

FIG. 24 shows an exemplary field of view 2400 for an individual wearing an augmented reality device while locating an AED 2402. The field of view 2400 includes indicators, such as arrows 2410, for guiding the user to the AED. The augmented reality device could also provide audible instructions for guiding the user toward an AED 2402, in a manner similar to audible instructions provided by a GPS navigation device. Once the AED 2402 is in view, an indicator showing the individual where the AED is located can also be displayed. In some examples, the indicator could be a simple message 2412, such as "AED Here," instructing the individual where the AED 2402 is located. In other examples, as shown in FIG. 24, the indicator can also include a popup box 2414 with information about the AED 2402, such as a device name or identifier, battery level, and/or device status. By looking at the information, a technician could determine whether the AED 2402 really needs to be repaired or replaced. If the indicator shows that the AED 2402 is operating normally, the technician could move on to another device.

In some examples, the field of view 2400 further comprises instructions for deploying the AED 2402. For example, the field of view 2400 could include messages and icons showing the user how to remove the AED 2402 from a cabinet or housing, connect electrodes to the patient, turn on the AED 2402, and/or prepare the AED 2402 to provide a defibrillation shock. For example, as described previously, instructions for electrode placement could include displaying images overlaying the patient's chest showing where electrodes should be placed. Instructions for turning on and using the AED 2402 could include visual indicators informing the user which buttons to press at which times.

Figure 25:
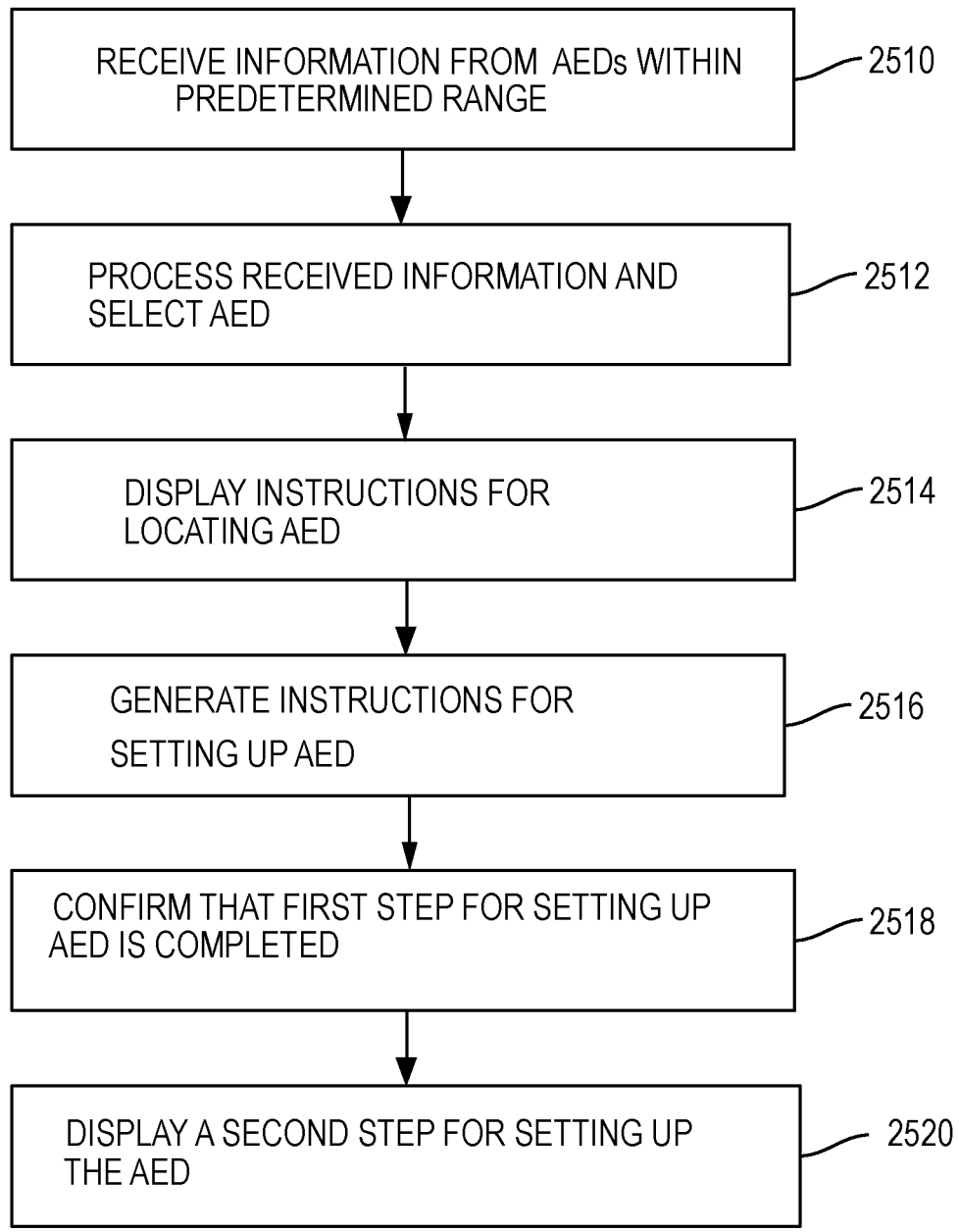
FIG. 25 is a flowchart of an exemplary process for locating and setting up a defibrillator device with an augmented reality device according to an aspect of the disclosure.

FIG. 25 is a flowchart of an exemplary process performed by a controller of the augmented reality device for displaying information about location and deployment of the AED. The process can be started automatically, such as when a monitoring device associated with a patient determines that an AED is needed to treat a patient. In a similar manner, the process could be started as soon as a technician arrives at a building or another location having multiple AEDs located therein. In other examples, the user may instruct the augmented reality device to begin searching for AEDs located nearby and to provide feedback about AED location.

As shown in FIG. 25, at box 2510, the augmented reality device receives identifying signals from AEDs located nearby. The identifying signals can be wireless transmissions from transmitters attached to the AEDs. The wireless transmission can include location information for the AED, identifying information about the AED (e.g., brand name, device type, device features), as well as device status information, such as whether the battery is fully charged and/or whether the device has passed recent self-tests. At box 2512, the augmented reality device processes the received signals to select preferred AED. For example, a decision about which AED to select could be based on distance (e.g., which AED is closest to the user), features of a particular AED (e.g., which AED is easiest to setup or use, which AED is capable of pacing), or device status (which AEDs have passed recent self-tests). Based on the received information, the augmented reality device can automatically select an AED for the wearer to use. In other examples, a list of available AEDs could be projected within the user's field of view. The user could then select a desired AED by, for example, pointing at the desired entry of the displayed list.

In box 2514, after the AED is selected, the augmented reality device displays the instructions for locating the AED to the user. For example, as shown in FIG. 24, the instructions can include arrows, messages, and audible instructions directing the user to the AED. Further, if the acute care provider goes the wrong direction, the augmented reality device can display a warning and/or recalculate a path to direct the wearer to the AED. At box 2516, once the user approaches the AED, the augmented reality device can begin to provide step by step instructions for setting up and using the AED projected in user's field of view. For example, a first message may be displayed instructing the user to remove the AED from the cabinet. Subsequent messages could explain, for example, how to properly place electrodes on the patient and how to turn on the AED to begin providing a defibrillation shock. In box 2518, the augmented reality device processes captured images of the wearer's field of view to confirm that a task has been correctly completed. For example, the augmented reality device may continue displaying a message to remove the AED from the cabinet until an image of an empty cabinet is recorded by the augmented reality device. Once the augmented reality device confirms that a task as been completed, in box 2520, a message related to a next task or step in deploying and using the AED is displayed to the user. The process of displaying messages and confirming that a task or step has been completed is continued until, in box 2522, a defibrillation shock by the AED is provided to the patient. The AED may continue to automatically provide treatment in an appropriate manner until other acute care providers arrive or until the patient is ready to be transported to a medical facility, such as a hospital. In some examples, information about when an ambulance or additional acute care providers will arrive and/or instructions for transporting the patient can also be displayed on the augmented reality device in a manner similar to the above-described message and virtual indicators.

Hospital Use

According to other aspects of the disclosure, systems including the above-described augmented reality device(s) can be adopted for use in a hospital environment. For example, augmented reality devices can be worn by physicians or caregivers to receive status and other information about a patient, medical devices, or about the physician's schedule. In one example, a physician may use an augmented reality device while performing rounds through a hospital ward. The physician may, for example, view a patient's medical record with the augmented reality device before examining the patient. For example, an electronic version of the patient's medical record may be projected within the physician's field of view. The physician may manipulate the projected medical record by, for example, performing certain gestures (e.g., flipping through pages, annotating portions of the medical record, or tapping on portions of the medical record to review more information about selected topics). Beneficially, patient privacy may be preserved by using projected electronic patient records since only the treating physician is able to view the patient record. In that case, the number of hard or paper copies of a patient's medical record needed at the hospital could be substantially reduced.

In use, the physician may begin rounds by "seeing" a list of patients that he/she is scheduled to visit. The physician can enter a room of a first patient and begin the examination by reviewing the virtual copy of the patient's medical record as discussed above. The physician could then examine the patient through the augmented reality device. During examination of the patient, the physician could turn off any virtual objects present in his/her field of view so that he/she has an unobstructed view of the patient. In other examples, dashboards and popup boxes could be positioned near the periphery of the physician's field of view to provide information about the patient and examination. The physician can input notes about the patient examination using the augmented reality device by typing using the virtual keyboard or virtual notepad, as described previously. In other examples, audible notes may be recorded by the microphone associated with the augmented reality device. Once the examination of the patient is completed, the physician can view his list of patients to be examined and decide which patient should be examined next. Once a patient is selected, the physician can select the next patient's name from the list and move to the next patient's room. The augmented reality device could provide instructions for how to get to the next patient using images, such as virtual arrows or footsteps, directing the physician where to go.

Although augmented reality devices and rescue management devices have been described in detail for the purpose of illustration based on what is currently considered to be the most practical examples, it is to be understood that such detail is solely for that purpose and that the disclosure is not limited to the disclosed examples, but, on the contrary, is intended to cover modifications and equivalent arrangements. For example, it is to be understood that this disclosure contemplates that, to the extent possible, one or more features of any example can be combined with one or more features of any other example.

What is claimed is:

1. A spatially sensitive augmented reality system for providing resuscitative feedback in a mixed reality environment to an acute care provider during occurrence of a cardiac event in a patient, the system comprising:
a wearable augmented reality device having at least one three-dimensional sensor, a visual display for viewing by the acute care provider, and at least one processor configured to:
receive and process three-dimensional information of a scene of the cardiac event;
produce a three-dimensional representation of a field of view of the acute care provider based on the processed three-dimensional information;
identify one or more physical objects associated with the cardiac event in the three-dimensional representation;
generate at least one virtual three-dimensional object within the three-dimensional representation;
generate an image of the virtual three-dimensional object within the three-dimensional representation on the visual display according to one or more spatially sensitive rules that provide emergency resuscitative guidance to the acute care provider for treating the patient; and
manipulate the image of the virtual three-dimensional object within the three-dimensional representation on the visual display as an interaction with the one or more identified physical objects according to the one or more spatially sensitive rules that provide further emergency resuscitative guidance to the acute care provider for treating the patient.

2. The spatially sensitive augmented reality system of claim 1, wherein the one or more spatially sensitive rules for generation of the image of the virtual three-dimensional object on the visual display include a position and orientation relationship between the wearable augmented reality device and a three-dimensional reference frame of the three-dimensional representation of the field of view of the acute care provider.

3. The spatially sensitive augmented reality system of claim 2, wherein the one or more spatially sensitive rules for manipulation of the image of the virtual three-dimensional object on the visual display include at least one of:
a position or orientation relationship between the wearable augmented reality device and the three-dimensional reference frame, and
a positional or orientation relationship between the virtual three-dimensional object and the identified one or more physical objects within the three-dimensional representation.

4. The spatially sensitive augmented reality system of claim 1, further comprising an image sensor, wherein the at least one processor is configured to:
receive and process image information obtained by the image sensor, and
recognize an image object within the processed image information.

5. The spatially sensitive augmented reality system of claim 4, wherein the at least one processor is configured to correlate the recognized image object with the identified one or more physical objects associated with the cardiac event within the three-dimensional representation.

6. The spatially sensitive augmented reality system of claim 5, wherein the at least one processor is configured to refine the identified one or more physical objects associated with the cardiac event.

7. The spatially sensitive augmented reality system of claim 6, wherein the at least one processor is configured to refine the accuracy or specificity of the identified one or more physical objects associated with the cardiac event.

8. The spatially sensitive augmented reality system of claim 1, wherein the at least one processor is configured to determine an occurrence of one or more acute care activities of the acute care provider based on the one or more identified physical objects of the three-dimensional representation.

9. The spatially sensitive augmented reality system of claim 8, wherein the at least one processor is configured to calibrate the processed three-dimensional information according to the one or more acute care activities based on a user-initiated action by the acute care provider.

10. The spatially sensitive augmented reality system of claim 9, wherein the user-initiated action comprises connection of an electrode assembly to at least one processor and recognition of the type of electrode assembly to be adult or pediatric.

11. The spatially sensitive augmented reality system of claim 9, wherein the user-initiated action comprises a manual input from the acute care provider of at least one of patient dimensions, patient size, and patient age.

12. The spatially sensitive augmented reality system of claim 9, wherein the user-initiated action comprises performance of a calibration protocol by the acute care provider for augmented reality device to determine patient dimensions.

13. The spatially sensitive augmented reality system of claim 1, wherein the at least one processor is configured to recognize one of the identified physical objects in the three-dimensional representation as at least one of the patient and another acute care provider associated with an assigned resuscitative role.

14. The spatially sensitive augmented reality system of claim 13, wherein the at least one virtual three-dimensional object comprises an indication instructing acute care providers to switch CPR roles.

15. The spatially sensitive augmented reality system of claim 1, wherein the at least one processor is configured to recognize one of the identified physical objects in the three-dimensional representation as at least one of a defibrillator, an electrode assembly, a chest compression sensor, and a ventilation bag.

16. The spatially sensitive augmented reality system of claim 1, wherein the at least one processor is configured to recognize one of the identified physical objects in the three-dimensional representation as at least one anatomical feature of a patient.

17. The spatially sensitive augmented reality system of claim 16, wherein the at least one anatomical feature of the patient comprises at least one of a sternum, a sternal notch, an axilla, ribs, an anterior portion of the patient, a posterior portion of the patient, a desired electrode placement position, and a desired chest compression sensor placement position.

18. The spatially sensitive augmented reality system of claim 17, wherein the at least one anatomical feature of the patient comprises the desired chest compression sensor placement position, and wherein the virtual three-dimensional object comprises a virtual chest compression sensor located at the desired chest compression sensor placement position.

19. The spatially sensitive augmented reality system of claim 18, wherein one of the identified physical objects in the three-dimensional representation comprises a chest compression sensor, and the at least one processor is configured to provide feedback of whether the chest compression sensor is placed on the patient's body according to the desired chest compression sensor placement position.

20. The spatially sensitive augmented reality system of claim 19, wherein the feedback of whether the chest compression sensor is placed on the patient's body according to the desired chest compression sensor placement position comprises at least one of visual feedback, audio feedback, and haptic feedback.

21. The spatially sensitive augmented reality system of claim 19, wherein another one of the identified physical objects in the three-dimensional representation includes an electrode assembly, and the at least one processor is configured to provide feedback of whether the electrode assembly and the chest compression sensor are placed on the patient's body according to the respective desired electrode placement position and the desired chest compression sensor placement positions.

22. The spatially sensitive augmented reality system of claim 16, wherein the at least one anatomical feature of the patient comprises a desired electrode placement position, and wherein the virtual three-dimensional object comprises a virtual electrode assembly located at the desired electrode placement position.

23. The spatially sensitive augmented reality system of claim 22, wherein one of the identified physical objects in the three-dimensional representation includes an electrode assembly, and wherein the at least one processor is configured to provide feedback of whether the electrode assembly is placed on the patient's body according to the desired electrode placement position.

24. The spatially sensitive augmented reality system of claim 23, wherein the feedback of whether the electrode assembly is placed on the patient's body according to the desired electrode placement position comprises at least one of visual feedback, audio feedback, and haptic feedback.

25. The spatially sensitive augmented reality system of claim 24, wherein the visual feedback of whether the electrode assembly is placed on the patient's body according to the desired electrode placement position comprises a visual indication on the visual display of at least one of whether the electrode assembly is properly placed and interactive guidance of where the electrode assembly should be placed.

26. The spatially sensitive augmented reality system of claim 25, wherein the visual feedback of whether the electrode assembly is placed on the patient's body according to the desired electrode placement position comprises at least one of a color change in the virtual electrode assembly, a textual message in the field of view, and a graphical indication of whether the electrode assembly is properly placed.

27. The spatially sensitive augmented reality system of claim 1, wherein the at least one virtual three-dimensional object comprises a virtual CPR indicator overlaid on or within the patient's body within the field of view of the acute care provider, wherein the virtual CPR indicator provides feedback representative of a quality with which the acute care provider is administering CPR to the patient.

28. The spatially sensitive augmented reality system of claim 27, wherein the virtual CPR indicator comprises a chest compression indicator that provides feedback representative of a quality with which the acute care provider is administering chest compressions to the patient according to whether one or more chest compression parameters are within a desired range.

29. The spatially sensitive augmented reality system of claim 28, wherein the one or more chest compression parameters comprise at least one of chest compression depth, chest compression rate, acute care provider body alignment, and acute care provider fatigue.

30. The spatially sensitive augmented reality system of claim 27, wherein the virtual CPR indicator comprises a ventilation indicator that provides feedback representative of a quality with which the acute care provider is administering ventilations to the patient according to whether one or more ventilation parameters are within a desired range.

31. The spatially sensitive augmented reality system of claim 30, wherein the one or more ventilation parameters comprise at least one of tidal volume, minute volume, ventilation rate, flow rate in the patient's airway, inspiratory flow rate, expiratory flow rate, acute care provider body alignment, and acute care provider fatigue.

32. The spatially sensitive augmented reality system of claim 1, wherein the one or more spatially sensitive rules comprise rules for positioning the at least one virtual three-dimensional object relative to one or more identified physical objects.

33. The spatially sensitive augmented reality system of claim 1, wherein the at least one processor is configured to determine an occurrence of one or more acute care activities based on analysis of the three-dimensional representation and determine one or more activity parameters for the one or more acute care activities of the acute care provider, wherein the one or more parameters comprise one or more of chest compression rate, chest compression depth, ventilation tidal volume, ventilation minute volume, and ventilation rate.

34. The spatially sensitive augmented reality system of claim 1, wherein the emergency resuscitative guidance is based on a comparison between parameters for one or more resuscitation activities performed by the acute care provider identified based on analysis of the three-dimensional representation and target parameters for the one or more resuscitation activities performed by the acute care provider.

35. The spatially sensitive augmented reality system of claim 34, wherein the at least one processor is further configured to modify or update the target parameters based on one or more of a condition of the patient, a condition of the acute care provider, a duration of performance of the resuscitation activity, a quality of resuscitation activities being performed, a characteristic of the rescue scene, and a characteristic of other rescuers at the rescue scene.

36. The spatially sensitive augmented reality system of claim 1, wherein the emergency resuscitative guidance comprises virtual three-dimensional objects representative of one or more resuscitation activity parameters representative of a quality of resuscitation activities performed by the acute care provider.

37. The spatially sensitive augmented reality system of claim 36, wherein the parameters representative of a quality of resuscitation activities performed by the acute care provider comprise one or more of chest compression depth, chest compression rate, acute care provider body alignment, and acute care provider fatigue.

38. The spatially sensitive augmented reality system of claim 1, wherein the virtual three-dimensional object comprises an indicator representative of performance of a resuscitation activity performed by the acute care provider over a predetermined time interval or over a predetermined number of preceding instances of performance of the resuscitation activity.

39. The spatially sensitive augmented reality system of claim 1, further comprising a flow sensor in fluid communication with a ventilation device for providing ventilations to the patient, and wherein the flow sensor is configured to measure one or more of tidal volume, minute volume, ventilation rate, flow rate in the patient's airway, inspiratory flow rate, and expiratory flow rate.

40. The spatially sensitive augmented reality system of claim 39, wherein the at least one processor is further configured to receive information from the flow sensor, and wherein the emergency resuscitative guidance is based, at least in part, on the information received from the flow sensor.

41. The spatially sensitive augmented reality system of claim 1, wherein the identification of the one or more physical objects by the at least one processor comprises identification of at least one medical imaging probe in the three-dimensional representation, the imaging probe being configured to capture image data representative of at least one internal body structure of the patient.

42. The spatially sensitive augmented reality system of claim 41, wherein the at least one internal body structure comprises at least one of organ(s), bone(s), muscle(s), soft tissue(s), or blood vessel(s) of the patient.

43. The spatially sensitive augmented reality system of claim 41, wherein the medical imaging probe comprises an ultrasound transducer, and wherein the at least one internal body structure comprises a heart of the patient.

44. The spatially sensitive augmented reality system of claim 41, wherein the at least one processor of the augmented reality device is configured to:
determine a location of the at least one imaging probe within the three-dimensional representation of the scene,
receive the image data from the at least one imaging probe, and
associate the received image data with the location of the imaging probe within the three-dimensional representation when the image data was captured.

45. The spatially sensitive augmented reality system of claim 44, wherein the at least one processor of the augmented reality device is further configured to analyze the received image data from the imaging probe to identify the internal body structure in the captured image data, and
wherein the generated at least one virtual object comprises a virtual representation of the identified internal body structure.

46. The spatially sensitive augmented reality system of claim 45, wherein at least one of a size, outward appearance, movement, or positioning of the at least one virtual object is based, at least in part, on the image data from the imaging probe.

47. The spatially sensitive augmented reality system of claim 44, wherein the manipulation of the image of the virtual three-dimensional object within the three-dimensional representation on the visual display is based, at least in part, on the image data from the imaging probe.

48. The spatially sensitive augmented reality system of claim 44, wherein the manipulation of the image of the virtual three-dimensional object comprises causing the image to be displayed within the field of view of the user at a position relative to the patient determined based, at least in part, on the image data from the imaging probe.

49. The spatially sensitive augmented reality system of claim 1, further comprising a medical imaging probe configured to capture image data representative of at least one interior body structure of the patient, the medical imaging probe being in wireless electronic communication with the at least one processor of the augmented reality device,
wherein the at least one processor is configured to identify the medical imaging probe in the three-dimensional representation of the field of view of the acute care provider.

50. The spatially sensitive augmented reality system of claim 1, wherein the identification of the one or more physical objects in the three-dimensional representation by the at least one processor comprises identification of at least one insertable medical instrument configured to be inserted through a mouth of the patient.

51. The spatially sensitive augmented reality system of claim 50, wherein the at least one insertable medical instrument comprises at least one of a tracheal tube or laryngoscope.

52. The spatially sensitive augmented reality system of claim 50, wherein the identification of the insertable medical instrument in the three-dimensional representation further comprises identification of a tag or code associated with the insertable medical instrument, and wherein the at least one processor of the augmented reality device is configured to determine information about the insertable medical instrument based on the tag or code.

53. The spatially sensitive augmented reality system of claim 52, wherein the determined information comprises information about a length, inner cross section area, outer cross section area, flexibility, manufacturer, model number, or outward appearance of the insertable medical instrument.

54. The spatially sensitive augmented reality system of claim 52, wherein the generation of the at least one virtual three-dimensional object within the three-dimensional representation comprises generation of a virtual representation of the insertable medical instrument, and
wherein the generation of the image of the virtual representation of the insertable medical instrument on the visual display is based, at least in part, on information determined from the tag or code associated with the insertable medical instrument.

55. The spatially sensitive augmented reality system of claim 1, wherein the at least one processor of the augmented reality device is further configured to receive image data captured from a medical instrument inserted into the patient through the mouth.

56. The spatially sensitive augmented reality system of claim 55, wherein the generation of the at least one virtual three-dimensional object within the three-dimensional representation comprises generation of a virtual representation of an interior body structure of the patient determined based, at least in part, on the received image data from the inserted medical instrument, and
wherein the generation of the image of the virtual representation on the visual display is based, at least in part, on the received image data.

57. The spatially sensitive augmented reality system of claim 56, wherein the image of the virtual representation of the interior body structure comprises an image of the interior body structure and at least one annotation identifying the interior body structure.

58. The spatially sensitive augmented reality system of claim 55, wherein the at least one processor of the augmented reality device is configured to display the received image data on the visual display in real time, wherein the received image data comprises image data captured from a camera associated with at least one of a tracheal tube or a laryngoscope inserted through the patient's mouth.

59. The spatially sensitive augmented reality system of claim 58, wherein the at least one processor of the augmented reality device is further configured to automatically analyze the received image data captured from the inserted medical instrument to determine at least one notification related to insertion of the inserted medical instrument and/or treatment of the patient, and to display the at least one notification on the visual display along with the displayed received image data, thereby providing guidance for insertion of the medical instrument through the mouth of the patient and/or treatment of the patient.

* * * * *